(12) United States Patent
Romano et al.

(10) Patent No.: US 8,137,329 B2
(45) Date of Patent: Mar. 20, 2012

(54) METHOD AND APPARATUS FOR TRANSFORMING A DELIVERY CONTAINER INTO A WASTE DISPOSAL SYSTEM

(75) Inventors: Jack W. Romano, Newcastle, WA (US); Adam L. Smith, Olalla, WA (US)

(73) Assignee: Medindica-Pak, Inc., Kirkland, WA (US)

( * ) Notice: Subject to any disclaimer, the term of this patent is extended or adjusted under 35 U.S.C. 154(b) by 0 days.

(21) Appl. No.: 11/087,538

(22) Filed: Mar. 23, 2005

(65) Prior Publication Data

US 2005/0215961 A1  Sep. 29, 2005

Related U.S. Application Data

(60) Provisional application No. 60/556,274, filed on Mar. 25, 2004.

(51) Int. Cl.
*A61M 1/00* (2006.01)

(52) U.S. Cl. .................................. 604/319; 604/322

(58) Field of Classification Search ............... 604/8–10, 604/39, 317–322, 411
See application file for complete search history.

(56) References Cited

U.S. PATENT DOCUMENTS

| 3,032,037 | A | * | 5/1962 | Havirco ..................... 604/245 |
| 4,178,976 | A | * | 12/1979 | Weiler et al. ................ 604/415 |
| 4,388,922 | A | * | 6/1983 | Telang ........................ 604/319 |
| 4,397,643 | A | * | 8/1983 | Rygiel ......................... 604/317 |
| 4,620,846 | A | * | 11/1986 | Goldberg et al. ............. 604/28 |
| 5,364,384 | A | * | 11/1994 | Grabenkort et al. ......... 604/408 |
| 5,382,244 | A | * | 1/1995 | Telang ........................ 604/319 |
| 5,514,123 | A | * | 5/1996 | Adolf et al. ................. 604/411 |
| 5,713,879 | A | * | 2/1998 | Schneider ................... 604/319 |
| 5,960,837 | A | * | 10/1999 | Cude ........................... 141/65 |
| 6,318,417 | B1 | * | 11/2001 | Davis et al. .................. 141/1 |
| 7,185,681 | B2 | * | 3/2007 | Romano ....................... 141/9 |
| 2002/0128612 | A1 | * | 9/2002 | Andersson et al. ......... 604/256 |
| 2003/0079803 | A1 | * | 5/2003 | Romano ..................... 141/234 |
| 2003/0132249 | A1 | * | 7/2003 | Romano ..................... 222/181.1 |
| 2004/0122383 | A1 | * | 6/2004 | Romano et al. ............. 604/319 |

* cited by examiner

*Primary Examiner* — Leslie Deak
*Assistant Examiner* — Philip R Wiest

(57) ABSTRACT

This application teaches practical and cost effective methods and apparatus to enhance supply chain efficiency by transforming fluid enclosing supply delivery containers in to collection and disposal containers, and in particular, providing inter alia, a canister system having a lid which would couple to either a thread able supply container or a spike able supply container. This enables the user to select from a plurality of supply containers for the collection and removal of waste such as a threaded pour bottle type of supply container, or a spike able type of intravenous solution supply container.

71 Claims, 28 Drawing Sheets

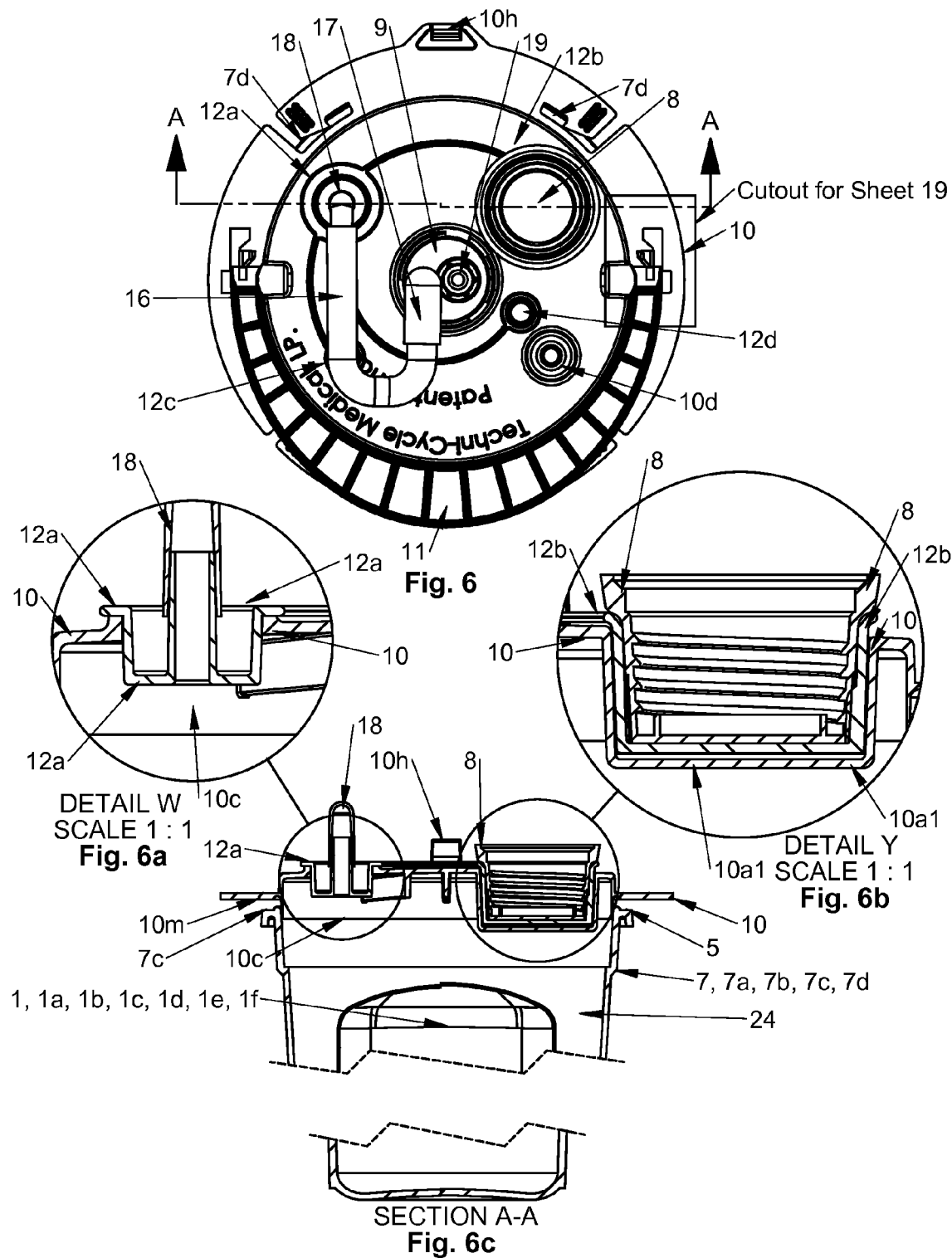

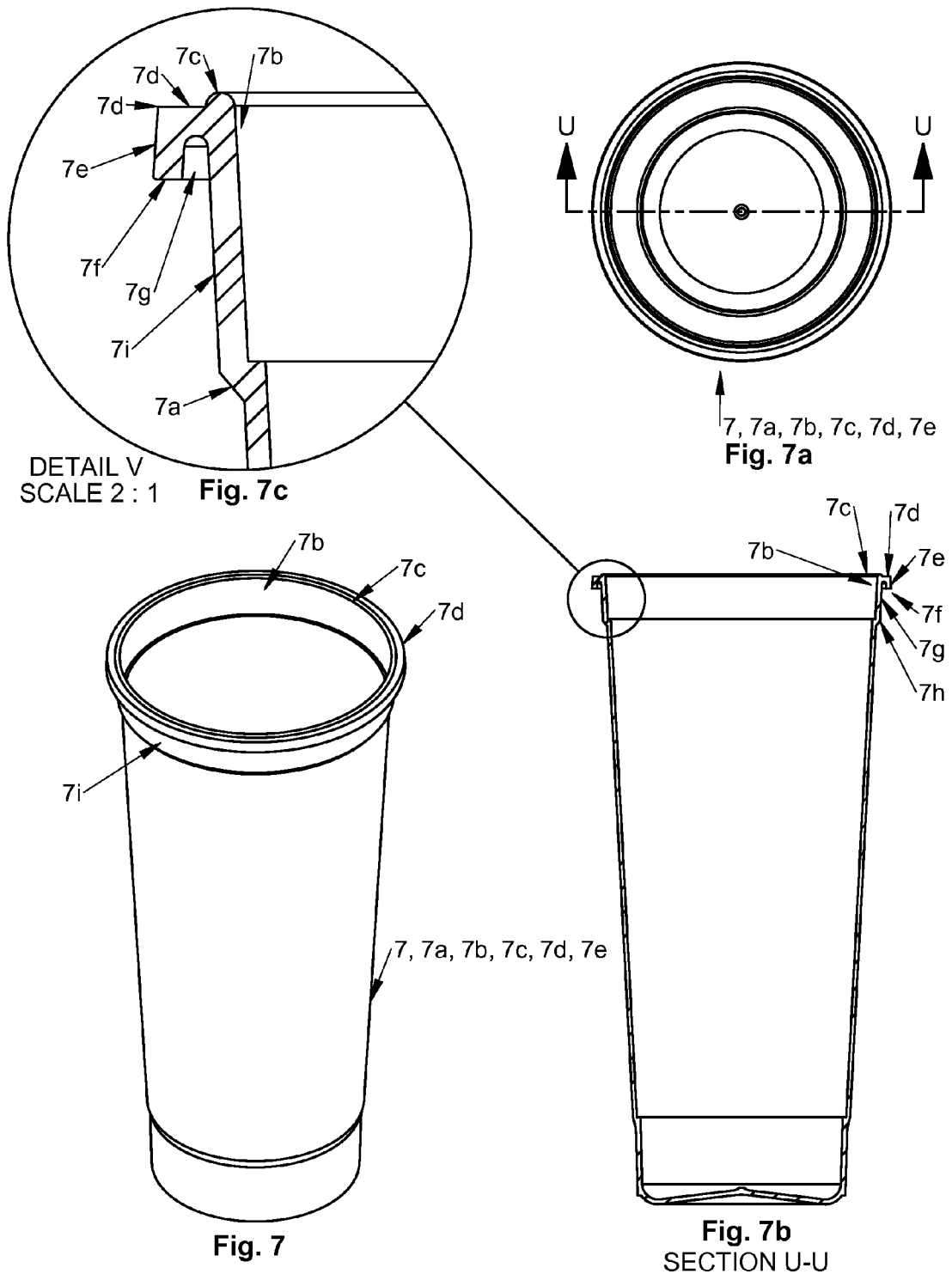

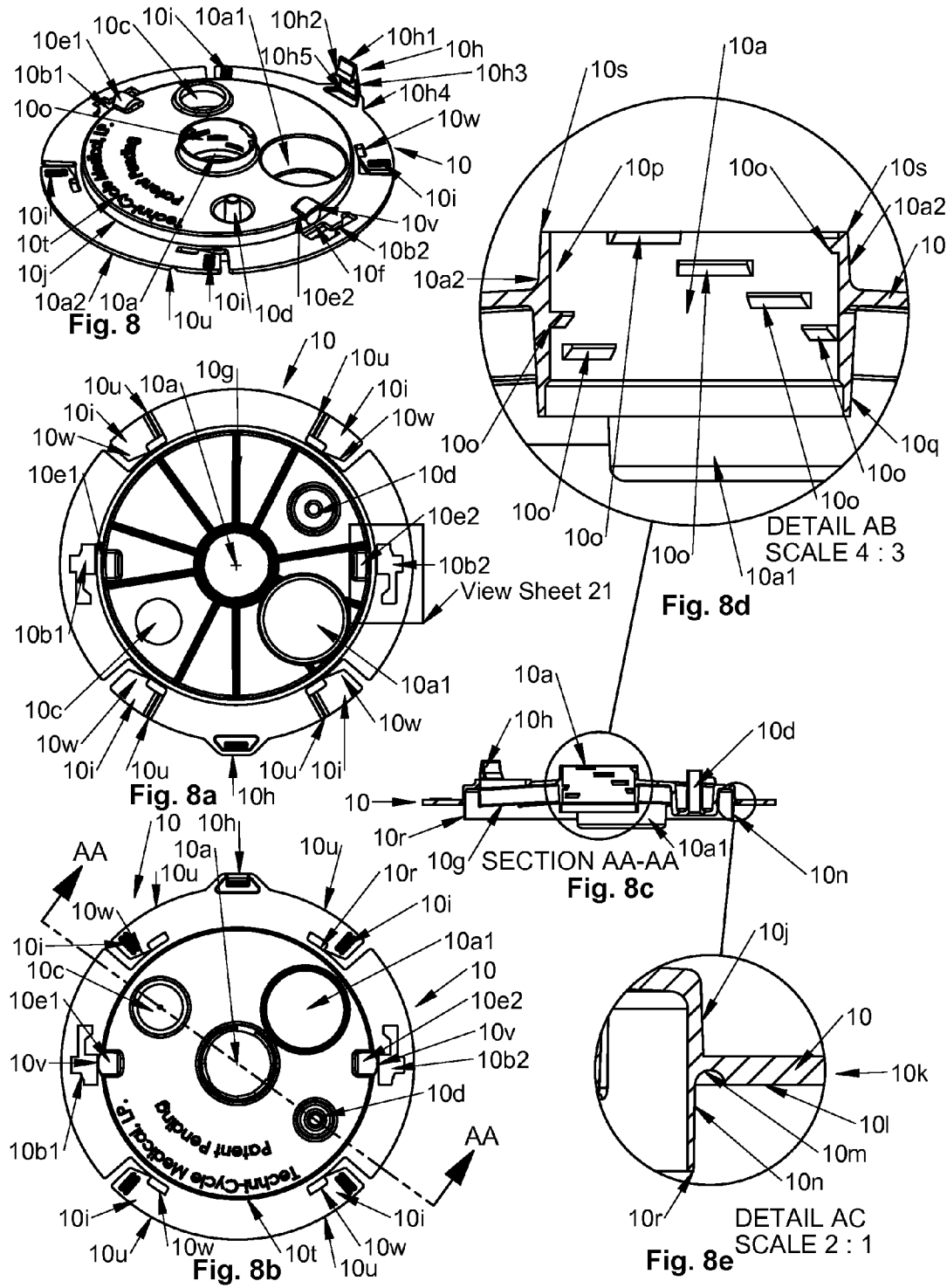

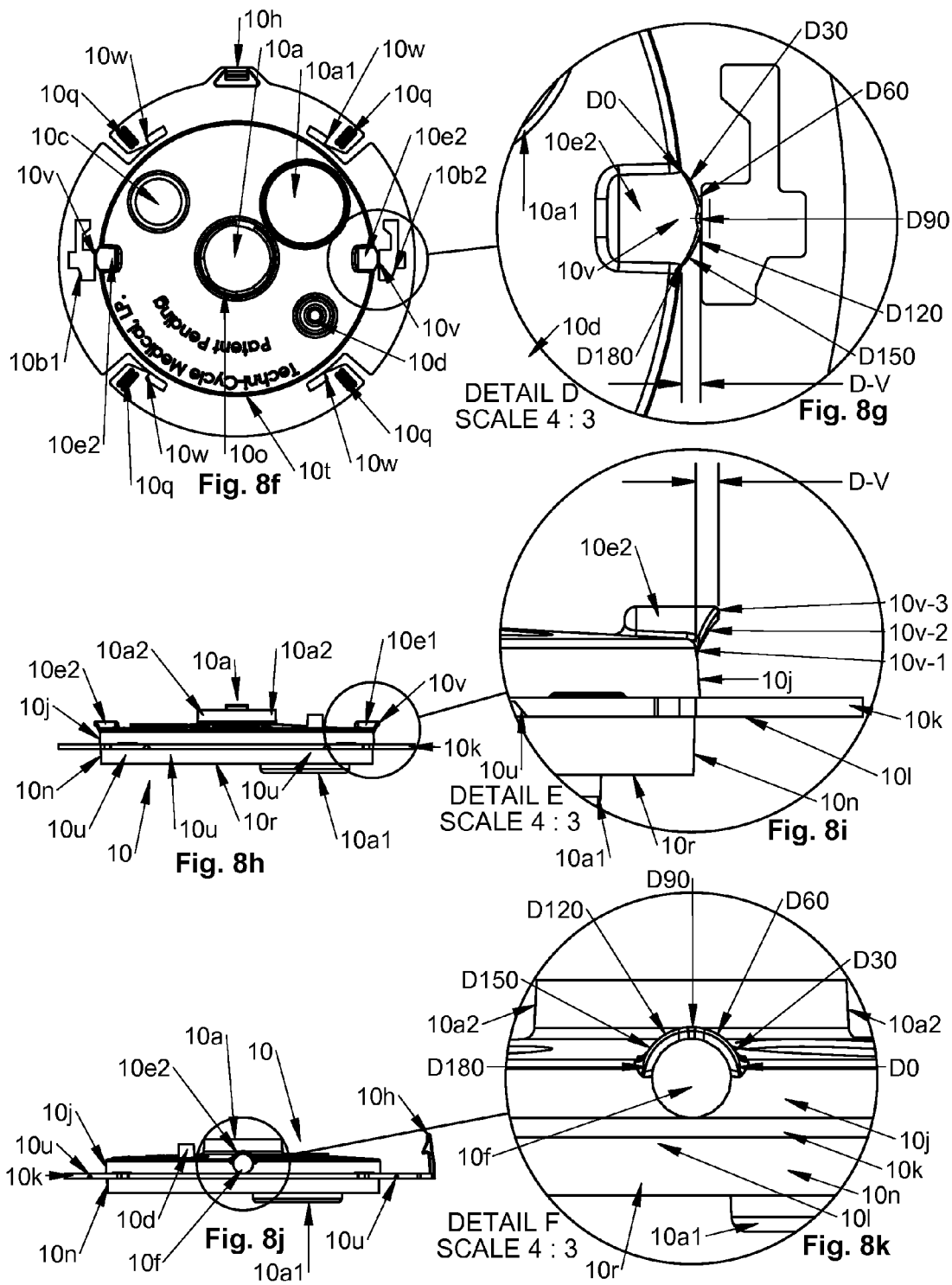

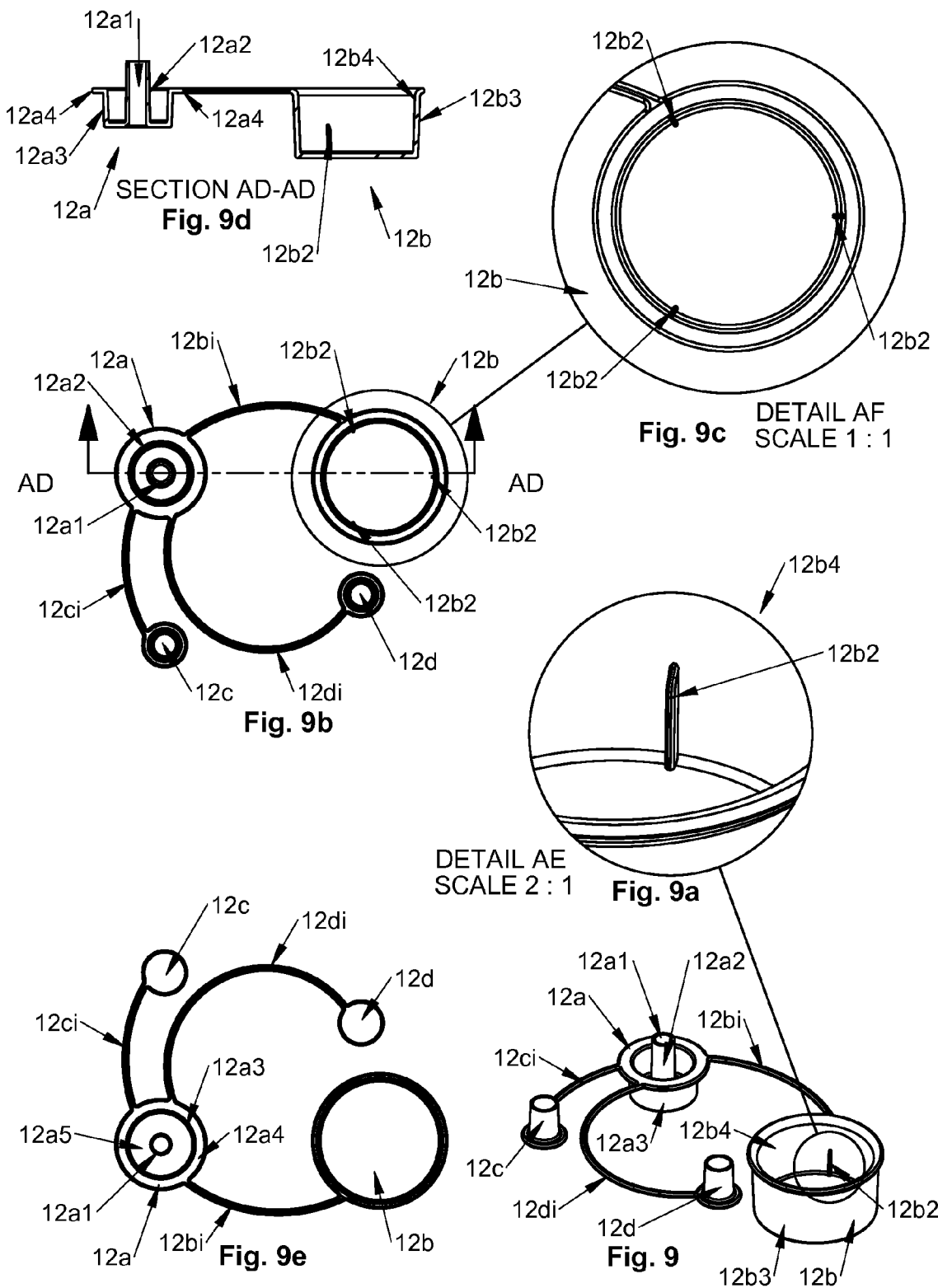

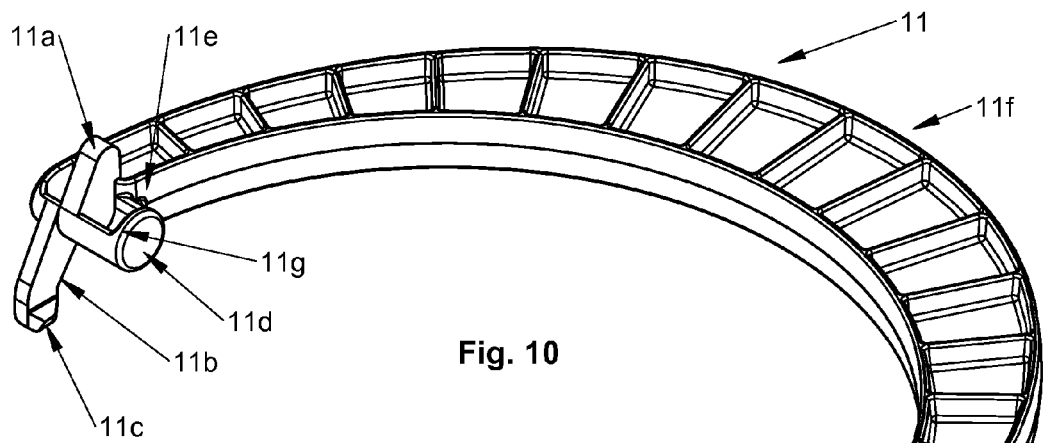
Fig. 10
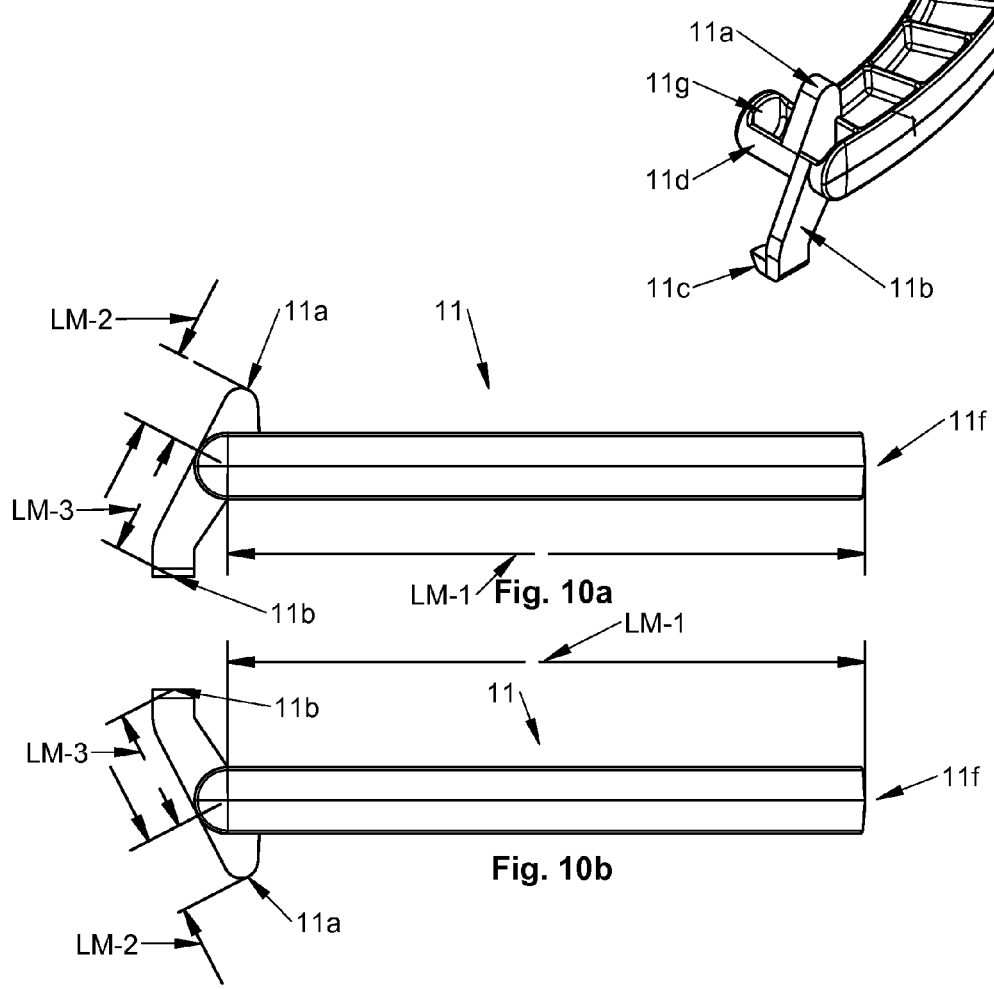
Fig. 10a
Fig. 10b

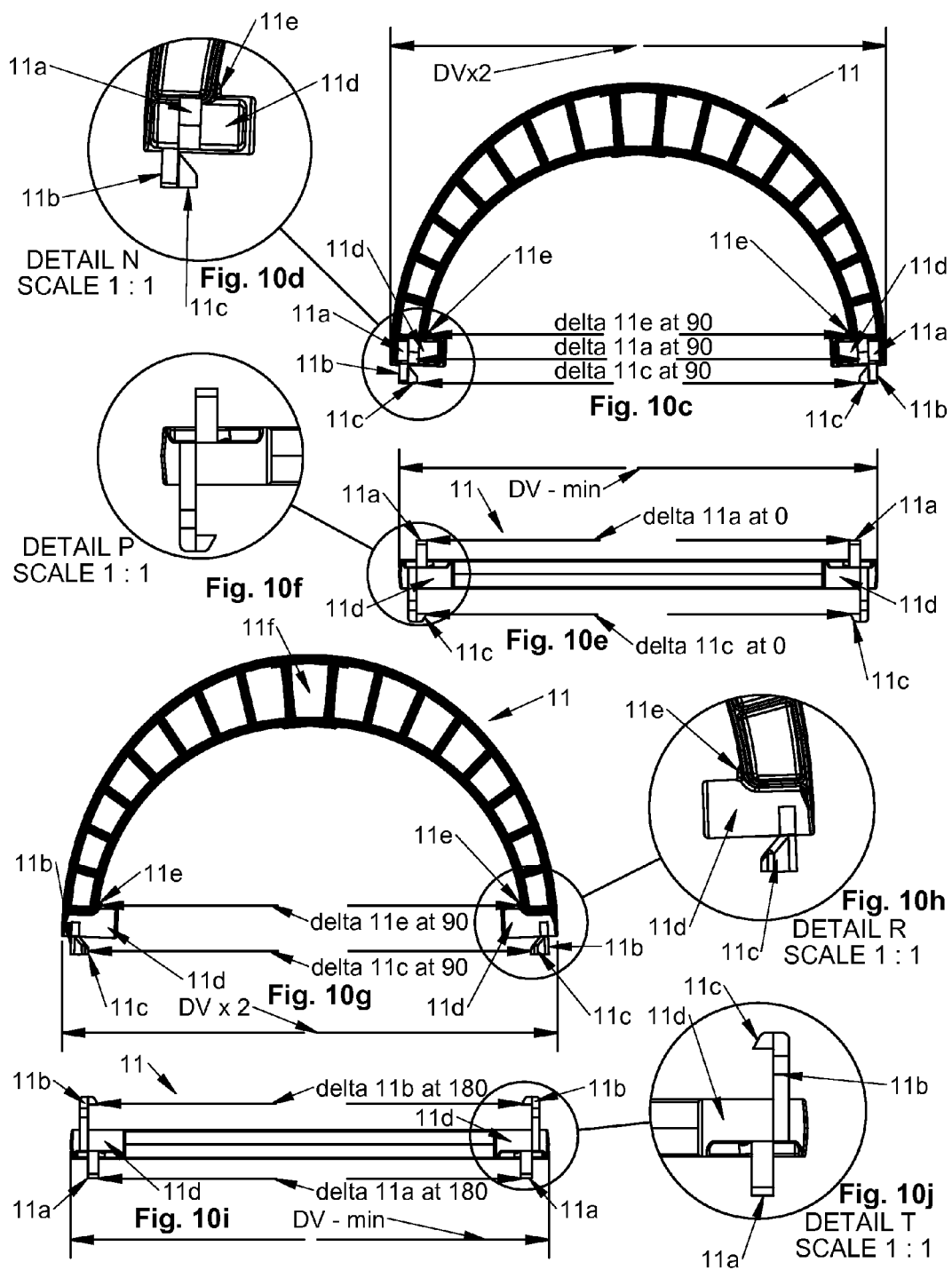

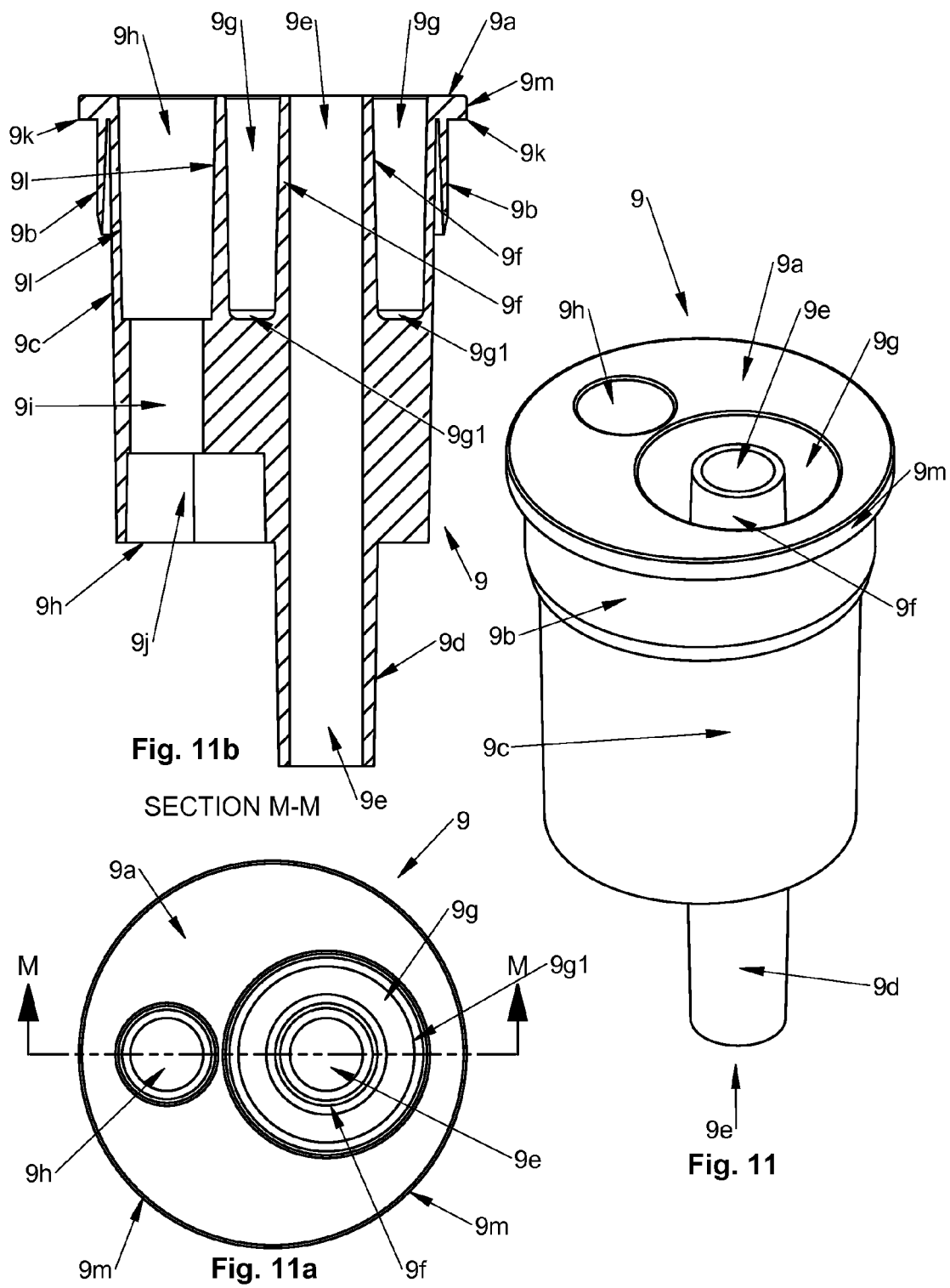

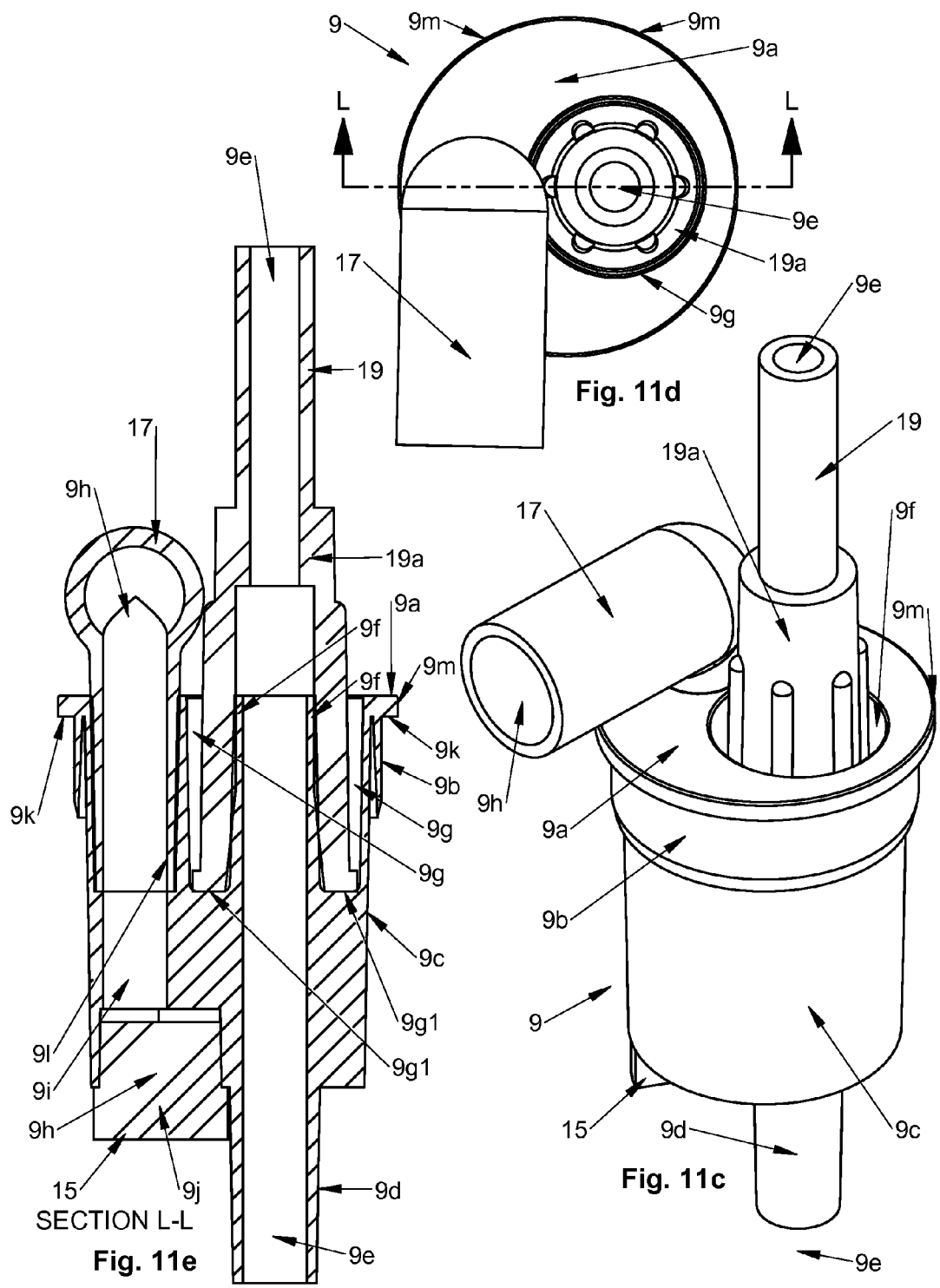

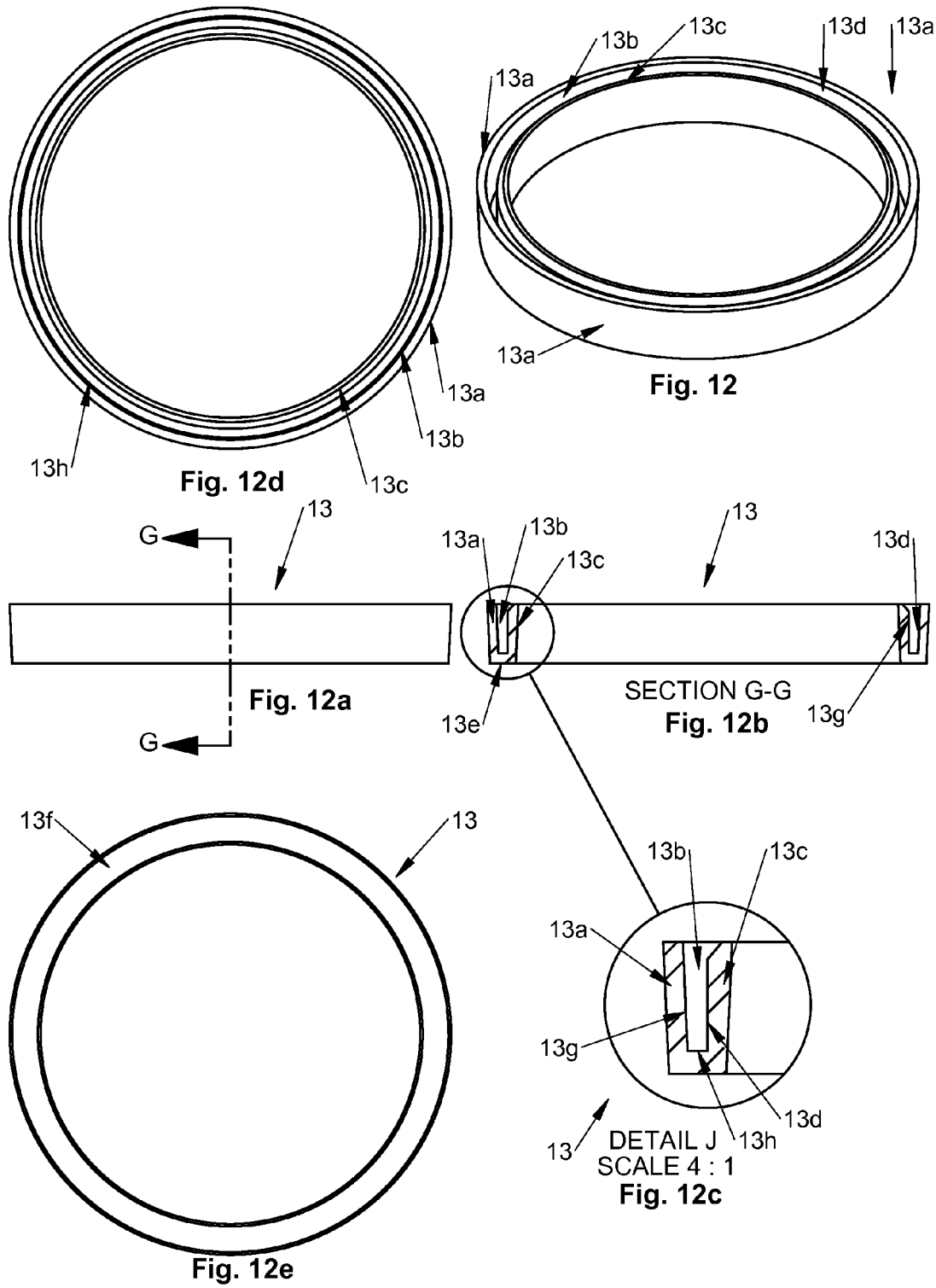

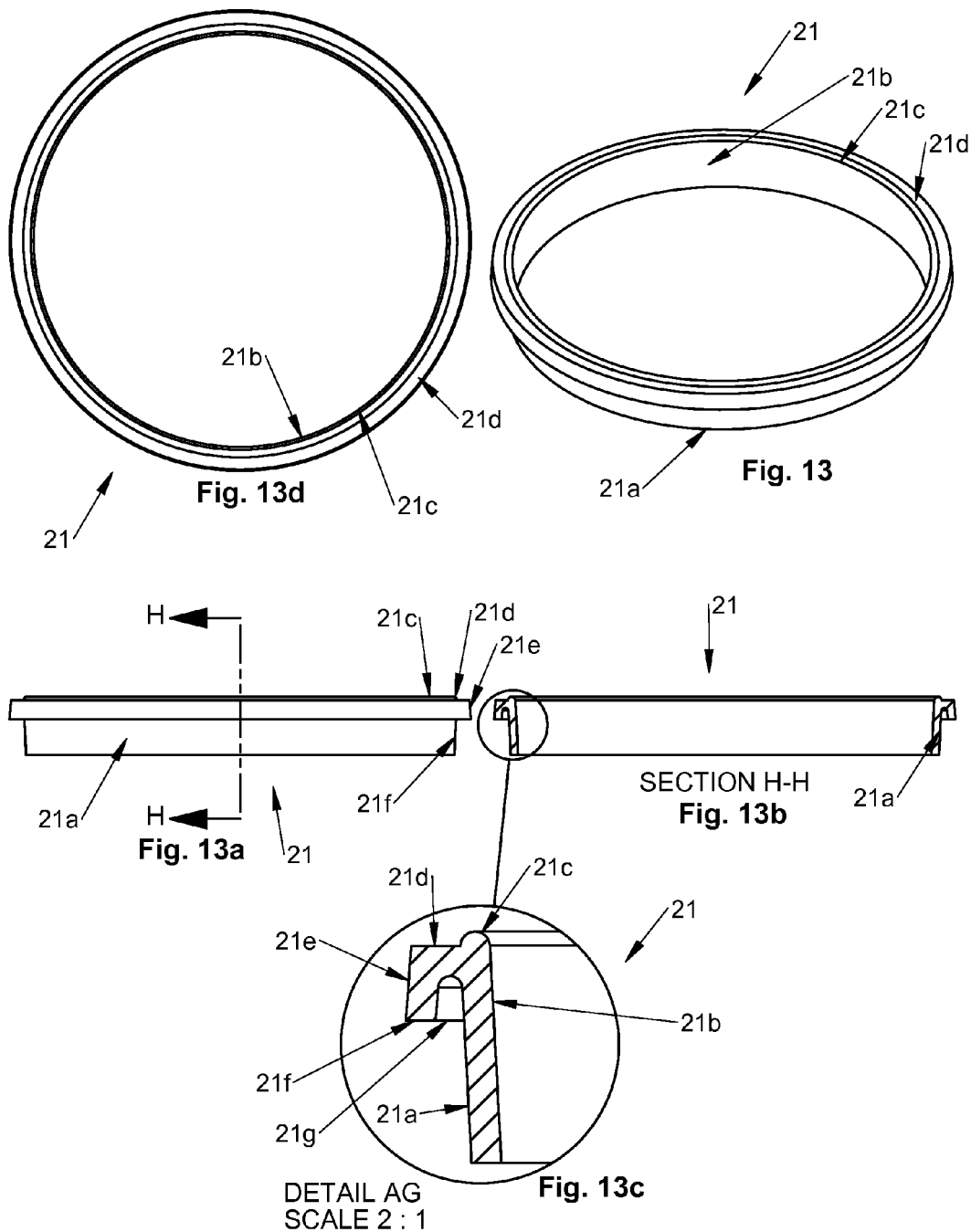

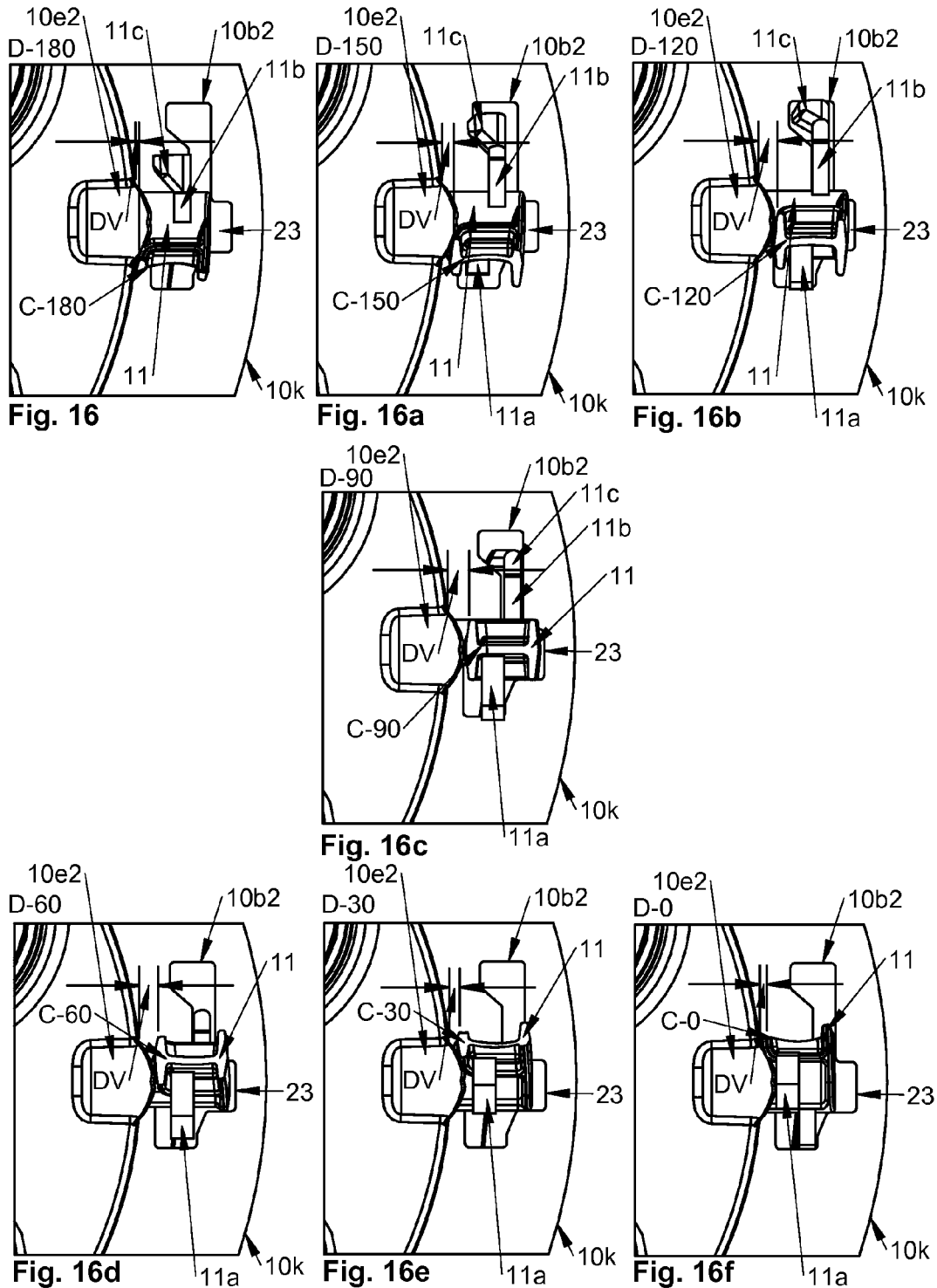
(cutout of Fig. 8g on Sheet 9)

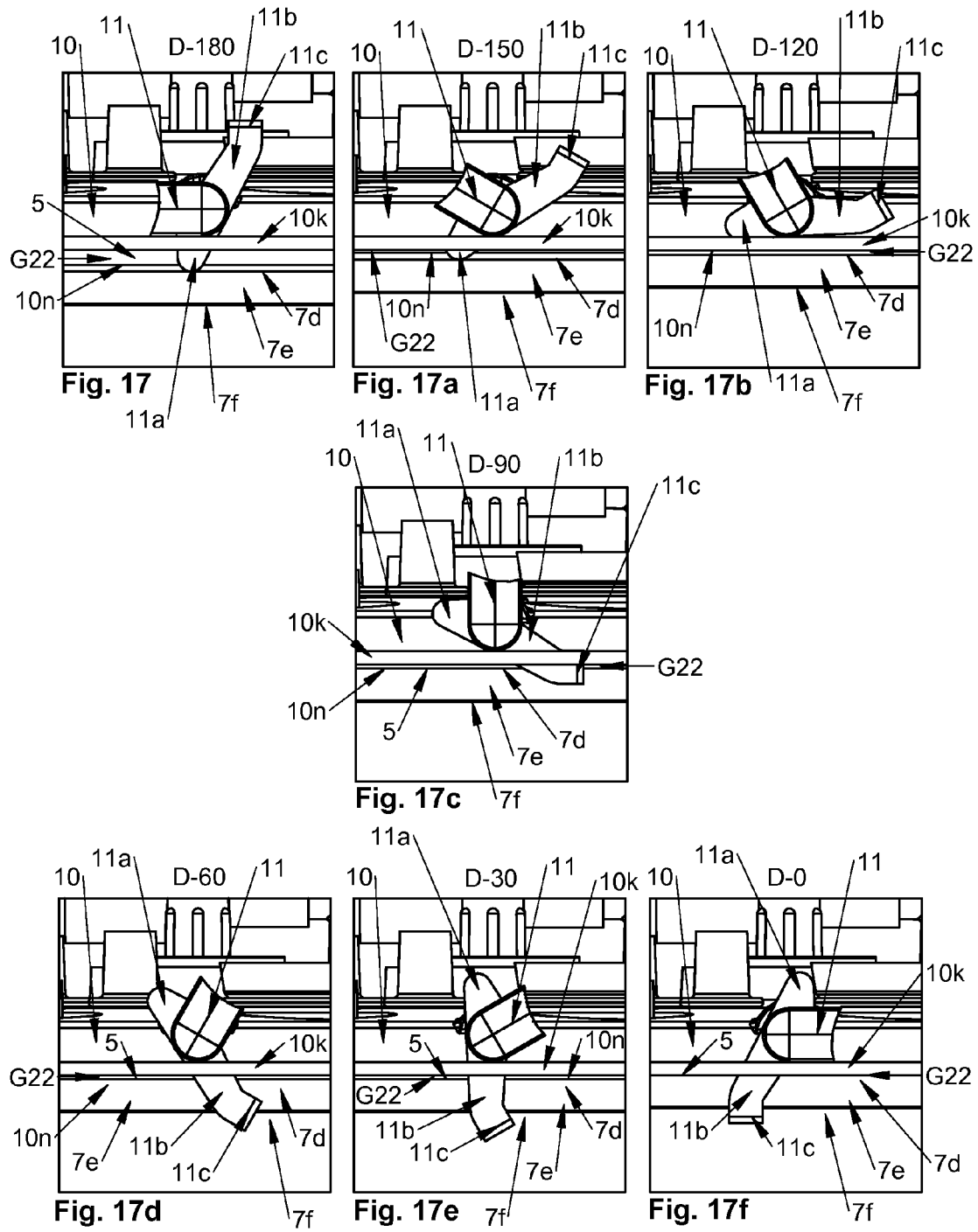
(Blow up from Sheets 17 & 18)

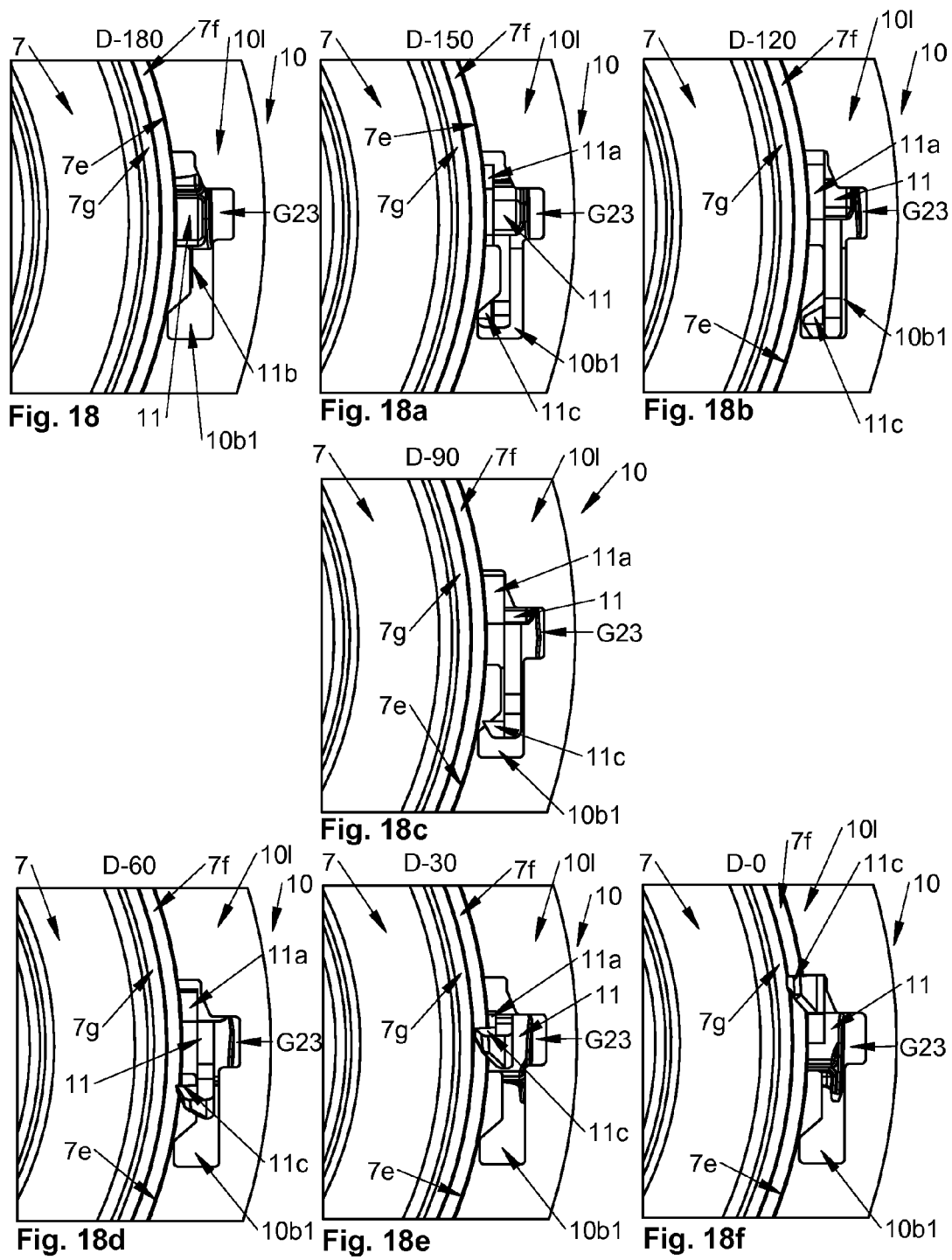
(Blow up from Fig. 8a of Sheet 8)

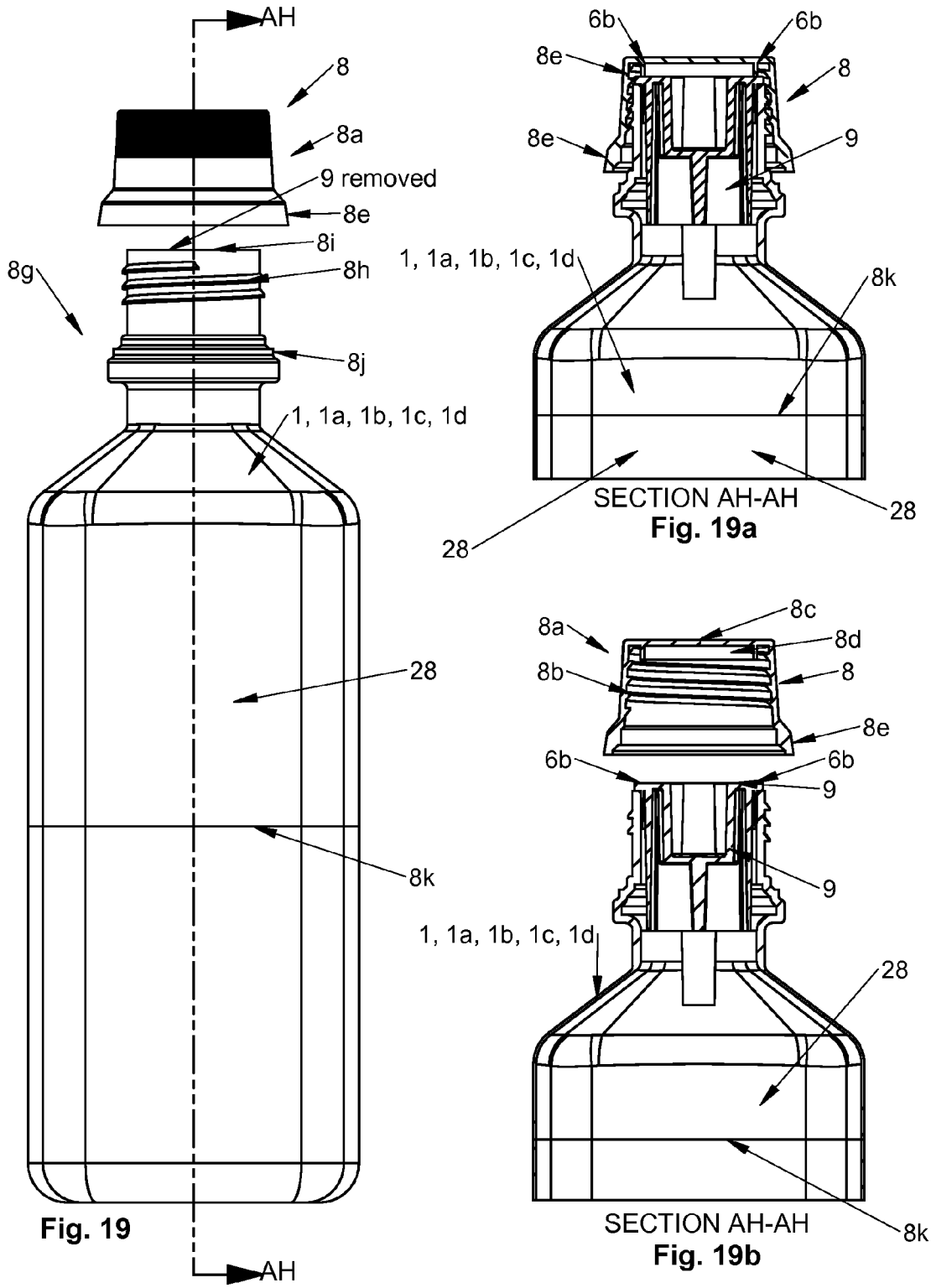

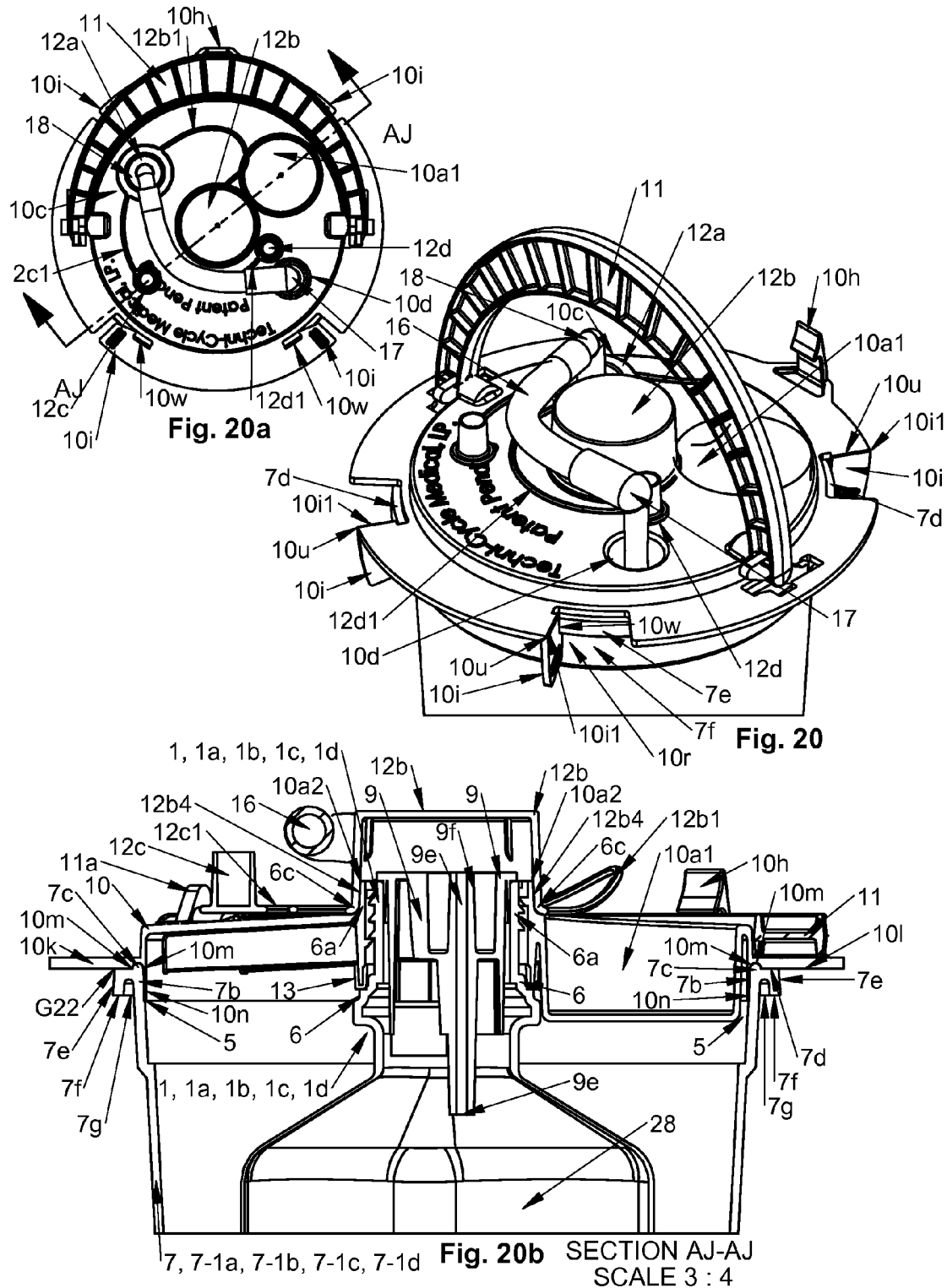

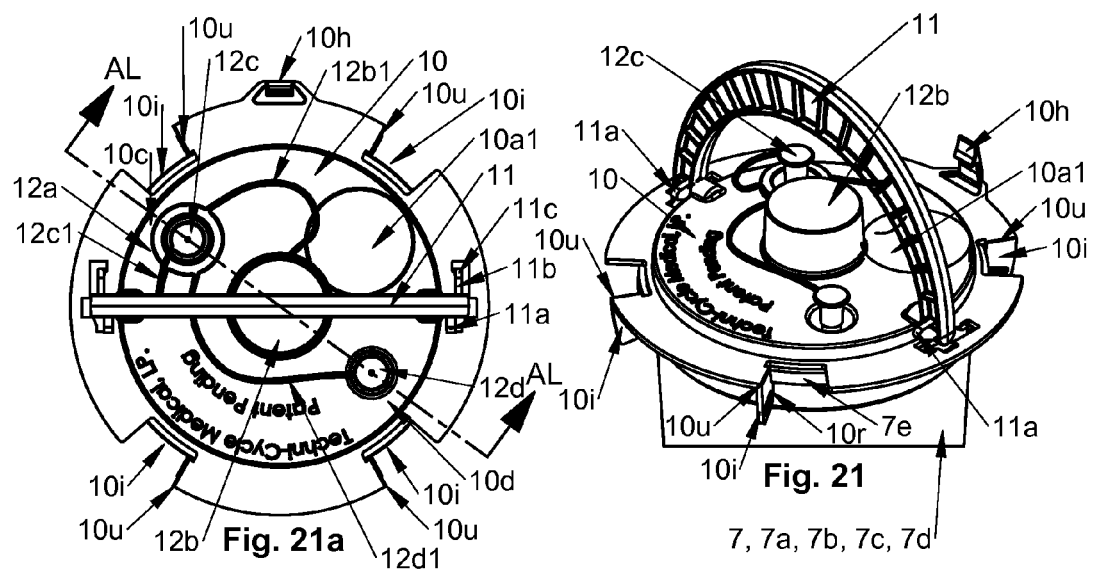
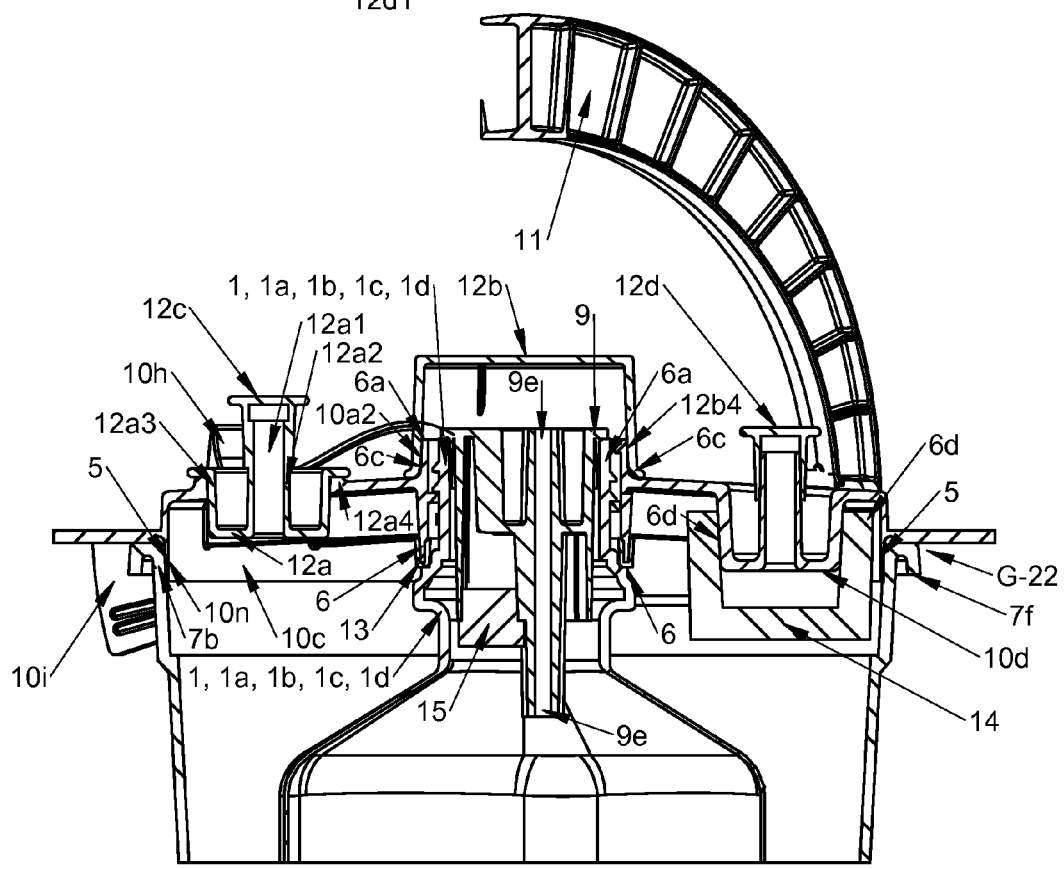

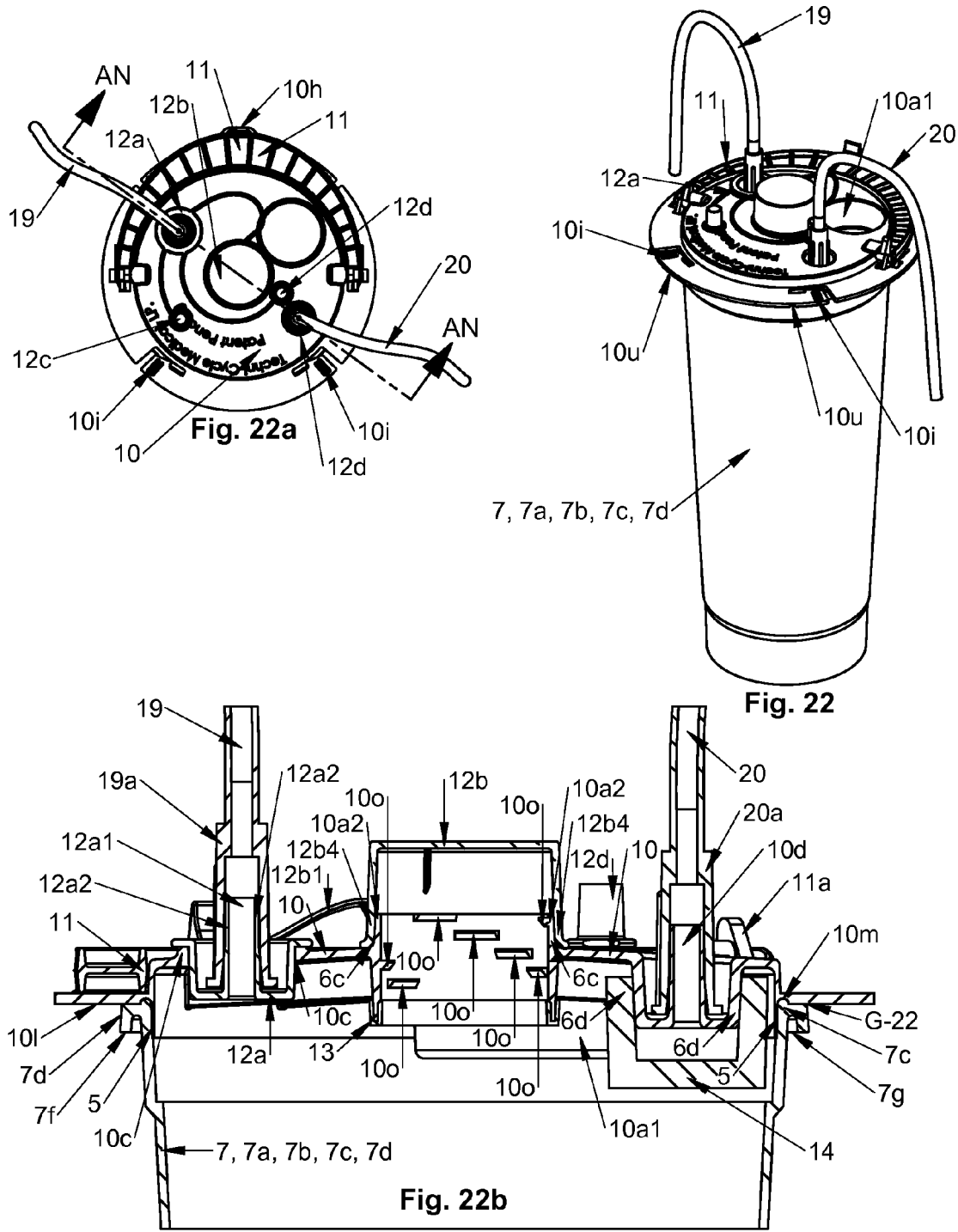

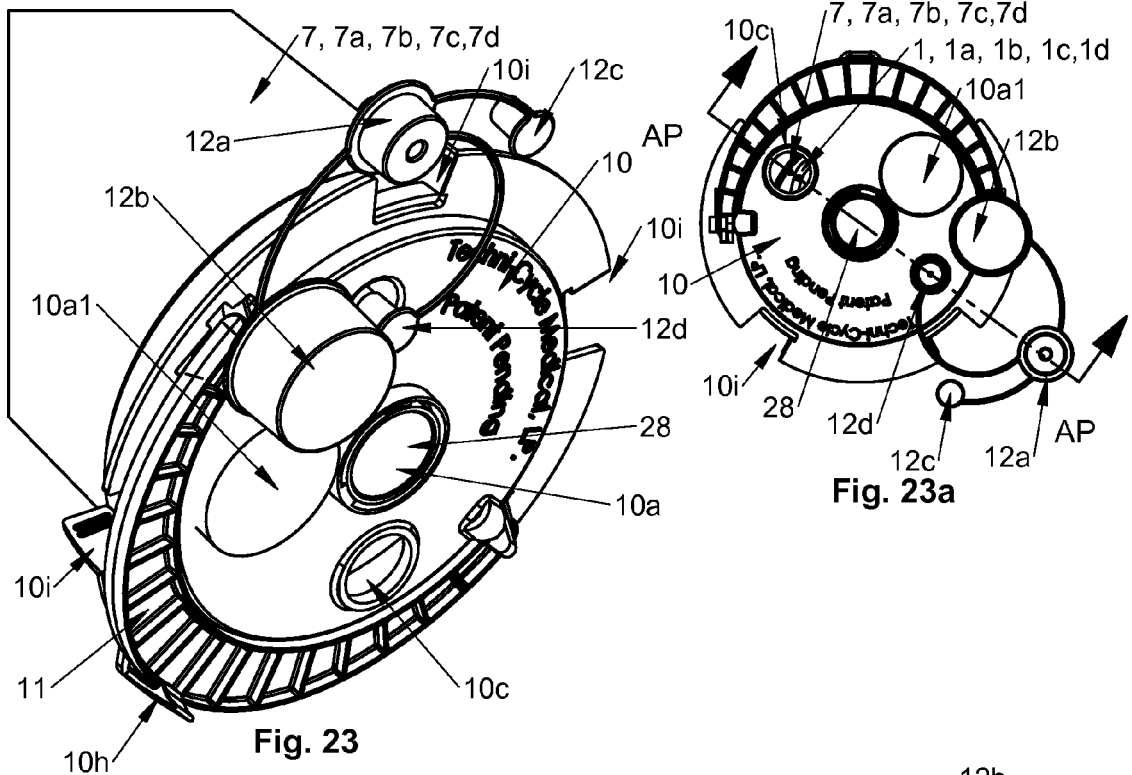
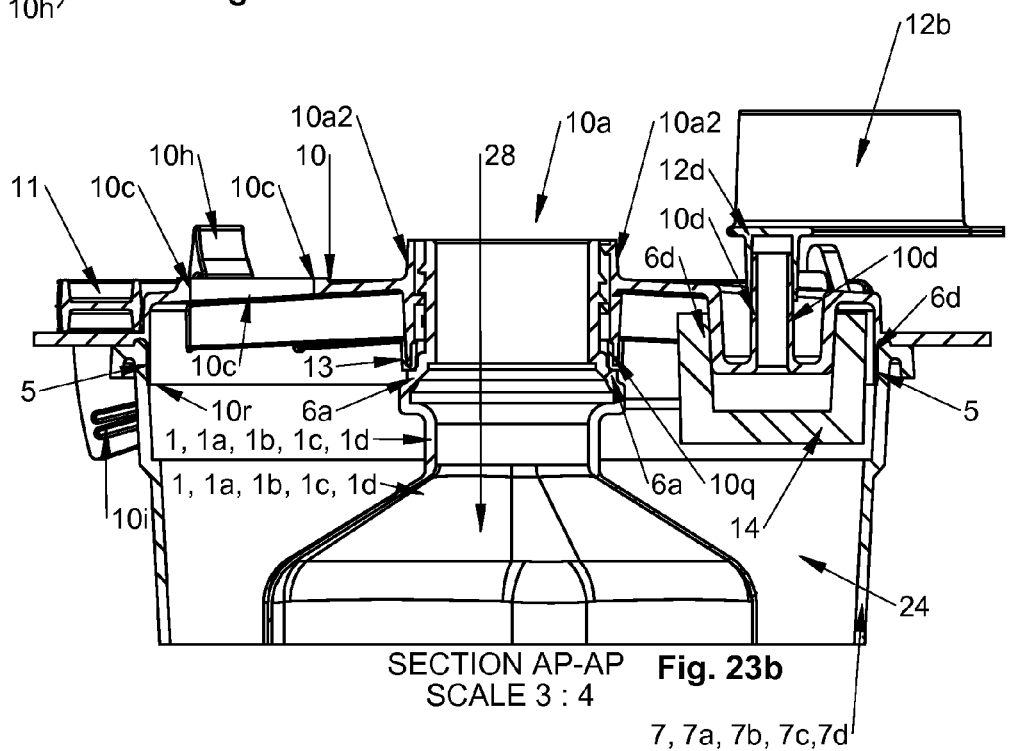

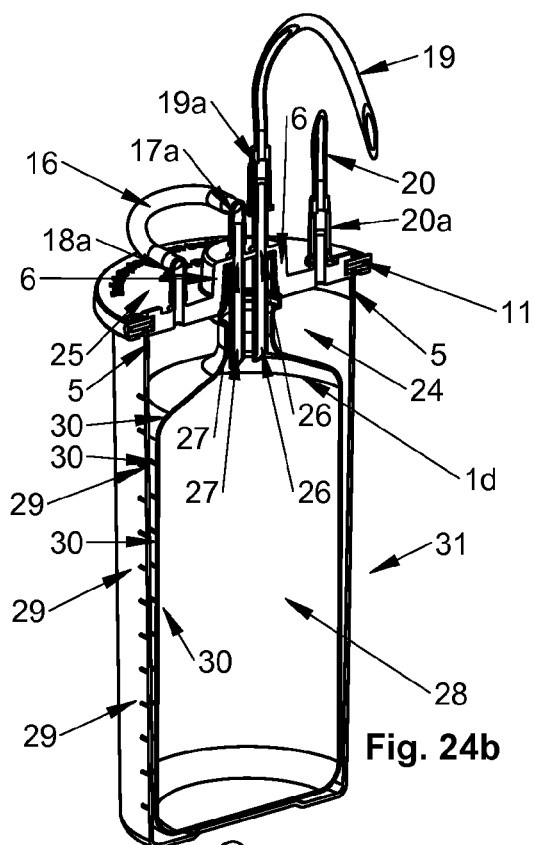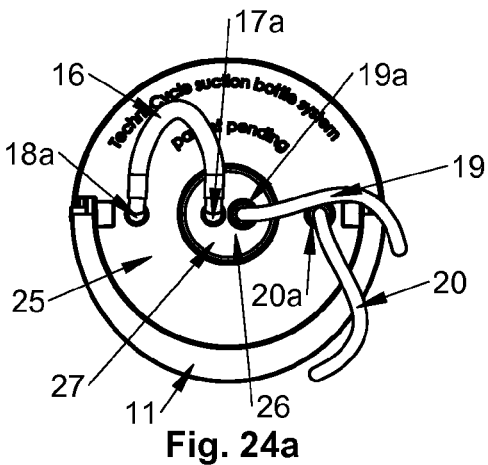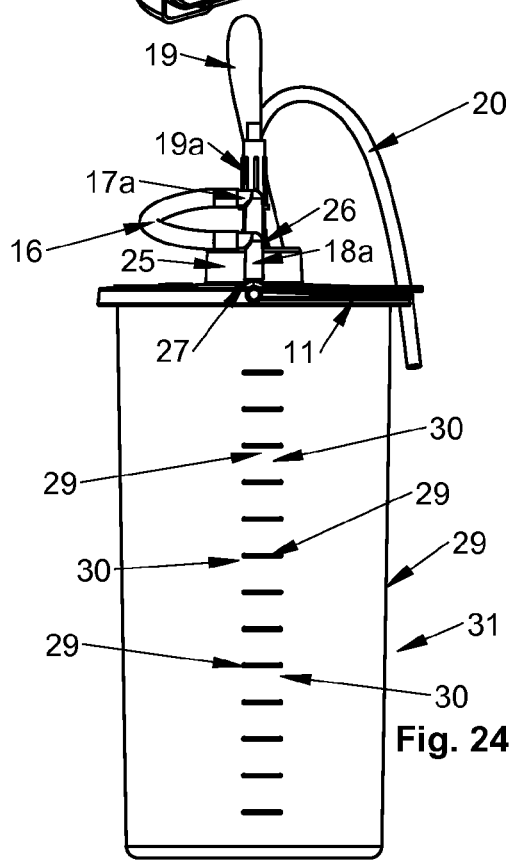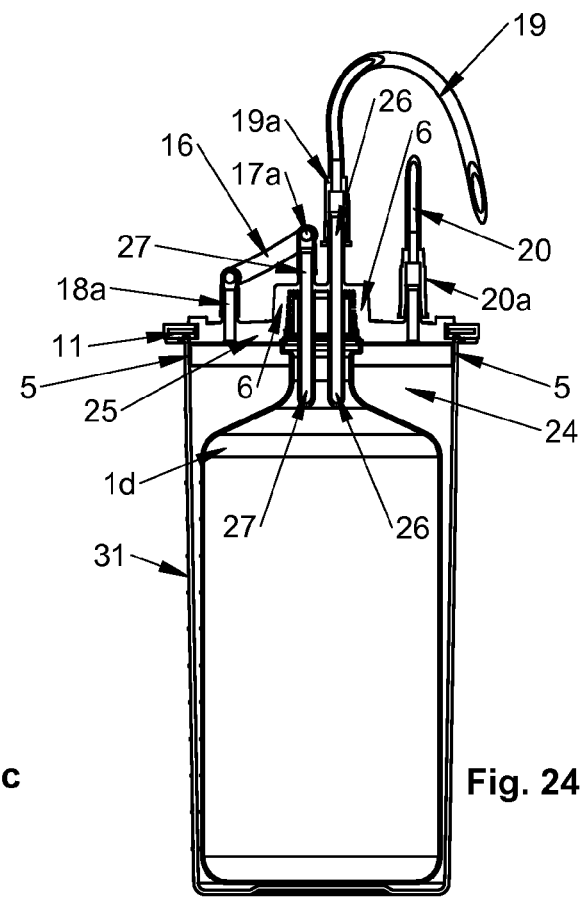
Fig. 24b
Fig. 24a
Fig. 24c
Fig. 24

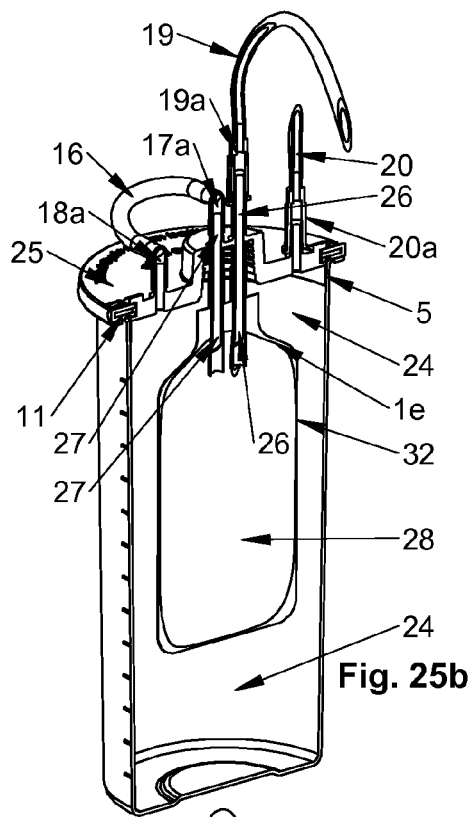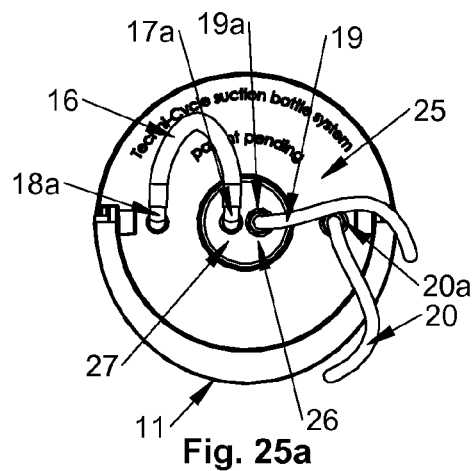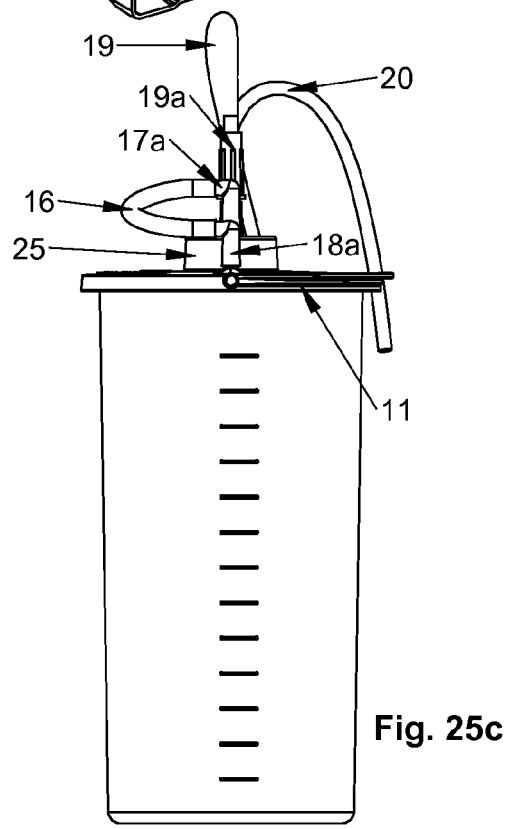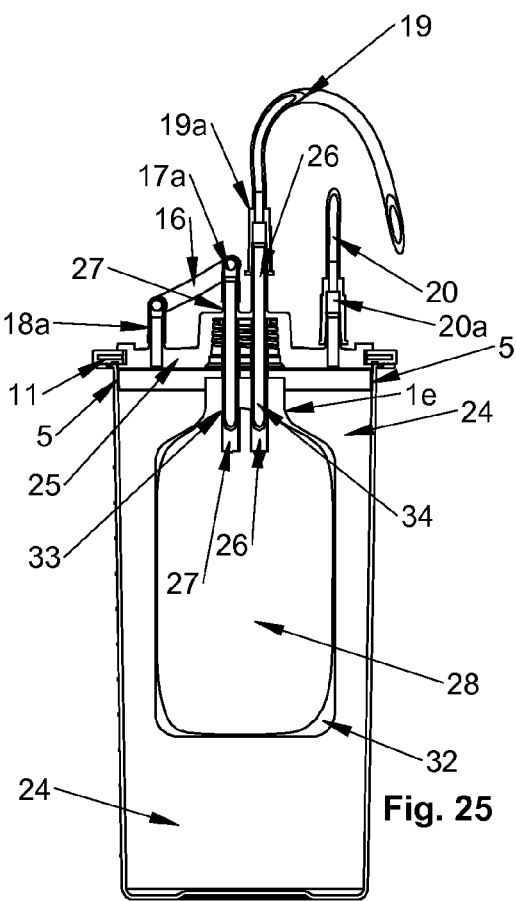
Fig. 25b
Fig. 25a
Fig. 25c
Fig. 25

METHOD AND APPARATUS FOR TRANSFORMING A DELIVERY CONTAINER INTO A WASTE DISPOSAL SYSTEM

CROSS REFERENCE TO RELATED APPLICATION

This application claims the benefit under 35 U.S.C 119(e) of U.S. Provisional Patent Application Ser. No. 60/556,274 filed on Mar. 25, 2004.

FIELD OF THE INVENTION

This invention(s) relates to the field of reducing the waste stream burden in the medical field.

BACKGROUND OF THE INVENTION

In particular, this application relates to systems used for the collection and disposal of certain medical waste. The collection of fluent waste material is a common procedure in the medical field. Most methods of surgical waste collection are carried out using vacuum suction. Some methods use gravity, while some use impelling devices which produce suction/vacuum. Examples of such impelling devices may comprise a meniscus shaver, a lipo-suction system, an arthroscopic fluid pump, an endoscopic irrigation and aspiration wand and the like. Surgical fluid waste is collected in containers commonly referred to as canisters, and or canister liners. These waste collection devices are generally disposable, some are recycled reprocessed or re-washed. Some collection devices are reused. Some are partially reused, while some are intermittently reused. Some are disposable or partially disposable. Some are used in conjunction with servicing units while some are used with additive agents for treating the waste material. Some are used multiple times on multiple patients without preferable cleaning between patients. In certain instances, reused devices are cleaned, reprocessed, sterilized, re-sterilized, and/or re-cycled and prepared for re-use. There are disadvantages to the use of disposable collection canisters and canister liners. One problem is that disposable collection canisters and disposable collection liners contribute contaminated infections plastic waste to the medical waste stream which is undesirable for the environment. Re-use of disposable collection devices by re-cleaning or re-processing re-cycling and/or sterilizing, has the disadvantages of adding costly labor, and requiring additional labor costs for sorting, containing, transporting and handling of contaminated medical waste canisters, and then the added costs of product re-entry into the cleaning and re-sterilization internal systems. There is a significant need to reduce medical waste. The need to reduce medical waste is a serious common goal of the US Environmental Protection Agency, and the American Hospital Association which has entered into a landmark "Memorandum of Understanding" formally establishing the goals to reduce medical waste 50% by the year 2010. Hospitals for Healthy Environment (www.h2e-online.org) is the name of the aforementioned alliance and is supported by many formidable organizations and companies such as the American Nurses Association, Health Care Without Harm, leading Group Purchasing Organizations, leading Health Care Systems, State and local government agencies, Health Care Associations and the like.

DESCRIPTION OF THE RELATED ART

Certain disadvantages of the prior art in these regards will become better understood by explanation of these following references. U.S. Pat. No. 5,792,126 to Tribastone et. al., discloses a collection canister system comprising canister interiors of preferably 5,000, 10,000 and 15,000 cubic centimeters and are taught to be effective for all procedures. A container of this size has disadvantages because it is too big for many collection applications. For example, suction collection for anesthesia, whereby it is convenient to have a small collection canister attached to an anesthesia machine is preferable, especially in that most anesthesia suction volumes constitute just a few cubic centimeters of sputum or pharangeal/throat saliva most of the time. Larger equipment is also inconvenient in smaller rooms, where suction collection equipment is found such as the emergency room, intensive care units, in patient hospital rooms, coronary care units, and neo-natal and infant care units, physician offices, physician owned surgery suites, out patient surgery centers, ambulances, and other rooms defining smaller confined spaces. There are also concerns with cross contamination in any system where contaminated waste material remains in a room/location during the presence of multiple patients. This problem is most prevalent in intensive care and other patient units where the most sick patients are treated. Another disadvantage of 5,000, 10,000 and 15,000 cubic centimeter containers is weight. Such weight in these very heavy volumes provide for extremely difficult ergonomics and handling problems posing significant risk to personnel, such as back, neck, and upper extremity injuries. Another disadvantage of such large and heavy containers is its size. Such large containers are more difficult to clean and cumbersome to handle and because the awkward size, could contribute to such problems as carpal tunnel syndrome of the wrist, which further defines ergonomic problems with respect to the disadvantages of such heavy fluid products as related to the U.S. Pat. No. 5,792,126 reference. U.S. Pat. No. 5,960,837 to Cude et. al., discloses a suction canister and lid combination whereby only destructive force will separate the parts. This renders this invention a disposable product which is costly whereby each time a canister is used, another purchase is made by the customer, and another product enters internal distribution increasing cost cycles and increasing inventory handling costs and another piece of garbage enters the waste stream which is a serious disadvantage. This makes the system expensive, and requires ongoing internal distribution, requiring ongoing inventory space, which is at a premium in most institutions. Another disadvantage is the lack of choice for the customer to re-process, re-sterilize, or re-use, of which options are beneficial, but not available with the U.S. Pat. No. 5,960,837 reference. U.S. Pat. No. 5,901,717 to Dunn et. al., discloses a canister and flushing system. This system comprises complex equipment for handling a collection canister. The disadvantages to this system are expensive equipment is required, and such complex equipment needs expensive maintenance plus required periodic inspection which increases labor costs associated with its presence. In addition, the equipment must be kept clean, which is additional labor required for daily operations. Other disadvantages include a re-usable canister which requires costly labor for internal processing, re-processing and re-using. In most institutions volume of such collection systems is quite high imposing expensive internal handling and re-use processing costs. The system discloses a disposable flush kit which maintains higher disposable costs along with higher costs associated with internal distribution and inventory handling. U.S. Pat. No. 4,419,093 to Deaton discloses a reusable canister having a disposable lid and liner. This system is delivered in pieces and require subassembly by the customer prior to operation. This requires additional labor, which is costly, and involves the inventory and tracking of a plurality of systems in sets. Often times lids and liners can become separated and when out of numerical matching balance, one cannot be used without the other whereas resulting in an incomplete set and an unusable sub-assembly. This disadvantage complicates the ongoing internal distribution and tracking of the subassembly components, which adds costly labor, inventory management and excess handling. The U.S. Pat. No. 4,419,093 reference also discloses contribution of garbage to the waste stream with each use which is a serious environmental concern.

DESCRIPTION OF THE INVENTION

The present invention provides methods and apparatus for utilizing product transfer/delivery containers which do not embody the self inherent physical capacity to maintain shape under extreme negative vacuum pressures of up to minus one atmospheres. Examples of cost effectively fabricated containers which may not embody the implosion resistant strength/construction needed for suction/vacuum collection, may include plastic delivery containers such as plastic pour bottles and intravenous solution containers. The present invention discloses cost effective solutions for reducing waste, reducing labor, reducing inventory, reducing receiving, reducing internal distribution, reducing inventory, and reducing inventory handling costs, reducing space required to carry inventory, all involved with the collection of waste materials. These achievements are carried out by the instant invention whereby successful suction/vacuum collection may be realized using, in a flexible manner, cost effectively fabricated product solution transfer/delivery containers. This application discloses a collection system that teaches use of product supply containers for removal of waste material and the disposal chain. In particular delivery containers for general distribution/transfer/supply/delivery of pour bottle solutions and intravenous solutions and the like are converted into the waste collection and disposal chain. This application also teaches use of a common container for both the supply and disposal chain. This application also teaches use of containers in inventory for supply/delivery then transforming them for disposal utility. This application teaches the use of a common container for the product transfer and then integrates them into systems for the collection of waste material. This application teaches waste reduction methods by integrating delivery container fabrication and the collecting and disposing of waste materials of waste material with a cycling technique. This application teaches the waste reduction methods by using manufacturing methods such as blow molding, and blow fill seal container fabrication, and intravenous solution container manufacturing methods for delivery and disposal purposes transforming the container, which is derived from a delivery mode, from product transfer, and converting to collection of waste materials. The invention(s) of the instant case provide container utility options for the transfer of products, consumption of products and for waste collection options. The invention of the instant case discloses the utilization of product transfer containers, such as pour bottles and intravenous solution containers (bags)(and/or other product containing enclosures used for IV therapeutics and administration of anesthetic agents as well as other agents) for the receiving, collecting and containment and disposal of waste. Using product distribution/transfer containers, also for the handling of waste, results in optimal reduction of waste, reduction of inventory, reduction in labor, reduction of internal inventory distribution, and reduction of inventory and waste disposal costs because the need for separate disposal containers is reduced. The question arises, why pay for a disposal container when a delivery container can be derived from the supply side and converted into a disposal container. Such containers are supplied clean and well suited, within the scope of the instant invention for conversion/transformation into disposal containers. The instant invention confers options allowing consumer choices for the reduction of waste. Plastic transfer containers are commonly used for the distribution/transfer of sterile liquids and other products, such as sterile water, sterile sodium chloride irrigation solution, intravenous solutions for IV therapeutics, other solutions, and the like. These solutions are used for intravenous therapeutics, administration of anesthesia, wound irrigation, irrigation for arthroscopic/endoscopic procedures, urology procedures and many other types of uses. The inventor of the instant case names additional fluent material delivered in polypropylene and or polyethylene polyvinyl chloride containers which are generally high volume supplies in and/or engage the supply chain on a just in time basis for delivery/consumption. Intravenous solution containers (IV bags) are also used for the distribution/commercialization of container products. It is understood the disclosed teachings are not limited to sterile distribution/commercialization product transfer containers. Other product transfer containers may be suitably integrated with the inventions concept to function in a disposal and waste reduction capacity. Other containers, such as prep solution containers, alcohol containers, solvents, and cleaning solutions may function suitably within the scope of the present invention. The teachings are not intended to limit the novel concept of waste reduction to any particular type of product distribution/commercialization transfer container. Other product containers may also be used in the instant invention. These "product" delivery containers are commercialized/distributed to the customer having volumes sufficient enough to provide cubic capacity in substantial proportion for the collection and disposal waste materials. The instant invention(s) reduces the amount of plastic introduced into the waste stream. The instant invention reduces the re-cycling, reprocessing, and labor associated with handling and re-use procedures thereby lowering the associated costs of the waste collection/disposal processes. Collecting fluent waste materials in converted delivery containers such as a pour bottles and intravenous solution containers which have been cost effectively fabricated without implosion resistant strength/construction, provides various solutions/options solving the disadvantages/problems of such prior art containers when the methods and apparatus of the present invention are utilized. When the methods and apparatus embodied by the teachings of the present invention are utilized, the instant invention also provides solutions for reducing the handling and reducing labor, and reducing the costly processes of re-cycling, reusing, reprocessing, sterilizing and/or re-sterilizing. Certain product delivery/transfer containers are fabricated, commercialized and already present or in the supply/distribution chain and or in the consumer facility. The present invention conveniently and easily transforms, converts and integrates these transfer delivery containers for transformation into waste materials collection vessels creating a new type of environmental cycle. We refer to this new/novel cycle as a Techni-cycle. Therefore, Techni-cycling defines a new methods and apparatus of using technique to cycle containers from the delivery side of consumption to the disposal side of consumption for environmental purposes. In essence, Techni-cycling defines the novel process of converting a delivery container into a waste receptacle. In essence, Techni-cycling is also defined by deriving waste receptacles from incoming delivery supplies. In essence, Techni-cycling is defined by transforming delivery containers into disposal containers. In essence, Techni-cycling is an environmental conversion and transformation method. In essence, Techni-cycling confers the options and advantages as disclosed in the instant application. In essence, Techni-cycling is the environmentally preferred method. In essence, Techni-cycling is environmental, among other things. Difficulties exist with the use of the certain pour bottles when integrated in a high negative pressure vacuum collection system. Difficulties also exist with the use of intravenous solution containers when integrated in a high negative vacuum system as commonly used in suction/vacuum collection of surgical waste materials. Negative vacuum draw pressure, at times up to −1 atmospheric pressure is common for drawing surgical waste materials from a surgical site into collection receptacles. One problem is that the common pour bottles are cost effectively manufactured with relatively thin plastic walls sometimes down to the range of 0.025 inches thick, or less and generally made with plasticized materials such as high density polyethylene, polypropylene, polyvinyl chloride, or other like materials. Thin walled containers are commonly fabricated to reduce the plastic material mass (volume of plastic material per unit) and hold down production costs, and shipping weight. It is common practice in container manufacturing to consume the minimum amount of material used per unit to fabricate each container yet maintain end user function for cost effective manufacturing purposes. Common container material durometers, comprising containers having such ranges of thin wall thickness in these like materials, are not generally strong enough to withstand the negative differential pressure of up to −1 atmosphere found in a suction vacuum system, without imploding and/or deforming. Product distribution/transfer containers are commonly fabricated using manufacturing processes know by artisans skilled in the arts of blow molding, and/or blow fill seal manufacturing and the process of thermally laminating sheets and forming cavities for the filling and the production of intravenous solution containers. These containers are fabricated open top or closed top. A solution to the problem of bottle deformity which occurs under high negative implosion pressure is to connect the pour bottle to a suction collection system whereby the pour bottle wall is interposed, between its inner chamber and an outer interspace, each space subjected to a common draw force, the force enveloped over itself on the container inside and outside, the which forms opposing differential pressures providing wall reinforcing balances by effecting a positive and negative neutral force on the bottle wall balancing negative implosion forces. This is carried out by the container and canister co-acting to contain and balance forces in the composite draw path. This addresses the issue of bottle deformity.

The instant invention discloses the neck of a pour bottle as a utilitarian area of the bottle for coupling with a canister system. The instant invention discloses a throat space aperture (pour spout) of a plastic pour bottle as a utilitarian area for engagement of a draw force. The instant invention discloses the throat space aperture (pour spout) as a utilitarian area for coupling of a throat aperture plug. The instant invention discloses a positive and negative pressure exchange plug for providing communication between the draw force and the inside and outside of a transfer container. The instant invention discloses locating an atmospheric pressure draw exchange at the neck area of a transfer container. The present invention discloses interposing the neck (pour spout) of a product transfer/delivery bottle for conversion circumferentially between an throat/aperture plug and a canister lid/cover. In an alternative embodiment a bottle neck cap is interposed between a bottle neck and a canister lid/cover. In still a further embodiment a downward projecting hollow boss is interposed circumferentially between a bottle neck and a force exchange plug. The present invention discloses fabricating a blow molded container for transformation/conversion and bayonet coupling to a canister system. It is understood that that the invention is not intended to be limited to bottle neck configurations which are round. Any shaped bottle neck/lid-cover, cap, plug, boss configuration suitable for arrangement/construction having structuration to carry out the utility of the present invention may be fabricated to carry our the purposes of the instant case. The present invention discloses positioning the plastic bottle throat space in a pressure draw system whereby an in-drawn force is disposed to transfer and deposit medical waste materials into the bottle and an out-drawn force is disposed to transfer the differential draw forces. The present invention utilizes the inner chamber of a plastic pour bottle as a part of the pressure draw communication system. The present invention discloses several embodiments % for carrying out the invention. In one embodiment a bottle cap is shown guiding the exchanging forces in a position along a force draw path at a location between a site of waste material (surgical site) and a source from which the draw forces emanate. The cap is connectable to a lid/cover which attaches to a canister body. In a second embodiment a bottle neck is circumferentially (not necessarily meaning round) interposed between a lid (second embodiment) and a throat spacer (pressure exchanger), whereby the throat spacer is disposed in guiding position to exchange forces along a draw path at a location between a site of waste material (surgical site/other source) and a source from which draw forces emanate. In another embodiment a downward directing hollow lid boss is fitted into a bottle throat and the lid boss is circumferentially (not necessarily meaning round) interposed between a bottle neck and a hollow lid boss transfer plug. The lid aperture spacer is disposed to guide and exchange differential draw forces along a force draw path at a location between a site of material waste (surgical site) and a source from which the draw forces emanate. In another embodiment a plastic pour bottle comprises a neck area comprising winged locking lugs formed unitary with the bottle and disposed to connect to a canister lid embodiment by bayonet motion. Throat/aperture spacers may then be placed in the throat space of the plastic bottle in a position to guide exchange forces along a draw path at a location between a source of waste material (surgical site/other source) and a source from which the draw force emanates. The inventor/author knows of no prior art which anticipates the proximate function and/or provides the utility of the present invention disclosed in this patent application.

PURPOSE OF THE INVENTION

One object of the invention is to position a liquid transfer container upstream to a patient delivery sequence and then place the container downstream to the flow of drawn waste material. Another object of the invention is to invert a liquid container effecting egress of the liquid and the positioning the containing in flow confining connection downstream to a source of waste material. Another object of the invention is to pour solution from a pour bottle and place the bottle downstream in vacuum draw path connection to a suction wand. Another object of the invention is to position a liquid transfer container upstream to and in vascular access with a patient and then position the transfer container downstream to a health care patient in flow control composite connection with a vacuum draw path. Another object of the invention is to provide supply chain efficiency whereby the dispensing container is the receiving container. Another object of the invention is to provide waste reducing process whereby the egress of a container upstream from a health care patient is the same container positioned down stream in flow control association with a draw force. Another object of the invention is to provide practice step for internal container handling including a) taking a transfer container, b) extending a draw path between a vacuum source and a suction wand, c) connecting a delivery container t the path, D) depositing waste material into the container. Another object of the invention is to provide methods and apparatus including a) transferring a liquid product container for health care consumption, b) consuming at least a portion of the product, c) converting the container into a vacuum collection system, d) disposing waste into the container, e) removing the waste in the container. Another object of the invention includes a supply and disposal method comprising, a) manufacturing a container for the distribution of a liquid product, b) distributing the liquid, c) consuming at least a portion of the liquid product, d) directing a draw force to the container, e) depositing waste material into the container. Another object of the invention provide a method for reducing supplies comprising, a) providing a container fabricated for the delivery of a product, b) delivering the product, c) connecting the container to a vacuum source system, d) drawing waste material into the container, e) removing the waste material in the container. Another object of the invention is to provide a method for reducing waste comprising a) transforming a waste receptacle from a delivery container, b) connecting the container to a composite waste draw conduit, c) depositing waste material in the container, d) removing the container from the draw path, e) converting another delivery container into a waste receptacle comprising transformation of a supply container into a waste container. Another object of the invention include providing the methods and apparatus for transforming a plurality of supply containers into a plurality of waste containers. Another object of the invention is to enclose a plurality of supply containers, having been transferred into a plurality of collection containers within a single enclosure. Another object of the inventions to provide methods for transforming supplies into waste receptacles comprising a) taking a delivery container, b) extending a draw path between a vacuum source and a suction wand, c) connecting a delivery container to the path, d) depositing waste material into the container. Another object of the invention is to provide methods for deriving waste receptacles from supply dispensers including a) providing a liquid product in a selectively connectable waste receptacle, b) disposing the receptacle in a vacuum collection canister system, drawing force along a composite path between force and waste, d) depositing waste in the delivery receptacle, An object of the aforementioned objects of the invention of the instant case comprises a) positioning a transfer container upstream in the flow of patient care sequence for liquid dispensing mode, b) positing the container downstream in the flow of patient care in a receiving mode. An object of the immediately recited multiple dependent object of the invention wherein the dispenser is the receiver. An object of the immediately recited two multiple dependent invention objects wherein the dispenser is positioned on the clean side of patient care flow, and the receiver is positioned on the dirty side of patient care flow, and the receiver is in connective structuration with either a gravity flow system of a vacuum draw force. Another object of the invention is to provide methods and apparatus for drawing a negative pressure within a transfer container. Another object of the invention is to provide methods and apparatus in structuration with a draw force including a) providing a liquid product in a selectively connectable waste receptacle, b) disposing the receptacle in a vacuum collection canister system, c) drawing a force along a composite path between a source and waste, d) depositing the waste into the delivery receptacle. Another object is to transform a delivery container into a disposal container. One object of the invention is to provide connect ability between a transfer container and a vacuum collection collection canister lid. Another object of the invention is to provide a composite negative atmosphere draw path formed at least in part by the interior of a transfer container. Another object of the invention is to provide a draw force directed by a draw path in part co-acting to transform a delivery container to dispose waste material. Another object of the invention is to provide a canister in structuration with a supply transfer container forming at least in portion of a composite draw path interposed between a vacuum source and a site of material waste. Another object of the invention is to combine in association with the novel features a negative draw path with a material flow path. Another object of the invention is to combine the draw path with the material draw path to dispose material into a transfer container to remove waste material from a site. Another object of the invention is to provide a throat aperture space plug/seal disposed in a transfer container access site forming at least a part of the draw path controlling draw force to and from a transfer container. Another object of the invention is to provide a receptacle derived from a health care delivery sequence converted to co-act with a canister, a lid, a force, a composite path and a throat/aperture access plug to dispose waste. Another aspect of the invention is to provide supply chain efficiency methods comprising a, fabricating a liquid delivery container, b) transferring the liquid to a delivery site, c) connecting the container in structuration with a waste collection system, d) collecting waste. Another aspect of the invention is to provide supply chain efficiency methods comprising a) manufacturing a container for the distribution of a liquid product, b) distributing the product, c) consuming at least a portion of the product, d) directing a draw force to the container, e) disposing waste in the container. Another object of the invention. One object of the invention is to fabricate a delivery container for disposal and coupling to a waste collection system. Another object of the invention is to provide a method of reducing waste comprising a) fabricating a delivery container, b) connecting the container along a vacuum draw path, c) drawing waste material into the container.

Another object of the invention is to provide a method of collecting supplies and transforming them into waste receptacles comprising, a) collecting delivery supply containers, b) placing the containers positioned to receive waste in vacuum canisters, c) drawing vacuum, d) controlling the draw force to direct waste material for disposing waste into the transfer container. Another object of the invention is to provide a method of converting containers having dispensed at least some container contents, b) converting the container into a vacuum collection system receptive to waste collection and/or removal and or disposal. Another object of the aforementioned objects of the instant invention is to provide a method of handling a dispenser and a receive wherein the dispenser is the receiver. Another objective of the invention is to provide a delivery and collection container system using bottles fabricated from a blow molding process. Another object of the invention is to provide a delivery and collection container fabricated from a blow fill seal manufacturing process. Another object of the invention is to provide a suction/vacuum system which renders product distribution/transfer containers receptive to waste materials. Another object of the invention is to provide a collection system for reducing waste that is derived from a product delivery. Still a further purpose of the invention is to provide container options for reducing the amount of material waste introduced to the waste stream in the medical field. Another object of the invention is to deposit waste materials into a container derived from the product transfer distribution/commercialization cycle and converted into a waste receptacle. Another object of the invention is to use intravenous solution containers as converted receptacles for waste materials. Another object of the invention is to use pour bottles and convert them as receptacles for waste materials. Another object of the invention is to fabricate a waste reducing system which conveys waste reduction options. Another purpose of the invention is to reduce the internal distribution, the inventory management of surgical waste collection devices. Another purpose of the invention is to provide methods and apparatus effecting the utility of reducing handling associated with the collection of surgical material waste. A further purpose of the invention is to provide methods and apparatus to reduce re-cycling, re-processing, and re-use procedures. Still a further object of the invention is to fabricate systems which utilize the cubic space capacity embodied in product distribution, delivery and transfer containers such as pour bottles and intravenous solution containers for waste collection and disposal. Yet another object of the invention is to provide methods and apparatus for the consumer to account for cubic volumes of incoming fluids and cubic volumes of outgoing waste materials for cost effectiveness and better supply planning and purchasing. And still a further object of the invention is to provide methods and apparatus in a system that provides cost effective container conversion and transformation procedure, supply planning, ordering, inventory carrying, procedure supply selection and supply utility. Yet another object of the invention is to provide more cost effective means for collecting surgical waste materials. Still a further object of the invention is to interpose the inner chamber of a plastic pour bottle along a draw path at a location between a material waste source (surgical site) and a source from which the draw force emanates. Still a further object of the invention is to provide a suction collection system fabricated to connect to a pour bottle. Still a further object of the invention is to provide a suction/vacuum system to connect to an intravenous solution container. Still a further object of the invention is to fabricate a blow molded bottle to fit to a suction canister system by a bayonet movement. Still a further object of the invention is to provide a blow molded container comprising a neck structuration for coupling to a lid/cover boss. Still a further object of the invention is to integrate the inside of a distribution/commercialization product transfer container into the vacuum/suction draw control path for reception of waste materials. Still a further object of the invention is to reinforce the walls of a product distribution/commercialization using a vacuum/suction force. Still a further object of the invention is to interpose a transfer container along an intermediate portion of a draw control path between a vacuum/suction source and a source of waste material. Still a further object of the invention is deposit waste materials into a product distribution/commercialization transfer container by a draw force. Still a further object of the invention is to couple a canister cover to a product distribution/transfer container. Still a further object of the invention is to fabricate a product transfer container to couple to a canister cover. Still a further object of the invention is to fabricate a container and a canister cover to couple together. Yet another object of the invention is to provide for container Techni-cycling (as defined above)

b) It is also the intent of the instant invention to satisfy certain scenarios encountered in the sequences involving supply chain product handling. One scenario is provide an overfill connection communication such as tubing 16 interposed between space 24 and space 28. This scenario is provided-when personnel is occupied when the transfer container space fills and switching of containers is not convenient. This however may be dealt with by the serially connecting of container such that when one container if full the vacuums draw has been previously linked to draw into the next container rather than overfill into the canister housing.

BRIEF DESCRIPTION OF THE DRAWINGS

FIG. 6 is a top plan view showing the assembly of FIGS. 1 through 5c. FIG. 6 also shows a rectangular cutout that relates to Sheet 19 and FIG. 8a of Sheet 8 which relates to the view according the details of Sheet 21.

FIG. 6a is a blow up detail W which shows detail relative to what is shown in connected circle in partial cross section of FIG. 6c. FIG. 6a is a blow up cross section of variable purpose quad plug/cap site wherein the substantial length of the port structure connection site is sunken deep to the top surface of lid 10.

FIG. 6b is a blow up detail Y as it relates to what is shown in connected circle of partial cross section FIG. 6c. FIG. 6b shows a partial blow up cross section of container cap 8 nested within quad cap/plug cap plug/nest 12b. Fenestration plug/nest 12b nests cap 8 while disposed in sunken recessed space 10a1 of lid 10 wherein a substantial portion of 12b and container cap 8 rests deep to the top of surface of lid 10.

FIG. 6c is a partial cross section taken along line AA of FIG. 6. This partial cross section was take to show detail of previously described detail W of FIG. 6a and detail Y of FIG. 6b.

FIG. 7 is a top perspective view of a canister housing. Such housings are generally transparent so that viewing of the inside of the canister and the volumetric fill activity of the interior of the canister may be easily viewed. In the instant case it is important that he general volumetric fill of the product transfer container disposed inside the canister is easily viewed.

FIG. 7a is a top plan view of canister housing 7, 7a, 7b, 7c, 7d, & 7e.

FIG. 7b is a side elevation cross section of canister 7a, 7b, 7c, 7d, 7e, taken along lines UU of FIG. 7a.

FIG. 7c is a partial blow up detail of the connected circle of canister rim as shown in FIG. 7b.

FIG. 8 is a top perspective view of canister lid 10.

FIG. 8a is a bottom plan view of lid 10.

FIG. 8b is a top plan of lid 10.

FIG. 8c is a cross sectional view of lid 10 taken along lines AA of FIG. 8b.

FIG. 8d is a partial cross sectional blow up detail of connected circle of FIG. 8c.

FIG. 8e is a partial cross sectional blow up detail of connected circle portion of FIG. 8c.

FIG. 8f is a top plan view of canister lid 10.

FIG. 8g is a partial blow up detail of the connected circle of FIG. 8f.

FIG. 8h is a side elevation view of canister lid 10.

FIG. 8i is a blow up detail of connected circle portion of FIG. 8h.

FIG. 8j is a front elevation view of canister lid 10.

FIG. 8k is a partial blow up detail of the connected circle of portion of FIG. 8j.

FIG. 9 is a top perspective view of the connected variable plug/cap quad set and sized and shaped to interact with various scenarios involved with the distribution and disposal of fluent materials whereby the dispenser is the receiver and when receptive, the product transfer container is sealably disposed within the collection system.

FIG. 9a is a blow up detail showing a transfer container cap nesting struts as shown in connected circle view of FIG. 9.

FIG. 9b is a top plan view of variably sized and shaped physical and functional plug/cap quad.

FIG. 9c is a top plan blow up detail of connected circle view of FIG. 9b wherein the bottle cap nest and fenestration plug.

FIG. 9d is a cross section of two operational sections of FIG. 9b taken at section line AD.

FIG. 9e is a bottom plan view of multi-function plug/cap connectors.

FIG. 10 is an isometric view of a moment lever 11 when connected to lever axis socket 10e at 11d operates to swing jack 11a and hook 11c to circumvent canister rim 7e.

FIG. 10a is a front elevation view of lever 11 showing lever moment distance 1, lever moment distance 2 and lever moment distance 3. Each of the 3 moment lever distances are take relative to a central pivot axis point of 11d. View 10a corresponds with moment lever arm position as it relates generally to FIG. 10e, FIG. 15c, FIG. 16f FIG. 17f FIG. 18f.

FIG. 10b is a front elevation view of moment lever 11. Each of distances moment lever 1, moment lever 2, moment 3 of FIG. 10b are take relative to the central pivot point along 11d.

FIG. 10c is a side elevation view of moment lever 11 showing point 11e, jack 11a and hook 11c of a maximum distraction distance as depicted by the three arrows and the three statements delta 11e at D-90. FIG. 1c shows moment lever 11n a vertical position at D-90 operational position. This 90 degree operational position relates to FIG. 10g, FIG. 14, FIG. 15, FIG. 16c, FIG. 17c and FIG. 18c. Moment lever 11 is also shown in this vertical 90-D position in FIG. 20. FIG. 21, FIG. 21a FIG. 21b.

FIG. 10d shows a partial detail blow up relative to connected circle of FIG. 10c.

FIG. 10e is a side elevation of lever 11 showing delta 11a at D-0. This position is of moment lever 11 shows jack 11a up and hook 1c down and relates to minimum distraction distance 11a at position D-0 which corresponds to FIG. 14, FIG. 15, and more particularly FIG. 15c, FIG. 16F, FIG. 17f, FIG. 18f. Moment lever f is shown in this position also in FIG. 20a, FIG. 21, FIG. 21a, FIG. 21b, FIG. 20b, FIG. 22a, FIG. 22, FIG. 22b, FIG. 23, FIG. 23a.

FIG. 10f is a partial blow up detail of connected circle portion of FIG. 10e.

FIG. 10g is a side elevation view of moment lever 11 wherein distraction differential delta when lever 11 is in a vertical 90-D position.

FIG. 10h is partial blow up detail of connected circle portion of FIG. 10g.

FIG. 10i is a side elevation view of moment 11 showing seal jack in a down position with seal hooks in an up position and delta distance 11b at minimum distraction distance delta at position 180 D.

FIG. 10j is a blow up detail of connected circle portion of FIG. 10i.

FIG. 11 is a top perspective view of a bottle seal and bottle throat aperture pressure transfer plug.

FIG. 11a is a top plan view of the bottle/seal throat aperture plug of FIG. 11.

FIG. 11b is a cross sectional view of bottle neck seal and throat pressure transfer plug taken at lines M of FIG. 11a.

FIG. 11c is a top perspective view of bottle seal throat aperture transfer plug 9 in physical connection with patient suction tubing 19a and transfer elbow 17 and air filter 15.

FIG. 11d is a top plan view of sub-assembly of FIG. 11c.

FIG. 11e is a side elevation cross sectional view of FIG. 11d taken at line L.

FIG. 12 is a top perspective view of a seal which attached to the bottom ring 10q of lid 10 as shown in FIG. 8d.

FIG. 12a is a side elevation view of the seal shown in FIG. 12.

FIG. 12b is a cross sectional view of seal 13 taken at line G of FIG. 12a.

FIG. 12c is a partial cross sectional blow up detail of connected circular portion of FIG. 12b.

FIG. 12d is a top plan view of the seal shown in FIG. 12.

FIG. 12e is a bottom plan view of seal 13 as shown in FIG. 12.

FIG. 13 is a top perspective of an adapter 21 which may form and physical and functional seal between lid 10 and a canister sizes and shaped to sealably engage adapter 21.

FIG. 13a is a side elevation view of adapter 21 of FIG. 13.

FIG. 13b is a cross sectional view taken at line H of FIG. 13a.

FIG. 13c is a partial blow up detail of the adapter rim of connected circle portion of FIG. 13b.

FIG. 13d is a top plan view of adapter 21 as shown in FIG. 13.

FIG. 16 shows a partial blow up detail of box portion of FIG. 8 on sheet 9. FIG. 16 shows lever 11a D-180.

FIG. 16a is the same partial blow up detail of FIG. 16 showing moment lever 11 at D-150.

FIG. 16b shows the same partial blow up detail of FIG. 16 depicting moment lever 11 at D120.

FIG. 16c shows the same partial blow up detail of FIG. 16 showing lever 11 at D90.

FIG. 16d shows the same partial blow up detail of FIG. 16 showing lever 11 at D60.

FIG. 16e shows the same partial blow up detail of FIG. 16 showing lever 11 at D30.

FIG. 16f shows the same partial blow up detail as FIG. 16 showing lever 11 at D0.

FIG. 17 is a partial blow up detail of the rectangular portion of FIG. 14 showing lever 11 at D180.

FIG. 17a is the same partial blow up detail as in FIG. 17 showing lever 11 at Dl 50.

FIG. 17b is the same partial blow up detail as FIG. 17 showing lever 11 at Dl 20.

FIG. 17c is the same partial blow up detail as FIG. 17 showing lever 11 at D90.

FIG. 17d is the same partial blow up detail as FIG. 17 showing lever 11 at D60.

FIG. 17e is the same partial blow up detail as FIG. 17 showing lever 11 at D30.

FIG. 17f is the same partial blow up detail as FIG. 17 showing lever 11 at D0.

FIG. 18 is partial blow up detail of the bottom plan view of FIG. 8a detailing the rectangular portion showing lever 11 at Dl 80.

FIG. 18a is the same partial blow up detail as FIG. 18 showing lever 11 at D150.

FIG. 18b is the same partial blow up detail as FIG. 18 showing lever 11 at D120.

FIG. 18c is the same partial blow up detail as FIG. 18 showing lever 11 at D90.

FIG. 18d is the same partial blow up detail as FIG. 18 showing lever 11 at D60.

FIG. 18e is the same partial blow up detail as FIG. 18 showing lever 11 at D30.

FIG. 18f is the same partial blow up detail as FIG. 18 showing lever 11 at D0.

FIG. 19 is a side elevation view of a product transfer container and cap.

FIG. 19a is a partial cross section of FIG. 19 taken and AH showing the transfer container having disposed within its neck, aperture plug 9 and having cap 8 thereon secured for disposal of enclosed material waste post collection.

FIG. 19b is a cross section of cap 8, bottle neck aperture plug 9 and a product transfer container having its cap removed therefrom.

FIG. 20 shows a top perspective view of a liquid transfer container having waste material disposed therein after collection and having been receptive to the collection of waste material. The locking and sealing between lid 10 and canister 7 is maintained by first, second, third and fourth snap down locks 10i turned down and remaining in integral contact with lid 10 by a living hinge. Vacuum source tubing 20, patient suction tubing 19, have been removed, elbow 17 has been replaced to cover 10d and cap nest/fenestration plug 12d has been place over fenestration 10a of lid 10.

FIG. 20a is a top plan view of FIG. 20 after elbow 17 and fenestration plug 12d have been moved but prior to first, second, third and fourth snap down locks 10i have been secured, and prior to moment lever 11 having been moved from D0 to D90.

FIG. 20b is a partial side cross sectional view taken at line AJ of FIG. 20a.

FIG. 21 is a partial top perspective view of FIG. 21a.

FIG. 21a is a top plan view of transfer container disposed within the collection system, port structure 12d has been move to cap 10d, port structure plug 12c has been moved to occlude 12a. First, second, third, and fourth snap down locks 10i have been deployed at their living hinge to engage lid 10 to canister 7 at rim 7e and lever 11 has been positioned to 90D.

FIG. 21b is a partial side cross sectional view of FIG. 21a taken at line AL of FIG. 21a.

FIG. 22 demonstrates the versatility of the instant invention wherein suction collections operations may ensue despite the absence of a transfer container.

FIG. 22a is a top plan view of FIG. 22 I a scenario where no transfer container is present.

FIG. 22b is a partial side cross sectional view of FIG. 22a taken at line AN. FIG. 22b depicts a scenario where no liquid product transfer container is present and patient suction tubing 19 is connected to 12a vacuum source tubing 20 is connected to 12d and cap/nest fenestration cap 12b is securely sealed over fenestration 10a. In this scenario material waste flow directly from a source of material waste through patient suction tubing 19 into suction canister space 24 as a result of a negative atmospheric draw emanating from a vacuum draw source through vacuum tubing 20.

FIG. 23 is a partial top perspective view of inverted canister system showing first, second, third & fourth snap down locks 10i securing a sealing engagement between lid 10 and canister 7 at rim 7e and collected waste material may be simultaneously dispensed from both transfer container space 28 and canister space 24 through bottle neck fenestration 10a and fenestration 10c subsequent to removal of plug 12a and 12b and subsequent to inversion of the canister allowing the waste material to be simultaneously dispensed from both said spaces 24 and 28.

FIG. 23a is a tip plan view of container cap and lid configuration as described in FIG. 23.

FIG. 23b is a partial side cross section view taken at line AP of FIG. 23a.

FIG. 24 is a front cross section of a transfer container representing a pour bottle and a vacuum seal physical and functional relationship with a lid which is capable of sealable connection with a threaded pour bottle and a double ported intravenous solution container.

FIG. 24a is a top plan view of FIG. 24.

FIG. 24b is a side perspective view of the pour bottle connected to the lid of FIG. 24 showing an equivalence in incremental marking along the sides of both the liquid transfer container and the canister housing representing substantially equal volumetric fill lever measurements. In this relationship the peripheral dimensions of the liquid transfer container is substantially similar to the peripheral dimensions of the outer canister housing establishing a near equal series of fill level markings on both the transfer container and the canister housing wall.

FIG. 24c is a side elevation of FIG. 24b showing incremental marking along the side of canister housing which are intended to reflect similar volume fill readings as the product transfer container of FIG. 24b.

FIG. 25 is a cross sectional view of an intravenous solution container disposed within a suction canister system which has a lid capable of physical and functional connection to both pour bottles and intravenous solution containers.

FIG. 25a is a top plan view of the embodiments of FIG. 25.

FIG. 25b is side perspective cross sectional view of intravenous solution container connected to a double spike which is unitary and integral with the canister lid.

FIG. 25c is a side elevation view showing incremental markings volume collection measurement indica. This approach for intravenous solution container is similar to the indica marking to the outer canister wall relative to FIG. 1, FIG. 2, FIG. 5, FIG. 5a, FIG. 5b, and FIG. 5c.

DETAILED DESCRIPTION OF THE DRAWINGS

Figure 1:
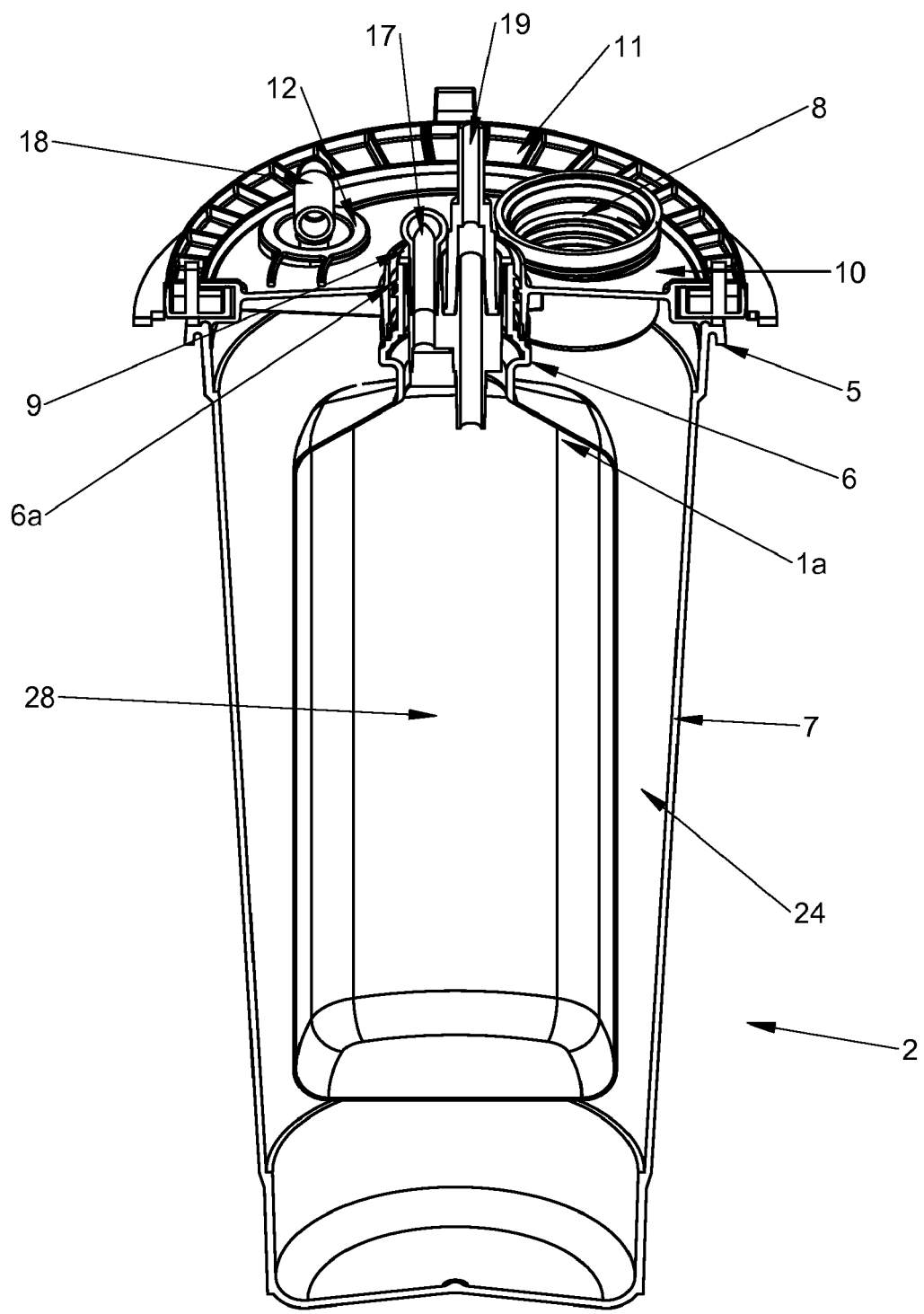
FIG. 1 is a side perspective cross section of the liquid transfer container sealed within a suction collection canister system whereby the liquid transfer container has a volumetric capacity encompassing substantially the majority of the interior of the suction collection canister system.

FIG. 1 shows a side perspective cross sectional view of prime manifold transfer container 1a connected to canister lid 10. Plug 9 is shown secured within the throat aperture space of transfer container 1a. Lid 10 is shown sealed and secured to the top rim of canister 7. Space 28 represents the interior of prime manifold container 1a and space 24 represents the space exterior to the outside wall of prime manifold container 1a and the inside of canister 7 lid 10 and cap plug fenestrations of lid 10. Cap 8 which has been removed from transfer container 1a is shown nested in a space on lid 12 which is substantially sunken to the top surface of lid 10. Lever 11 is shown at D-0. Patient suction tubing 19 is shown connected to prime manifold transfer container throat plug 9 creating flow through communication with space 28 of container 1a. Elbow 17 and elbow 19 are shown connected to plug 9 and port 12a. Not shown is the communication tubing between elbows 17 & 18. Elbows 17 & 18 provide a flow path communication between space 28 through plug 9 through elbow 17 through tubing 16 which is not shown in this FIG. 1 through elbow 18, through lid fenestration 10d and into space 24. This FIG. 1 shows a prime manifold transfer container of a volumetric capacity of substantially 1500 ml sealed within a suction collection system.

Figure 2:
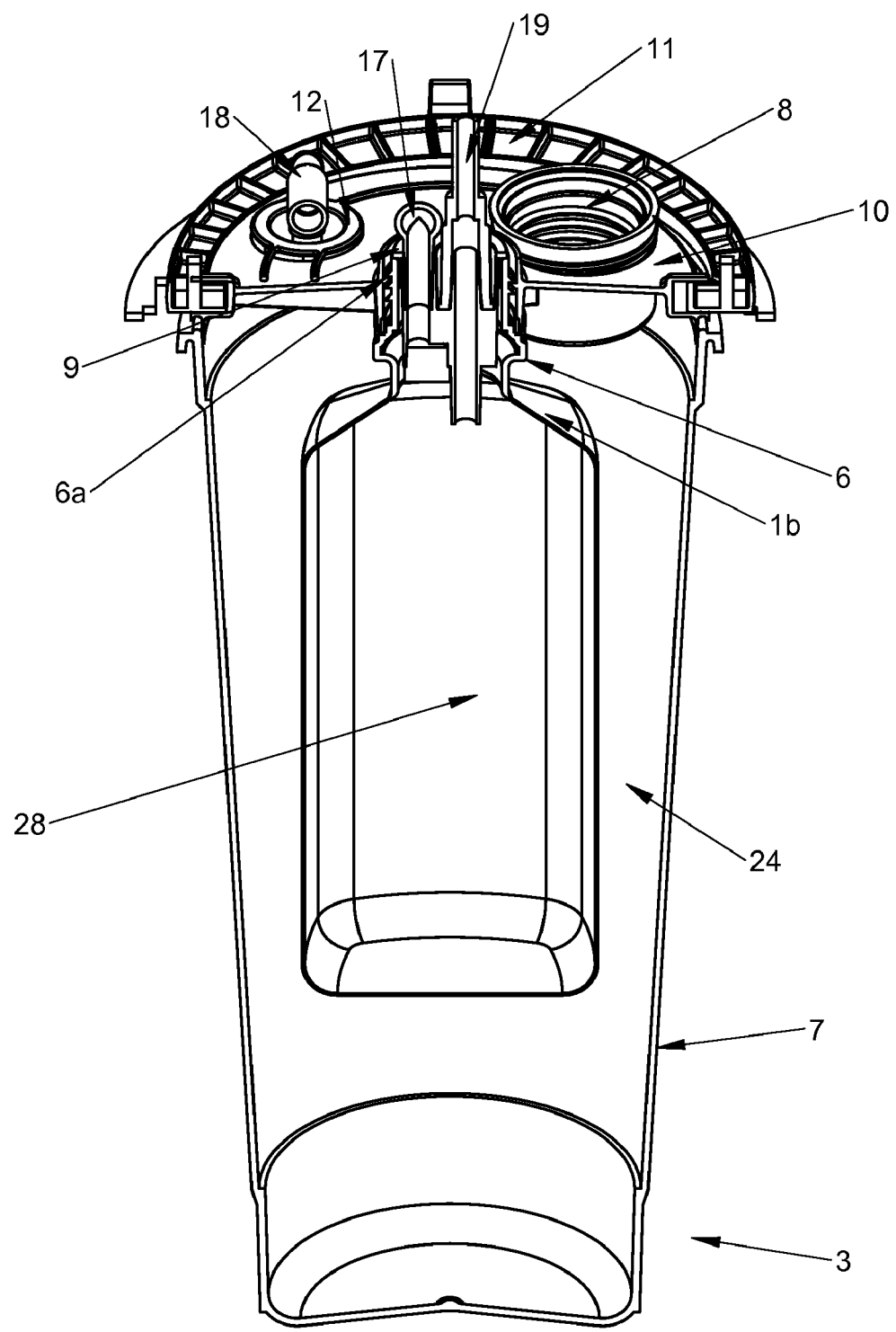
FIG. 2 is a side perspective cross sectional view of a liquid product transfer container sealed within a suction canister collection system whereby the size of the liquid product transfer container has substantially less volumetric capacity tot hat of the transfer container of FIG. 1.

FIG. 2 shows substantially the same physician and functional relationship between a prim manifold transfer container 1b and a waste collection system 3 however in this figure the prime manifold transfer container 1b comprises a volumetric capacity of substantially 1000 ml.

Figure 3:
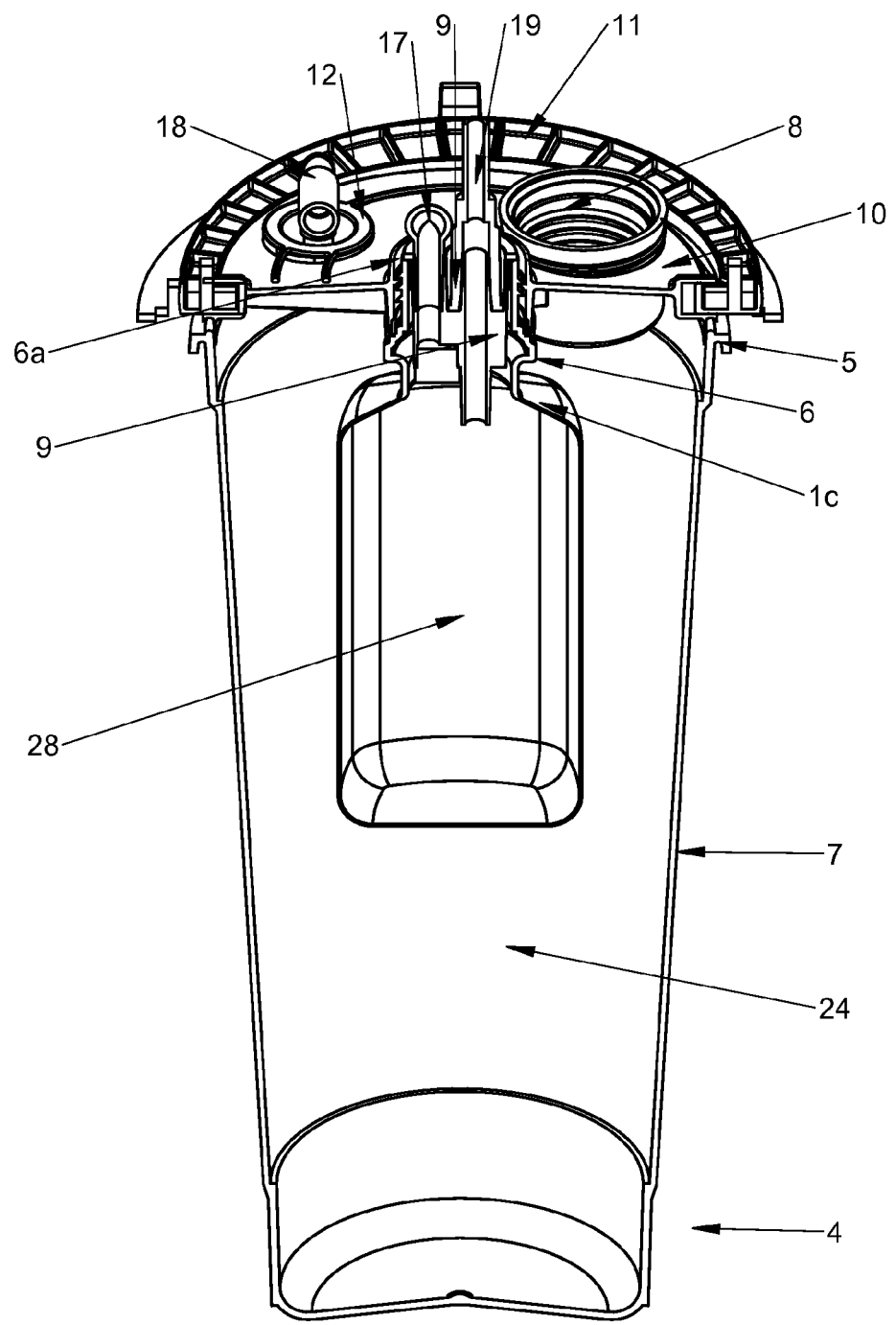
FIG. 3 is a side perspective cross sectional view of a product liquid transfer container sealed in a suction canister collection system where the volumetric capacity of the liquid transfer container substantially smaller that that of the transfer containers shown in cross sections of FIGS. 1 & 2.

FIG. 3 shows a substantially the same physical and functional relationship between a prime manifold container 1c and a waste collection 4, however in this figure the prime manifold transfer container comprises a volumetric capacity of approximately 500 ml.

Figure 4:
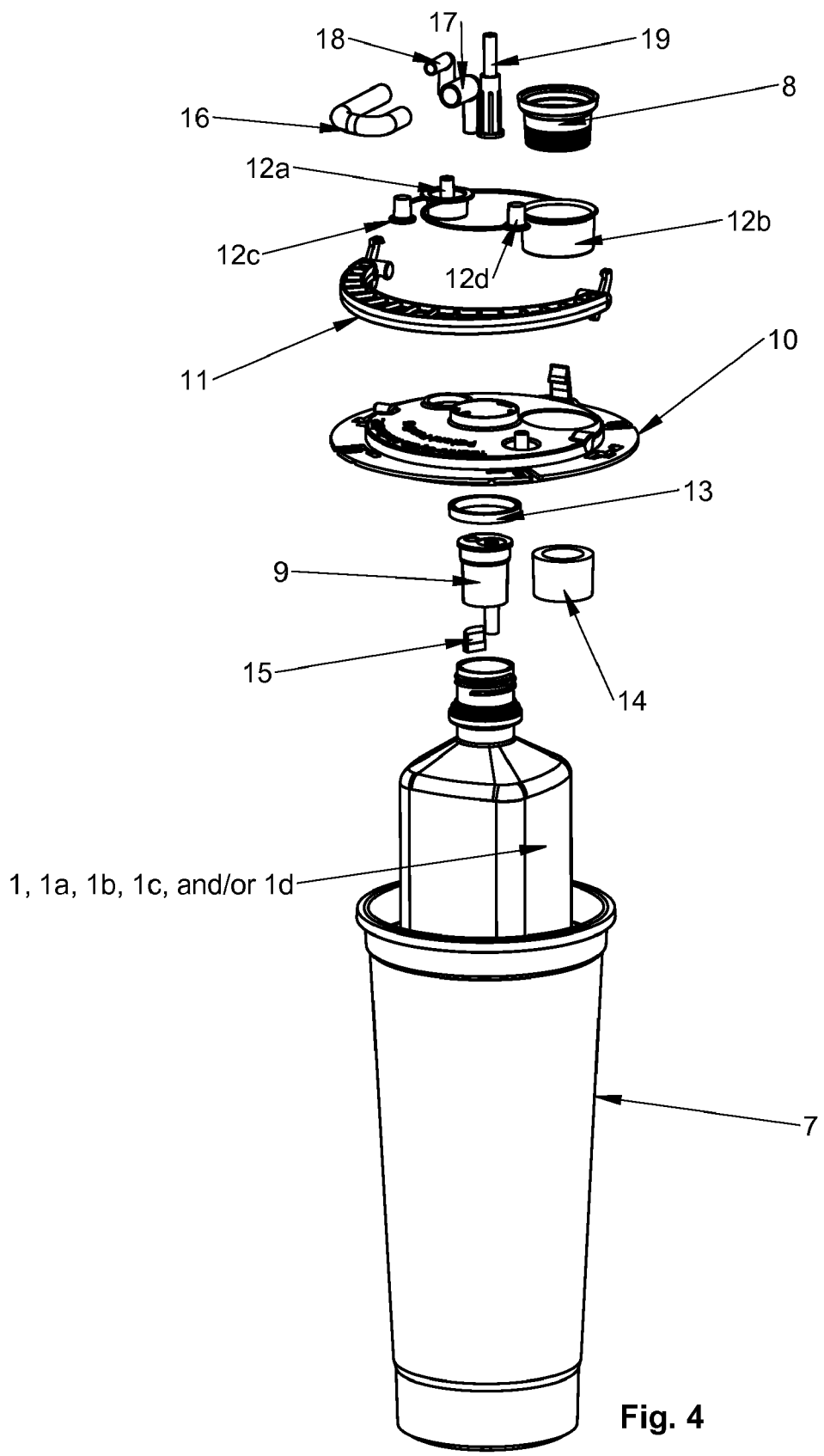
FIG. 4 is a side perspective exploded view of the component parts embodied in FIGS. 1, 2, & 3. Such components are exploded in general physical and functional positional relationship relative to FIGS. 1, 2 & 3 as related to product transfer containers 1, 1a, 1b, 1c 1d, 1e, 1f and container cap 8. Such exploded view related to sealing a product transfer container in a suction collection system.

FIG. 4 is a exploded side perspective view showing canister body 7, prime manifold transfer container 1, 1a, 1b, 1c, 1d, cup filter 14, wedge filter 15, pressure transfer plug 9, seal 13, lid 10, lever 11, plug transfer pressure arrester 12, 12a, 12b, 12c, 12d, spacelink link tubing 16, elbow 18, elbow 17, prime manifold transfer container cap 8, and patient suction tubing 19. Not shown is the vacuum source tubing 20 however this feature is shown in other drawings and figure of this case.

Figure 5:
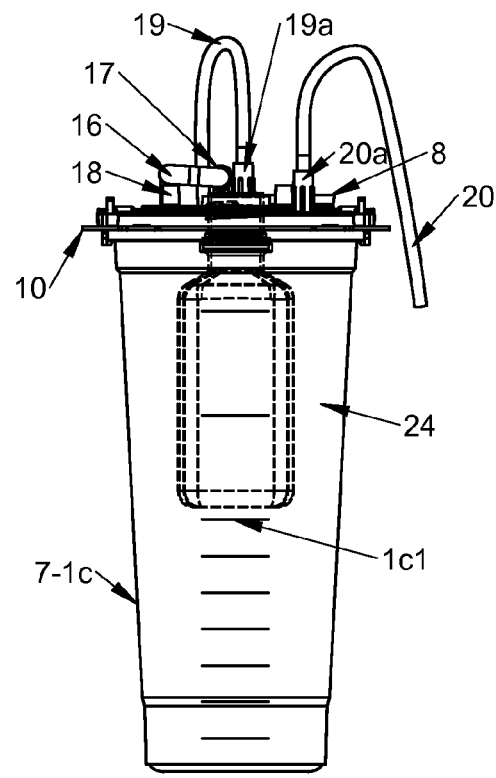
FIG. 5 is a side elevation view which corresponds to the cross section of FIG. 3. The volumetric capacity of container 1c is less that the volumetric capacity of space 24 minus the volumetric capacity of transfer container 1c whereas there is a volumetric differential in that the volume of container 1c is less than the volume of space 24. As shown by horizontal indica/lines visible in association with the exterior wall of the container 7 which represents visually the fill level of the product transfer container as well as the fill level of the container 7 itself. Container 7 is constructed of a transparent material so that the fill levels of the transfer container sealed within the collection system may be visualized from the exterior of container 7. The bottom of container 7 at 1a1 represents a volume capacity which begins at the total volume of the particular product transfer container which would be filled inside the collection system. Incremental volume markings which are shown as horizontal lines in association with the canister wall going up the side wall of the canister represent convenient fluid volume markings which are spaced apart at distances relative to the diameter of the canister and its ensuing wall shape as the canister body wall is shaped to its top. Such incremental markings continue up the side of the canister however at such point where the markings locate the level at which the bottom of the transfer container locate inside the canister, the markings continue up the canister at incremental measurement distance intervals which are impacted by the size and shape of the transfer container. The spacing between incremental markers representing the volume of material collected in both the product transfer container and the canister are represented by the markings along the wall of the canister above the bottom of the transfer container and relate to an increasing volume of collected material subtracting the volume currently held by the size and shape of the transfer container. The spacing of the incremental volume indicia markets going up the side wall of the canister at a location proximal to the level of the transfer container bottom are greater in distance to an extent relative to the volumetric subtraction of the volume of the transfer container relative to its size and shape. The volumetric collection subtraction begins where the transfer container bottom locates respective to the canister wall differentiation in measurement indicia changes to reflect the volume of collected material held in hte transfer container.

FIG. 5 shows a 500 ml prime manifold transfer container sealed within a waste collection system 4 of FIG. 3. In this embodiment a vacuum source draws negative atmospheric pressure on vacuum tube 20 which serially imparts a negative pressure force through tube 20, lid 10 at 20a, within space 25, through lid 10 at elbow 18 through link tubing 16 elbow 17 through plug 9 at 17 within space 28 through plug 9 at 19a through patient suction tubing 19, through a suction wand apparatus to draw material from a source of material into the prime manifold transfer container space 28. Incremental volumetric measurement markings on the outside of container wall 7 in the embodiment of FIG. 5 shows volumetric readings at the bottom of container 7 which begin at a volumetric value of the volume of material containable by space space 28 in prime manifold container 1c. Once prime manifold container 1c is filled with waste material elbow 17, link tubing 16 and elbow 18 provide communication for material waste overflow into canister 7, space 24 of canister 7 fills volumetrically upward to such pint as where the bottom prime manifold transfer container 1c is located. Once the volumetric waste fill extends to a point past the bottom of prime manifold container 1c the volume measurement markings on the outside of canister above the bottom level of transfer container 12c represent a subtraction of the volume of container 1c as the volume of material is drawn and rises up the wall of container 7. In the event there is enough waste material collected in container 1c and space 24 of and canister 7 and the entire 7 is filled, the subtraction value ceases to apply, and the volume of material collected in the system is approximately the volume of canister minus a minimum volume as would be occupied by the material unit mass volume of the transfer container within the collection system, plus any amount of waste volume remains in the connection between elbow 17 & elbow 18.

Figure 5A:
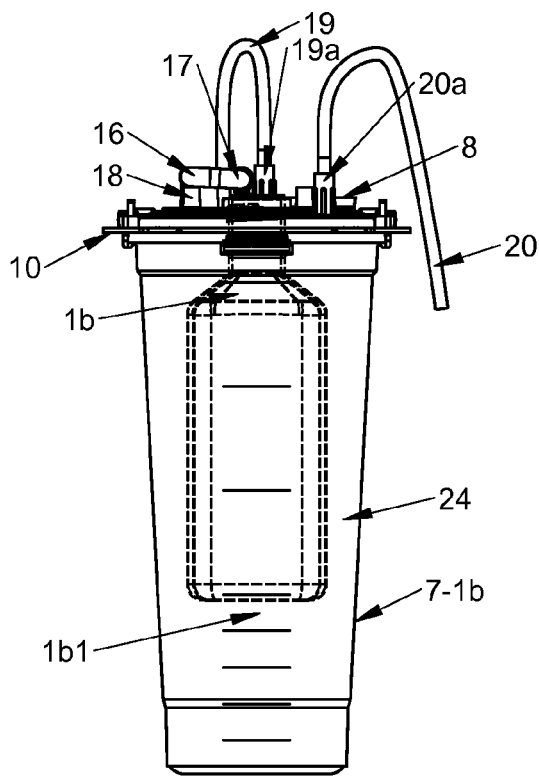
FIG. 5a shows the same indicia and volume measurements approach as FIG. 5 but with a different transfer container.

FIG. 5a represents substantially the same physical functional and functional relationship between the prime manifold transfer container and suction collection system. In this Figure the prime manifold transfer container 1b comprises a volumetric capacity of approximately 1000 ml.

Figure 5B:
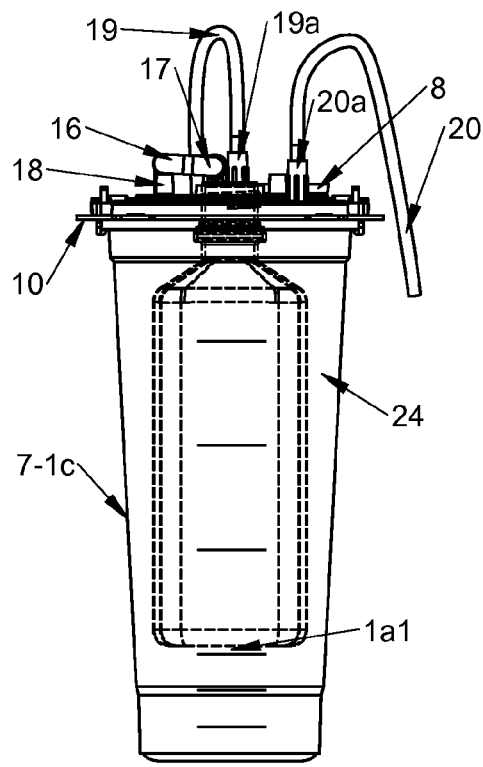
FIG. 5b shows the same indicia and volume measurements approach as FIG. 5 but with a different transfer container.

FIG. 5b shows a prime manifold transfer container showing the substantially the same physician and functional relationship as shown if FIG. 5 however in this FIG. 5b the prime manifold container 1a comprises a volumetric capacity of approximately 1500 ml.

Figure 5C:
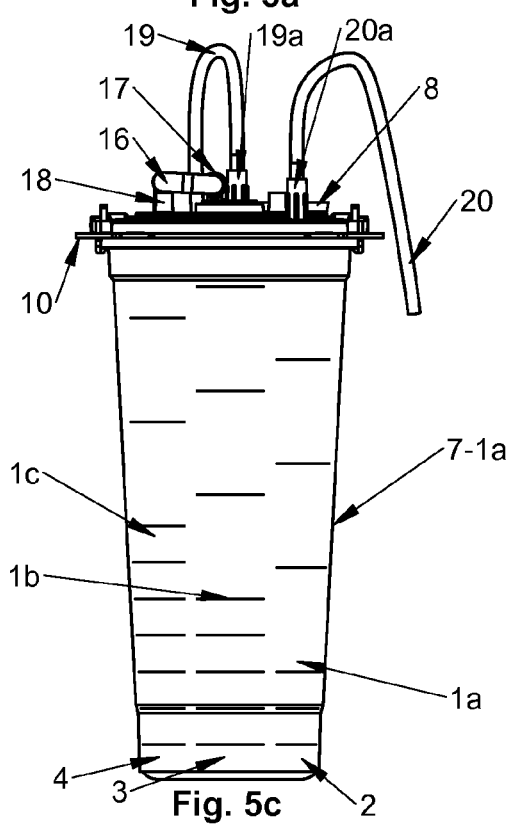
FIG. 5c combines the volume measurement approach of FIGS. 5, 5a & 5b, into the same canister body wall. It is understood that the indicia on the outer canister walls could also include an outline of the transfer container sealed inside the canister, and this embodiment would look much like FIGS. 5, 5a, 5b & 5c however the outline/indicia showing the transfer container inside the canister would be marked on the canister wall. The marking of the canister wall with the outline of the transfer container (and its volumetric indicia) could be such that an individual transfer container could show on the canister wall, or more than one transfer container (plural transfer containers)(and more than one respective volumetric indicia (plural indicia respective to each of the transfer containers)) could show on the canister wall. Several different sized transfer container outlines could show on the container wall to reflect the volumetric relationship between the volume fill inside the transfer container such as in space 28 and the volume fill in canister space 24 the differential volumes as container space 28 space may fill up and overflow into canister space 24 and the addition of the volumetric capacity of container space 28 as it relates to the incremental volume marking of the canister wall below the transfer container as it is sealably disposed within the canister and, subtraction differential of transfer container 28 volume as it impacts the changing distance between incremental markings on the outside of the canister wall relative to the indicia location above the point along which the transfer container therein disposed inside the collection system.

FIG. 5c represents a plural volumetric measurement indicia of a single canister housing wall showing measurement indicia points at 1a, 1b, & 1c, which represents respectively where prime manifold transfer container 1a, 1b, & 1c would be located with respect to canister 7, & 1a housing wall. Along the bottom of the canister is shown at 2, representing the indica marking scenarios as describe in FIG. 5d which relates to FIG. 1 and a 1500 ml container. At the bottom of canister housing at 3 shown indica markings relative to FIG. 5a which is in respect to collection 3 of FIG. 2. Along the bottom of canister housing 4 represents idica markings with respect to FIG. 5 which is also in respect to collection system 4 of FIG. 3.

FIG. 6 is a top plan view of assembled suction collection systems 2 of FIG. 1, 3 of FIG. 2, 4 of FIG. 3 and of FIG. 4, FIG. 5, FIG. 5b, FIG. 5c. Shown in FIG. 6 is lid 10, lever 11, lever latch 10h, plug 9, patient suction tubing port 19, cap 8, cutout rectangular blow up box which refers to sheet 19, vacuum port 10d, plug elbow 17, quad carrier connection elbow 18, link tube 16, quad carrier cap/nest plug 12b, cap 12c, cap 12d. Also shown is quad carrier 12a, rim surface 7d of canister 7 (not shown here).

FIG. 6a is a partial bow up detail representing the structures connected circle of FIG. 6c showing elbow 18 as it connects to 12a and 12a as it connects to fenestration 10c of lid 10.

FIG. 6b is a partial blow up detail representing structures in connected circle of FIG. 6c showing prime manifold transfer container cap 8, fenestration plug 12b, lid 10, and cap/nest recess 10a1 of lid 10.

FIG. 6c is a partial cross section view of previously disclosed detail of FIG. 6a and FIG. 6b. Shown in FIG. 6c is lid 10, rim of canister 7, lever lock latch 10h, elbow 18, cap 8, quad carrier plug 12a, circular path radius seal 10m, canister rim 7e, fenestration lid locating 10c, space 24 and prime manifold transfer container 1, 1a, 1b, 1c, 1d, 1e, & 1f.

FIG. 7 is a top perspective view of prime manifold transfer container 7, 7a, 7b, 7c, 7d, 7e. Shown I this FIG. 7 the inside upper rime of 7b of canister 7 which mates with lid 10, the circular half radius 7c, which mates with lid 10 and peripheral top rim 7d which mates with lid 10. Also shown is secondary diameter 7i of canister 7.

FIG. 7a is a top plan view of canister 7, 7a, 7b, 7c, 7d, 7e.

FIG. 7b is a side cross sectional view of any one of the canister shown in FIG. 7a and FIG. 7. Shown here are lid 10 sealing surfaces 7b, 7c, 7d, and rim portion 7e and 7f. Reduced diameter 7g & 7i are also shown.

FIG. 7c is a partial blow up detail of cross section of connected circle of FIG. 7b. Canister surface 7b mates with lid surface 10n of lid 10, canister surface 7c mates with lid surface 10n, canister surface 7d mates with lid surface 101. The canister surface 7d provides a contact surface for lever jack 11a, canister surface 7e provides a skirt, canister 7f provides and under surface for allowing contact with lever hook 11c and allowing leverage to be imparted between lid 10 & canister 7. Space 7g is provided for injection molding purposes such that the configuration just previously describing the rim detail of canister 7 has substantially even wall thickness. Surface 7i shows a canister rim that represents a descending diameter overall.

FIG. 8 is a to perspective view of lid 10 showing first second, third & fourth snap down locks, lever latch 19h, detent 10a1 for nesting quad carrier 12b and prime manifold transfer container cap 8, first pivot housing 10e1, second pivot housing 10e2, lever distraction ramp 10v, lever distraction ramp 10v-2, jack and hook clearance slot 10v1, jack and hook clearance slot 10b2, lid fenestration 10c, 10a, 10d, thread engagement notches 100, lever latch flexibility space 10h2, lever latch flexibility body 10h3, lever latch hook 10h1, and lever latch connect rod 10h4 and lever latch connect rod 10h5. Also shown is lid 10 sidewall 10j, company logo/name 10t, lid side 10k, lid boss 10a2, living hinge 10u, pivot socket housing 10f, lock down seal latch hook 10w.

FIG. 8a shows a bottom perspective view of lid 10. Rectangle cutout of sheet 21 demonstrates blow detail of the partial blow of view on sheet 21, FIG. 8a shown from the bottom lid fenestration 10a, plural lid strength struts 10g first, second, third and fourth living hinges 10u of first second, third and fourth lock down latches 10*i*. First second, third & fourth lock down latch hooks 10*w* is also shown. Also shown are lid fenestration 10*d*, 10*c* lever hook and latch clearance slots 10*b*1 & 10*b*2 and lever pivot socket housing 10*b*1 & 10*b*2. Also shown from the bottom is hook portion 10*h*1 of lever hook latch 10*h*. Also shown is the bottom side of a prime manifold transfer container cap holder nest holder 10*a*1.

FIG. 8*b* shows substantially the same features as disclosed in FIG. 8 however FIG. 8*b* shows a cross section taken at line AA of of lid 10.

FIG. 8*c* shows a cross section of lid 10 at line AA of FIG. 8*b*. Also shown is cross section taken at lid fenestration 10*a*, lid fenestration 10*d*, bottle cap 8 nest 10*a*1, lever latch 10*h*, lid sealing surface 10*r* and strut 10*g*.

FIG. 8*d* is a partial blow up detail of connected circular cross section of FIG. 8*c* showing plural helically place and spaced thread retaining notch struts, bottom fenestration boss rim 10*q*, top fenestration boss surface 10*a*2, lid 10, top boss surface 10*s* and fenestration 10*a*. Also shown in the background is sunken cap lid & nest detent 10*a*1 of lid 10.

FIG. 8*e* is a partial blow up detail of connected circle cross section of FIG. 8*c* showing lid 10 in its disclosed features, lid sidewall 10*j*, lid side edge 10*k*, lid sealing surface 10*l*, lid circumferential sealing surface 10*m*, and lid side wall surface seal 10*n*, and lid bottom rim 10*r*.

FIG. 8*f* is a top plan view of lid 10 showing many of the detailed features disclosed in FIG. 8 through 8*e* on drawing sheet 8.

FIG. 8*g* is a partial blow up detail of connected circle of FIG. 8*f* showing the roof 10*e*2 of pivot socket 10*f* and detailing the distraction ramp profile depicted at D-180, D-150, D-120, D-90, D-60, D-30, & D-0. Also shown are two lined depicting a distance distraction variable. D-V which represents a delta in distance between first and second ends of lever 11 resulting from oscillation of lever 11 along plane x. First and second pivot socket roof 10*e*2 of lid 10 is shown having first and second detent stop 10*v* for accepting in a partial holding relationship with first and second bearing 11*e*. Also shown is 10*a*1 and 10*d* for perspective.

FIG. 8*h* shows a side elevation of lid 10 showing lid fenestration 10*d*, lid fenestration 10*a*, lid fenestration boss outer surface 10*a*2 pivot socket roof 10*e*1, pivot socket roof 10*e*2, side wall 10*j* of lid 10, rim side 10*k* of lid 10, under sealing surface 10*l* of lid 10, sunken quad carrier nest/cap nest 10*a*1, living hinge 10*u*, bottom rim surface 10*r*, and sealing surface 10*n* of lid 10.

FIG. 8*i* is a partial blow up detail side view of the features disclosed in the connected circle of FIG. 8*h*. Disclosed in the detail is pivot socket roof 10*e*2 of pivot socket 10*f*, and the outwardly extending raduised distraction ramp depicted by 10*v*-1, 10*v*-2 and 10*v*3. Veritcal lines extending to distraction variable DV depict a travel variable distance which corresponds to the delta v travel differentiation between first and second ends if lever 11 as leverage is imparted to operated lever 11 along the y plane. Also shown is lid sidewall 10*j*, lid side rim 10*k*, seal surface 10*l*, seal surface 10*n*, bottom rim 10*r*, living hinge 10*u*.

FIG. 8*j* is a front elevation view of lid 10 disclosing details lever hook 10*h*, living hinge 10*u*, cap nest sunken detent 10*a*1, pivot socket 10*f*, lid fenestration 10*d*, pivot socket distraction ramp/roof 10*e*2, lid fenestration 10*a*, sealing surface 10*n*, lid rim 10*k*, living hinge 10*u* an lid side wall 10*j*.

FIG. 8*k* is a partial blow front elevation view of the details disclosed in the connected circle of 8*j* disclosing pivotal socket 10*f*, lever position locations D-180, D-150, D-150, D-120, D-90, D-60, D-30, D-0 which are depicted on the outwardly extending peripheral distraction/retraction ramping surface edge of pivotal socket roof 10*e*2 of socket 10*f*. Also shown is lid rim 10*k*, lid sealing surface 10*n*, lid sealing 10*l*, lid bottom rim 10*r*, lid boss sealing surface 10*a*2, and for perspective the bottom surface corner of sunken cap/nest detent 10*a*1.

FIG. 9 is a top perspective view of quad carrier 12 disclosing lid fenestration plug and negative air pressure/fluent material passage 12*a*, prime manifold transfer container cap holder 12*b*, lid fenestration caps 12*c* and 12*d* shown in carrier connections 12*b*1, 12*c*1, 12*d*1. Details of 12*a* include a tubing connection 12*a*2, air pressure transfer/liquid material transfer passage 12*a*1 which is shown primarily positioned sunken deep to the surface of the top surface of lid 10, as well as sunken sidewall surfaces 12*a*3.

Also disclosed with respect to 12*b* are under rim surface 12*b*4, outer wall surface 12*b*3 and prime manifold transfer container cap centering strut 12*b*2 of 12*b*.

FIG. 9*a* shows a partial blow up detail of features disclosed in the circular portion of FIG. 9 of 12*b*2. Show in the center of this figure is prime manifold container cap nest strut 12*b*2, inner sealing surface 12*b*4.

FIG. 9*b* is a top plan view of FIG. 9 showing substantially the same features.

FIG. 9*c* shows a partial blow up detail of features connected circle of FIG. 9*b*. In this blow up detail of 12*b* is disclosed three prim manifold transfer container cap nest centering struts 12*b*2 as depicted.

FIG. 9*d* shows a cross section of quad carrier 12 taken at 9 AD of FIG. 9*b*. Disclosed in this cross section details of 12*b* is outer surface 12*b*3, inner sealing surface 12*b*4, and prime manifold transfer container cap nesting strut 12*b*2. Also disclosed in 12*a* is negative pressure transfer/liquid material transfer port connector 12*a*1. 12*a*2 shows that the substantial length of the port connector 12*a*1 is sunken deep to the sealing surface 12*a*4 which connects at the top surface of lid 10. Also shown is sunken sidewall surface 12*a*3.

FIG. 9*e* is a bottom plan view of quad carrier 12 showing lid fenestration cap 12*d*, 12*c*, lid fenestration plug and air transfer/liquid transfer plug 12*a*. Prime Manifold transfer container nesting cap 12*b* and quad carrier connections 12*c*1, 12*d*1 and 12*b*1 are also disclosed. Also disclosed are through transfer lumen 12*a*1 of 12*a* and sealing surface 12*a*4, sidewall detent sunken surface 12*a*3, and bottom surface 12*a*5 of 12*a*.

FIG. 10 shows a to perspective view of a lever constructed to impart leverage. This leverage is imparted in part with respect to a sealing and unsealing physical and functional relationship between lid 10 and canister 7. Such leverage is induced by operating lever 11 constructed to impart a separating and jacking force to first and second jacks 11*a* and 11*a* and first and second hooks, 11*c* and 11*c*. Such leverage is imparted around pivot 11*d*. FIG. 10 discloses 10 discloses lever 11 first jack 11*a*, second jack 11*a*, first distraction bearing 11*e*, second distraction 11*e*, first and second pivot 11*d*, first and second hook arm 11*b* and first and second hook 11*c*. 11*f* discloses a location on lever 11 defining a moment arm distance with respect to first and second pivot 11*d*. In one scenario lever 11 operates as a moment arch. In another scenario operates as a separating jack. In another scenario as a sealing clamp. In another scenario lever 11 operates as a hook distracter. In another scenario lever 11 operates as a hook circumventor. In another scenario lever 11 provides stiffness in one plan and flexibility in another plane. In another scenario lever 11 provides rotational counter stiffness between lid 10 and prime manifold transfer container. In another scenario lever 11 provides longitudinal feasibility. In another scenario lever 11 operates as a canister rim circumventor. In another scenario lever 11 operates as a spring retractor, causing a reduced variable distance between first and second jacks 11a, diminishing the distance between first and second jacks 11a aligning the jacks with canister rim 7e in preparation for the leverage moment to apply separation forces to lid 10 and canister 7. In another scenario lever 11 provide common operational connection between a first and a second end of lever 11, and first and second jack 11a, first and second bearing 11e, first and second pivot 11d, first and second hook arm 11b and first and second hook 11c. In another scenario lever 11 operates as a carrying handle. In another scenario lever 11 provides a handle for pouring. In another scenario lever 11 operates as a spring.

Figure 15:
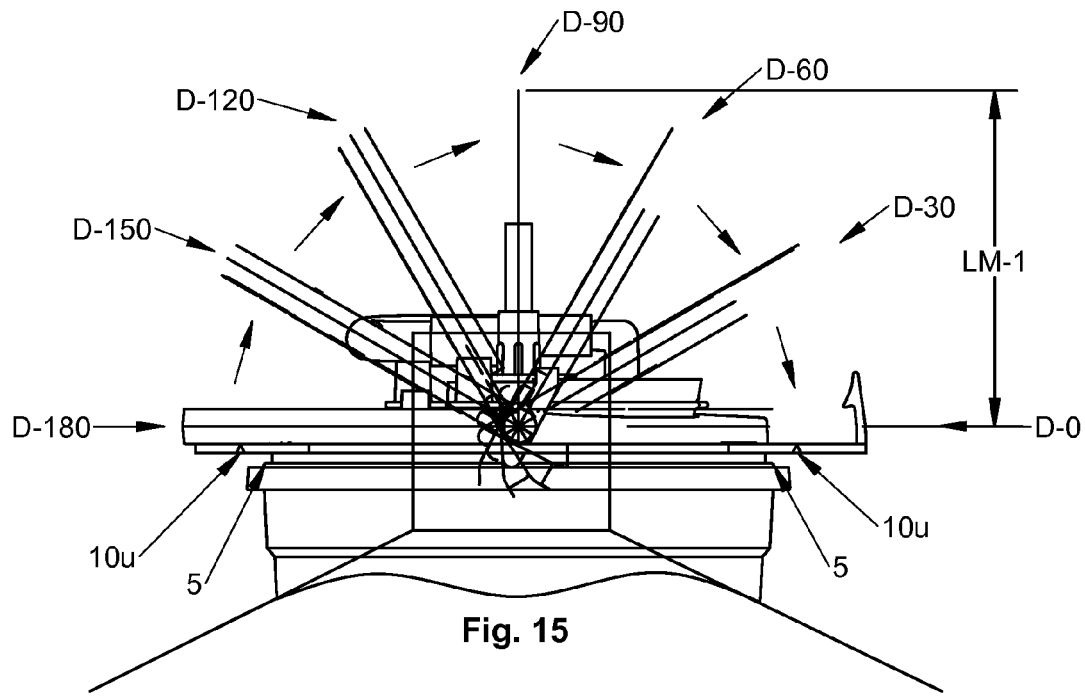
FIG. 15 is a partial front elevation showing how lever 11 imparts a seal clamping force between lid 10 and canister 7 as lever 11 oscillates from D-180 to D-0, imparting hooking and clomping selectively decreasing gap 22.

FIG. 10a is a side elevation view showing lever 11, leverage distance 11f, depicted by arrows defining LM-1, leverage distance point at hook 11b represented by arrows depicting LM-3, and leverage distance point at 11a represented by arrows depicting LM-2. Leverage imparted by lever 11 operates with respect to the ratio of the differential difference between LM-1 and LM-3 when lever 11 oscillates from D-180 to D-0 as depicted in FIG. 15 plus the operating force.

FIG. 10b shows lever 11 depicting leverage moment force distance 11f as depicted by arrows LM-1, leverage moment force distance at 11a as depicted by arrows LM-2 and moment lever force distance at 11b as depicted by arrows LM-3. Moment leverage forces imparted by lever 11 are depicted as how lever 11 would move from D-0 to D-180 as shown in FIG. 14.

Figure 14:
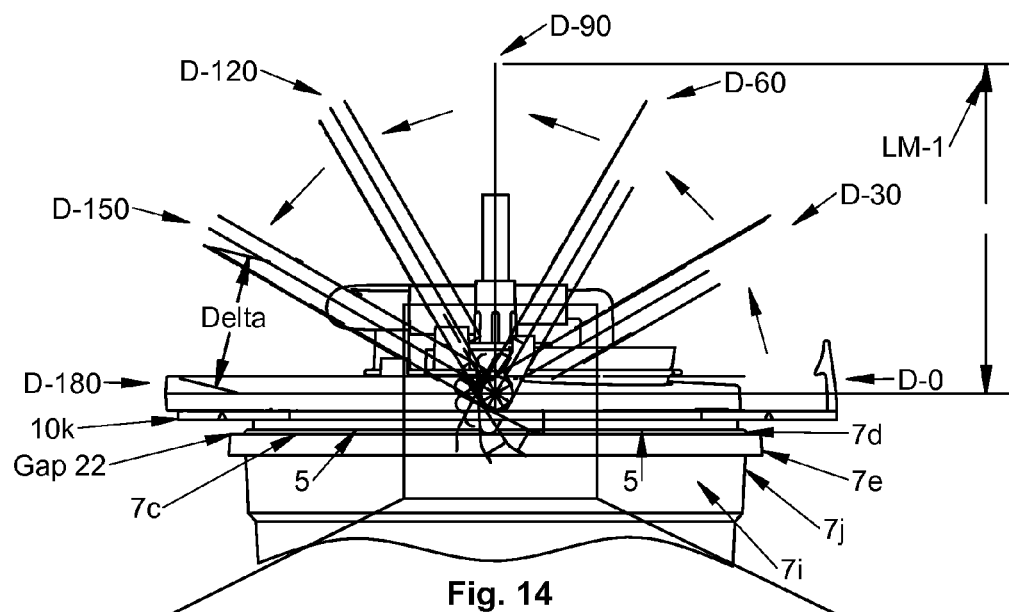
FIG. 14 is a partial front elevation view of how moment lever 11 imparts its seal locking and seal distracting force with respect to the physical and functional relationship between the canister 7 and lid 10, as moment lever 7 ranges/oscillates from D-0 to D-180.

FIG. 10c represents lever 11 showing a position at D-90 in operational relativity to D-90 in FIG. 14, D-90 in FIG. 15, FIG. 16c, FIG. 17c, FIG. 18c, FIG. 20, FIG. 21, FIG. 21a FIG. 21b. Such figures are also operationally relevant to FIG. 10g. FIG. 10c shows first and second pivot 11d, first and second jack 11a, first and hook arm 11b, first and second hook 11c and first and second bearing 11e. Three arrow defining three places representing delta e at D-90 pointing to first and second bearing 11e, delta 11a at D-90 pointing to first and second jack 11a, delta c at D-90 pointing to first and second hook 11c defining a variable distraction distance defined by the operational expansion a factor of DV times 2, that causes an effective result of moving the lever from D-0 to D-90 or from D-180 to D-90. DV×2 which stands for delta variable distance at a factor of 2 defines the expansion distance when looking at the DV arrow of blow up detail 8g of FIG. 8f and blow detail 8i of FIG. 8h. The designation distance variable×2 relates to the aggregate expansion distance delta e at D-90 at Delta c at D-90 as first and second bearing 11e of first and second ends of lever 11 travel along first and second outwardly projecting distraction ramp represented as shown along D-180, D-150, D-120, D-90, D-60, D-30 and D-0, of FIG. 8 which corresponds to the outwardly projecting roof 10e2 of pivot socket 10f. Shown in FIG. 8i is a partial blow up detail side elevation of the outwardly projecting distraction ramp of roof 10e2 of pivotal socket 10f. DV×2 f 10c represents the aggregate of distraction delta resulting from the operation oscillation of lever 11 in a plane y.

FIG. 10d is a partial blow up detail of connected circle of 10c showing one of two bearing 11e, one of two jacks 11a, one of two pivots 11d, one of two hook arms 11d, one of tow hooks 11c.

FIG. 10e is a side elevation of lever 11 as would be depicted at D-180 as shown represented in FIG. 14, FIG. 14a, FIG. 16, FIG. 17 FIG. 18. Shown in FIG. 10e are first and second jacks 11a, first and second pivots 11d, first and second hooks 11c. Also shown respective to lever 11 are arrows DV-min standing for distance variable at a minimum retraction distance between first and second ends of lever 11, related to the minimum delta distance of first and second jacks 11a at D-0, and the minimum delta distance of first and second hooks 11c at D-0.

FIG. 10f is a partial blow up detail of one of first and second jack 11a, one of first and second pivot 11d, one of first and second hook arm 11b, one of first and second hook 11c.

FIG. 10g shows lever 11 from a side opposite of the view shown in FIG. 10c. Disclosed in this view are first and second bearing 11e, fist and second hook arms 11b, first and second hooks 11c and first and second pivots 11d, relative to lever 11 at D-90 as represented in relationship to maximum travel distance between first and second bearing 11e and first and second hooks as shown here equivalent to DV×2 which is distance variable delta times 2. Maximum dist5ractoin delta between first and second bearing 11e at 90 and maximum distraction delta between first and second hook 11c at D-90 are respectively similar to DV×2 as described in the disclosure of FIG. 10c and all of the corresponding figures in the instant case recited as being relative to FIG. 10c.

FIG. 10h is a partial blow up detail view of connected circle portion of FIG. 10g showing a blow up detail of one of first and second bearing 11e, one of first and second pivot 11d, and one of first and second hook 11c.

FIG. 10i shown moment lever 11 at D-180 and two sets of arrows depicting minimum distraction distance delta 11b at D-1980 between first and second hooks 11c, and minimum distraction distance delta at a D-180 between first and second jacks 11a. DV minimum represents the minimum distraction distance delta caused by the contact relationship between first and second bearing 11e and first and second lid roof 10e1 and 10e2 at D-180 as shown in FIG. 8g and first and second bearing 11e similarly in contact with first and second lid point 10g-1 of lid 10.

FIG. 10j shows a blow up detail of connected circle of FIG. 10j showing one of first and second hooks 11c, one of first and second pivots 11d, one of first and second hook arms and one of first and second jacks 11a.

FIG. 11 is a top perspective view of flush plug 9 constructed such that it fits is sealable engagement within the throat neck of a pour bottle as depicted I FIG. 1, through 5b, 6, 19a, 19b, 20b, 21b. Features disclosed with regards to flush plug 9 include to surface 9a, patient ingress fluent material passage through put lumen 9e, sunken recess 9g, sunken patient suction tubing port connector 9f, flush plug rim 9b, bottle neck sealing surface 9b, outer diameter surface 9c, spout 9d, and corresponding through put bottom 9e. Also disclosed is negative vacuum transfer lumen 9h.

FIG. 11a shows a top plan view of flush plug 9 disclosing top surface 9a sunken recess 9g, sunken recess bottom surface 9g1, patient suction through put lumen 9e, flush plug outer rim 9m, sunken patient suction tubing port 9f and negative atmospheric pressure through put lumen 9h.

FIG. 11b is a side cross sectional view taken at line MM of FIG. 11b. Details disclosed with respect to FIG. 11b include patient suction tubing through put lumen 9e, negative atmospheric pressure through put lumen 9h, suction patient tubing recess 9g, recessed sunken patient suction tubing connection port 9f, sunken recessed tubing recess bottom surface 9g1, flush plug top 9a, flush top surface rim 9m, flush plug rim undersurface sealing surface 9k, and flexible thin wall flush plug side wall sealing skirt 9b.

FIG. 11c is top perspective view of a partial sub assembly of flush plug 9 in connection with patient suction tubing 19a and elbow 17. Details also disclosed in FIG. 11v include patient suction tubing material through put lumen 9e, patient tubing recess 9g, flush plug surface rim 9m, patient tubing 19, flush plug top surface 9a, flush flexible side wall sealing skirt 9b, other diameter surface 9c, filter 15 having bee press fitted into filter space 9j and downwardly projecting lumen 9e. Also disclosed is negative transfer pressure communication space 9h disposed to accept on end of tubing communication link 16.

FIG. 11d is a top plan view of FIG. 11c. Details disclosed in this view include flush plug surface 9a, surface rim 9m, suction tubing end connector 9a, patient tubing suction recess 9g and elbow 17.

FIG. 11e is a cross section of sub-assembly shown in FIGS. 11c and 11d, taken at line LL of FIG. 11d. Detailed disclosure of this figure include patient suction tubing through put lumen 9e, patient suction tubing 19, patient suction tubing connection end 19a, patient suction tubing connecting sunken recess 9g, sunken recessed patient tubing port connector 9f, to surface 9a of flush plug 9, flush plug rim 9m, port structure 9f, top surface 9a of flush plug 9, rim 9m of flush plug 9, under rim surface 9k of flush plug 9, flexible side wall surface sealing skirt 9b, flush plug diameter 9c, patient suction tubing connector recessed bottom 9g1, elbow 17, negative atmospheric pressure lumen 9h, recessed elbow connection surface 9l, negative atmospheric through put lumen 9i, filter 15 which is press fit in filter space 9h of flush plug 9.

FIG. 12 is atop perspective view of a seal. This seal is sized and shaped to fit on the downwardly projecting boss 10q as shown in FIG. 8d of drawing sheet 8. This seal is made of a relatively pliant soft rubber or silicone and is forgiving to contact with a prime manifold transfer container such as a pour bottle, and forms a vacuum locking seal between the bottle and lid 10. This seal here discloses an outer rim 13a, a recess slot 31b and an inner wall 13c. Seal 13 is intended to be affixed to lid 10 at 10q to provide a vacuum tight seal between lid 10 and any one of prime manifold container 1, 1a, 1b, 1c, 1e, or 1f.

FIG. 12a is a side elevation view of seal 13 showing FIG. 12.

FIG. 12b is a cross sectional view of seal 13 taken at ling GG of FIG. 12a. FIG. 12b discloses details depicting outer wall 13a, slot 13b, inside wall 13c, bottom 13e and radiused feature on the inside edge of wall 13g.

FIG. 12c is a blow up detail of features disclosed in connected circle of FIG. 12b. This detailed blow discloses outer wall 13a, slot 13b, inner wall 13c, surfaces of slot 13b comprising inner surface 13d of inside wall 13, inner surface 13a of bottom 13e, inner surface 13g of outer wall 13a.

FIG. 12d is a top plan view of seal 13 showing outer wall 13a, slot 13b, inner wall 13c and slot bottom sealing surface 13h.

FIG. 12e is a bottom plan view showing bottom surface 13e.

FIG. 13 is a top perspective view of lid and canister seal adapter 21. Disclosed in this view is lid seal surface 21b, lid seal surface 21c, lid seal surface 21d and canister seal surface 21a.

FIG. 13a is a side elevation view of seal adapter 21 disclosing lid seal surface 21c, lid seal surface 21d, adapter rim 21e, canister seal surface 21a and adapter lid undersurface 21f of adapter rim 21e.

FIG. 13b is a side cross sectional view of adapter 21.

FIG. 13c is a blow up detail corresponding detail of connected circle of FIG. 13b disclosing details of lid seal surface 21c, lid seal surface 21d, rim surface 21e, rim undersurface 21f, rim sulcus 21g and canister seal surface 21a.

FIG. 13d is a bottom view of seal adapter of FIGS. 13 through 13c.

FIG. 14 is a partial front elevation view showing how lever 11 may be operated. This view is arranges and set up in a Cartesian coordinate system. This view includes horizontal planes x & y an and vertical plane z. Horizontal plane y may be viewed from right to left and left to right or from D-0 to D-180 to D-0 of with perspective relative to the arrows and how lever 11 may impart leverage force while oscillated along arrows, along the y plane shown on drawing sheets 17 & 18 among other things. When lever 11 moves along the y plane lever 11 oscillates from D-0 to D-30, to D-60, to D-90, to D-150, to D-150, to D180 as depicted in this view. In the horizontal x plane is represented by looking straight through from front to back and back to front. Horizontal x plane may be further understood by looking at FIGS. 10c and 10g and going from right to left or going from left to right in FIG. 10c or 10g. FIGS. 10c and 10g are representative examples of D-90 of FIG. 14 positioned at D-90 with respect to D-90 of FIG. 14. Vertical plane z is represented by gap 22. Delta gap 22 is influenced by the force imparted by lever 11, moment LM-1 of FIGS. 10a and 10b, and how leverage available is imparted on moment LM-2 of FIGS. 10a and 10b, with respect to first and second jacks 11a and moment LM-3 with respect to first and second hooks 11c. As lever 11 oscillates from D-0 to D-90 moving along a y plane, first and second lever bearing 11e as shown in FIGS. 10, 10c and 10g, move along first and second roofs 10e2 and 10e1 of pivot socket 10f of lid 10, along the outwardly extending first and second distraction/retraction ramp from D-0 to D-90 as depicted in FIG. 8g and FIG. 8k imparting the distraction distance delta DV as shown in FIG. 8i with respect to first and second pivotal socket housing roofs 10e1 and 10e2. Such oscillation of lever 11 along a plane y imparts distraction and retraction distances between first and second ends of lever 11 along horizontal plane x. Such first and second distraction and first and second retraction and rotation represents a rotational and reciprocation combining physical and functional motion between lid 10 and lever 11, first and second pivot 11d and first and second socket 10f of lid 10. While at D-90 while lever 11 is at a position whereby a maximum first and second delta distraction distance DV may be maintained and is sufficient for hook 11c of lever 11 to circumvent canister rime 11e and rotate sufficiently through first and second slots 10b1 and 10b2 of lid 10. As lever 11 of FIG. 14 oscillates along the y plane from D-90 to D-180 first and second bearing 11e of lever 11 moves along the first and second outwardly projecting first and second roofs 10e1 and 10e2 of first and second pivot socket 10f of lid 10 as depicted in FIGS. 8g, 8i & 8k form D-90, to D-120, to D-150 to D-180. Such movement of lever 11 along the y plane from D-120 to D-180 imparts a retraction in distance between first and second bearing 11e, first and second pivot 11d, first and second hook 11c, first and second hook arm 11b and first and second jack 11a. FIG. 14 shows at D-0 lever 11 secured under a snap lock latch 10h. Lever 11 may be oscillated along a series of arrows through the y plane from D-0 to D-180. This oscillation through the y plane represents a change in the relationship between lid 10 and canister 7. Also shown in this FIG. 14 is canister seal surface 7d, canister rim 7e, canister seal surface 7c, gap 22, outer lid rim 10k, of lid 10, and arrows LM-1 depicting the relative lever moment arm potential leverage capacity of lever 11.

Figure 14A:
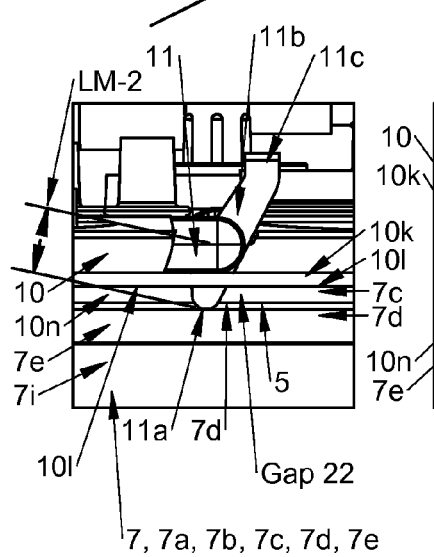
FIG. 14a is a blow up detail of connected box portion of FIG. 14 showing lever 11 having seal distraction forces between lid 10 and canister 7 as lever 11 oscillates between D-120 and D-180. This Figure depicts how moment lever 11 imparts seal distraction forces between between lid 10 and canister 7 as moment lever 1 travels from D-20 to D-150 breaking the seal between the seal between lid 10 and canister 7 inducing an increase in gap 22.
Figure 14B:
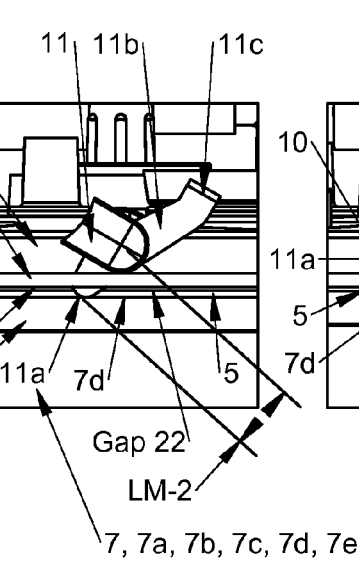
FIG. 14b takes moment lever 11 at a position between D-90 and D-180.
Figure 14C:
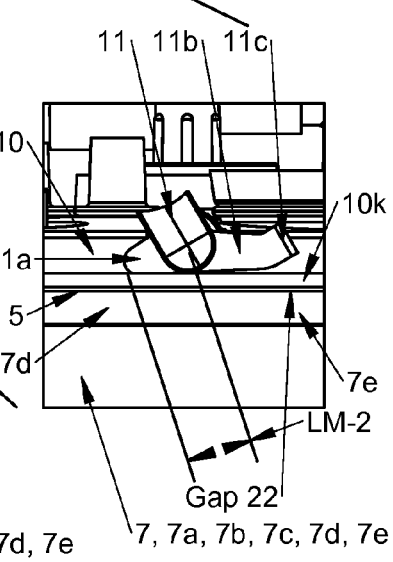
FIG. 14c takes moment lever 11 at position D-90.

FIGS. 14a 14b, and 14c represent the same numerical part identifiers however gap 22 is different in each of FIGS. 14, 14a, 14b and 14c as lever 11 moves through the y plane from D-90 to D-180. FIGS. 14a, 14b, and 14c represent blow up detail with respect to connected box of FIG. 14. FIG. 14a, 14b, and 14c each show lever moment LM-2, delta gap 22, lever 11, jack 11a, lid 10, lid rim 10k, canister rim 7e, canister seal surface 11d, hook arm 11b, seal surface 10m of lid 10, seal surface 7c of canister 7. FIGS. 14c, 14b, and 14a when viewed in that order demonstrates how when lever 11 is oscillated through the y plane between D-90 to D-180 how lever jack 11a swings about in a pivotal axis in horizontal plane x lever moment LM-1 imparting a force in relative ratio potential relationship to lever moment 2 shown in FIGS. 14c, 14b, and 14a as lever jack 11a contacts surface 7d of canister 7 the leverage imparted breaking the seal between lid 10 and canister 7 subsequently increasing gap 22 and providing dissociative movement along vertical plane z with respect to canister 7 and lid 10. Such movement utilizes leverage to break the seal between lid 10 and canister 7.

Figures 15A, 15B, 15C:
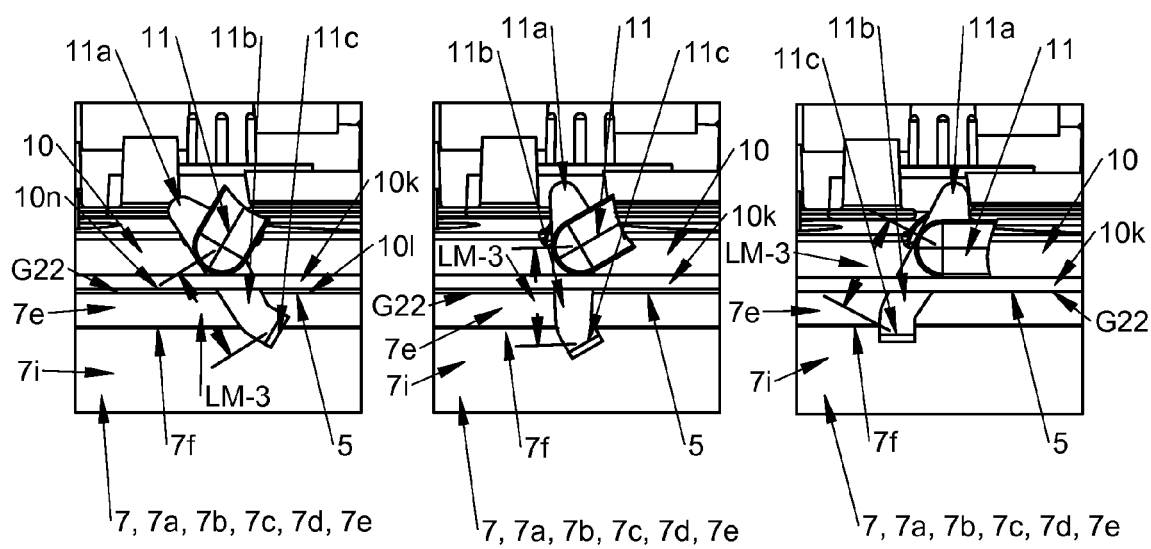
FIG. 15a is a partial blow up detail of connected box of FIG. 15 showing hook 11c as it circumvents canister rim 7e.
FIG. 15b is a partial blow up detail of connected box of FIG. 15 showing hook 11c having circumvented canister rim 7e.
FIG. 15c is a partial detail blow up of connected box of FIG. 15 showing moment lever 11 at D-0 and hook 11c having imparted moment lever force closing gap 22 and physically and functionally holding lid 10 and canister 7 in sealing engagement.

FIG. 15, FIG. 15a, FIG. 15b, and FIG. 15c shows substantially the same numerical identifies as shown in FIGS. 14, 14a, 14b, and 14c, the difference shown in FIGS. 15 relates to the oscillation of lever 11 imparting force through opposite movement along the y plane with respect to FIGS. 14. Such oscillations are represented in FIG. 15 by Leverage moment LM-1 imparting its force through oscillation along the y plane in a direction in reverse of that of FIG. 14 imparts a reverse action with respect to the distraction and retraction delta distance changes between first and second bearing 11e, first and second pivot 11d, first and second hook 11c, first and second jack 11a. Shown in FIGS. 15e is lever 11 shown starting at D-180 and moving along the y plane to D-150, D-120, D-90, D-60, D-30, D-0. LM-1 is shown as the leverage moment which may be exerted in relative proportion to LM-3 with respect to FIGS. 15a, 15b, and 15c. FIGS. 15a, 15b, and 15c each show lid 10, lever 11, hook 11c, jack 11a, hook arm 11b, gap 22, lid seal surface 10n, lid seal surface 101, outer lid rim 10k, canister rim 7e. With respect to FIG. 15 and looking at FIGS. at 15a, 15b, & 15c in that order it is noted that leverage is imparted along LM-1 to LM-3 as lever 11 oscillates along the y plane from D-90 to D-0, hook 11c rotates about the x axis and circumvents the canister rim 7e in the x plane having been distracted and retracted as hook 1c catches the undersurface of canister rim 7f of canister rim 7e. LM-1 imparts leverage along LM-3 to hook 11c along hook arm 11b as hook 11c catches undersurface 7f of rime 7e and imparts a closing/sealing force along vertical plane z and closing gap 22 and forming and sustaining a seal between lid 10 and canister 7. It is important to note with respect to FIGS. 14 through 18f that the average age of the surgical nurse is 45 years of age. The assembly and disassembly of canister can be a difficult problem. The purpose of LM-1 imparting force to M-2 and LM-3 is to provide the operators the assistance of a moment arm leverage potential in creating and breaking a seal between lid 10 and canister 7. Therefore FIGS. 14 and 15 demonstrate how leverage may be used to assist in creating and breaking a seal with respect to handling a connectabe/disconnectable lid and canister system.

FIG. 16 through 16f show the blow up detail of FIG. 8g of connected circle of top plan view of FIG. 8f. Shown in FIG. 16 through 16f, lever 11 is cut away close to its pivot 11d such that the contact between bearing 11e and outwardly distraction/retraction ramp 10e2 of pivot socket roof 10f may be seen in each of respective positions D-180 of FIG. 16, D-150 of FIG. 16a, D-120 of FIG. 16b, D-90 of FIG. 16c, D-60 of FIG. 16d, D-30 of FIGS. 16e and D-0 of FIG. 16f. The contact between bearing 11e, and outwardly projected distraction/retraction ramp of roof 10e2 of pivot socket 10f, engage in the distraction/retraction relationship as lever 11 oscillates to and from and from and to d-0 to D-180 and from D-180 to D-0. Gap 23 as shown in FIGS. 16 through 16f which is a gap between lever 11 and fist and second slots 10b and 10b2 increase and decrease as shown in the top plan details of FIGS. 16 through 16f as LM-1 imparts leverage potential as it moves to and from in the y plane resulting in distraction and retraction of first and second bearing 11e, first and second pivot 11d first and second hook arm 11b, along the x plane. FIG. 16 shows LM-1 at D-180, FIG. 16a shows LM-1 and D-150, FIG. 16b shows LM-1 at D-120, Figure c shows LM-1 at D-90, FIG. 16d shows LM-1 at D-60, FIG. 16e shows LM-1 at D-30, and FIG. 16f shows LM-1 at D-0. It apparent from looking at the sequential blow ups of FIGS. 16 through 16f of in reverse from FIG. 16f to FIG. 16 that oscillation of LM-1 in the y plane imparts a distraction and retraction between the first and second ends of lever 11 in the horizontal z plane. Such distraction and retraction allows the clearance of hook 11c and jack 11a through first and second slot 10b2 of lid 10, as hook 11c and jack 11a rotate about a x plane pivotal axis rotating circumventing rim 7e of canister 7 to hook rim surface 7f with hook 11c as LM-1 travels from D-90 to D-0 as represented by FIGS. 16c through 16f and as LM-1 operates in the opposite y plane direction as represented by reverse sequence 16 through 16 retraction along the z plane along the first and second ends of lever 11 which is induced by the spring character inherent in lever 11 and jack 11a imparts a seal breaking contact force as shown in FIGS. 14c, 14b and 14a breaking the seal between lid 10 and canister 7. FIG. 16 shows blow up details FIG. 8g comprising the components of sub assembly blow up detail of cut away lever 11 and the blow up detail of lid 10. FIG. 16 through 16f disclose variable DV of pivot socket roof 10e2 of pivot socket 10f, hook 11c, lid slot 10b2, hook arm 11b, gap 23, lid rim 10k, jack 11a, and each of respective contact relation points along outer distraction/retraction ramp 10e2 of roof 10f of pivot socket 10f. Respectively recited seriatim herein at D-180 of FIG. 16, D-150 of FIG. 16a, D-120 of FIG. 16b, D-90 of FIG. 16c, D-60 of FIG. 16d, D-30 of FIG. 16d, and D-0 of FIG. 16f.

FIGS. 17 through 17f represent the same blow up details shown in FIGS. 14a, 14b, 14c, and FIGS. 15a, 15b, 15c plus the addition of FIGS. 17c which is a respective blow up detail relative to lever 11 at D-90 of both FIGS. 14 and 15. FIGS. 17 through 17f may be viewed sequentially from 17f to 17 or from 17 to 17f the details disclosed in each of 17 through 17f show lever 11 at D-180 of FIG. 17, 11 at D-150 of FIG. 17a, 11 at D-120 in FIG. 17b, 11 at D-90 in FIG. 17c, 11 at D-60 in FIG. 17d, 11 at D-30 in Figure in FIGS. 17e and 11 at D-0 in FIG. 17f. Each of FIG. 17 through 17f disclose lever 11, lid 10, hook arm 11b, hook 11c, lid rim 10k, lid seal surface 10n gap 22 jack 11a canister seal surface 11d, canister rim 7e and hook surface 7f of canister rim 7e. Also shown by numeral 5 the sealing junction between canister 7 and lid 10.

FIGS. 18 through 18f show a blow up detail of rectangular box of FIG. 8a on drawing sheet 8. Added to this detail is one of first and second ends of lever 11 showing the interaction of lever 11, lid 10 and canister 7 during the impartation of LM-01 during the operation of lever 11. FIGS. 18 through 18f with respect to the impartation of leverage potential corresponds to FIGS. 14 through FIGS. 17f but shown through a bottom plan view blow up detail as shown in FIGS. 18 through 18f. FIG. 18 shown LM-1 at D-180, FIG. 18a shows LM-1 at D-150, FIG. 18b shows LM-1 at D-120, FIG. 18c shows LM-1 at D-90, FIG. 18d shows LM-1 at D-60, FIG. 18e shows LM-1 at D-30, FIG. 18f shows LM-1 at D-0. FIGS. 18 through 18f may be viewed sequentially forward from 18 to 18f of in reverse from 18f to 18. Details disclosed in FIGS. 18 through 18f include canister 7, hook surface 7f of canister rim 7e, lid sealing surface 10f, lid 10, gap 23 of first and second lid slot 10b1 or 10b2, lever 11, hook 11c, jack 11a. FIGS. 18 through 18f show respective distraction and retraction along the x plane along one end of lever 11 with respect to canister 7 and lid 10. It is shown while LM-1 is at D-150, jack 11a has imparted a separation force increasing gap 22 of FIGS. 14 through 17*f*, breaking the seal between lid 10 and canister 7. FIG. 18*b* shows jack 11*a* in a position with respect to LM-1 at D-120 which is relative to LM-1 at D-120 shown in FIGS. 14 through 17*f*. FIG. 18*c* shows LM-1 at D-90 and the delta distance distraction between first and second ends of lever 11 as is described in FIGS. 10*c* and 10*g*, occurs as a result of oscillating 11 from D-0 to D-90 of from D-180 to D-90 imparting a suitable distance between first and second ends of lever 11 such that hook 11*c* and jack 11*a* are distracted, rotated and reciprocated about the axis along the x plane while pivot 11*d* rotates and reciprocates along the x plane in juxtaposed relationship in pivot socket 10*f* of lid 10, and circumvention of rim 7*e* of canister 7 is accomplished through rotation and distraction and retraction of first and second ends of lever 11 during imparting of LM-1 potential force on lever 11. Such circumvention of first and second hooks 11*c* and first and second jacks 11*a* is carried out by simultaneous, leverage in one plane (the y plane) distraction and retraction in another plane (the x plane), and circumvention rotational reciprocation about a pivot axis that projects along the x plane including motion between the lid 10 and canister 7 in another plane (vertical z plane). Hook 11*c* and jack 11*a* are positioned to circumvent rim 7*e* of canister 7, clear and pass through slots 10*b*1 and 10*b*2 of lid 10. It is apparent as shown in FIGS. 14 through 18*f* that oscillation of LM-1 along the y plane provides distraction and retraction of first and second ends of lever 11, along the x plane which imparts increase and decrease in gaps 22 and gaps 23 both inducing and breaking a seal between lid 10 and canister 7. LM-1 moving in the y plane imparts distraction and retraction in the z plane which defines imparting leverage inducing sealing and unsealing in the z plane. As such x, y and z plane action of 11*c*, circumvents rim 7*e* of canister 7 and applies Im-3 through Im-1 a force to compress hook 11*c* against rim surface 7*f* of rim 7*e* decreasing and closing gap 22 providing a seal between lid and canister 7. Lever hook 11*c* circumvents canister rim 7*e* as a result of distraction and pivotally hooks canister rim 7*e* as a result of pivotal retraction. It is apparent from FIGS. 14*f* thorough 18*f* that hook 11*c* undergoes a circumventing pivotal distraction and retraction to clear first and second canister slots 10*b* and 10*b*2. It is also apparent from FIGS. 14 through 18*f* that jack 11*a* also undergoes a pivotal circumventing distraction and retraction in the y plane distracting for clear passage through pivotal slot 10*b*1 and 10*b*2 and pivotal retraction for imparting separating forces LM-1 and LM-2 increasing gap 22 and breaking the seal between lid 10 and canister 7. Plane x, plane y and plane z also represent in FIGS. 14 through 18*f* a first plane and second plane and a third plane and how each of these planes relate to LM-1, LM-2 and LM-3 as well as the physical and functional relationship between lid 10 and canister 7 and lever 11. LM-1 in one plane imparts LM-2 and LM-3 as LM-2 and LM-3 relate to motion in the x plane and how LM-2 an dLM-3 impart interaction between lid 10 and canister 7 in the vertical z plane as it relates to sealing and unsealing between a canister 7 and lid 10.

FIG. 19 is a side elevation view of a typical pour bottle (prime manifold transfer container). This pour bottle may also be identified a prime manifold transfer container or an intravenous solution container, or a irrigation solution container or other container. Prime manifold transfer container of FIG. 19 is disclosed having inner space 28*a* fill lever 8*k*, and is identified as 1, 1*a*, 1*b*, 1*c*, 1*d* and 1*e* to reflect different sizes and shapes. Lid contact surface 8*j*, a thread 8*h*, a throat aperture space 8*i* and general neck 8*g* and cap 8, cap diameter 8*a* also shown in FIG. 19 is numeral 9 removed which represents flush plug 9 having been removed I this Figure.

FIG. 19*a* is a partial cross sectional side view taken a lines 8*h* of FIG. 19. This view discloses inner space 28, it defines the prime manifold transfer container as 1, 1*a*, 1*b*, 1*c*, 1*d*, & 1*e* to reflect different sizes and shapes and a fill line 8*k* which represents collected waste material. Also shown is flush plug 9 disposed in the throat aperture space of neck 8*g* of the embodiment shown in FIG. 19. Cap 8 has been placed back on the bottle (prime manifold transfer container) and secured a 8*e* and 6*b* such that waste material 8*k* may be removed safely secured as shown in FIG. 19*a*.

FIG. 19*b* shows a partial side elevation of the embodiments of FIGS. 19 and 19*a* with the cap 8 shown suspended above the prime manifold transfer container. Flush plug 9 is disposed within the neck of the transfer container. Cap 8 is shown in position in perspective to be secured to the prime manifold container shown in this FIG. 19*b*.

FIG. 20*a* shows an alternative scenario whereby once the collection operation has been completed patient suction tube 19 vacuum source suction tube 20, may be removed, elbow 17 may be placed to cap lid port 10*d* and cap nest 12*b* may be placed over lid fenestration 10*a* forming a sealing engagement between seal surface 12*b*4 of cap nest 12*b* and seal surface 10*a*2 of lid boss 10*s*. FIG. 20*a* represents a scenario the entire system may be removed from the collection site whether or not there is waste material within space 28 only or there is waste material in space 28 and space 24. This scenario also shows lever 11 snap locked down under snap lock 10*h* of lid 10 which represent first and second hook 11*c* maintaining a locking seal between lid 10 and canister 7 as shown in D-0 of FIGS. 14 & 15 and also as shown FIG. 15*c*, FIG. 16*f*, FIG. 17*f* FIG. 18*f*.

FIG. 20 represents an alternative scenario whereby lever 11 operates as a carrying handle. Lever 11 is shown at D-90. Elbows 17 and connector 10*c* is shown relative to that in FIG. 20*a*. When lever 1 is at D-90 hook 11*c* is moved with respect to positions shown represented by FIGS. 10*c*, 10*g*, 16*c*. First second third and fourth snap down locks 10*i* are shown maintaining a locking seal engagement between lid 10 and canister 7 disclosing first, second, third and fourth hook 10*r* of snap down lock 10*i* engaging rim surface 7*f* of rim 7*e* maintaining a locking seal relationship between lid 10 and canister 7. This scenario of FIG. 21 is disclosing lever 11 in operation as a carrying handle. This allows personnel to carry two containers at once using lever 11 as a handle, yet maintaining the seal 5 between lid 10 and canister 7 and maintaining protection of the outside environment from the waste material contained within space 28 or in space 24 and space 28 while keeping the canister collection system interior separate from the exterior.

FIG. 20*b* is a partial cross sectional view taken at line AJ of FIG. 20*a*. This cross sectional view also represents a scenario of FIG. 20*a* and FIG. 20. Shown in this Figure is prime manifold transfer carrier space 28, a prime manifold 1, 1*a*, 1*b*, 1*c*, 1*d* and 1*e* and this goes within canister 7, 71*a*, 71, 71*c*, 71*d*, 71*e*. Having gap 22 maintained as a seal maintained by first second third and fourth snap down locks 10*i*. Lid 10 and canister 7 are held together for transport of waste material from the collection site with lever 11 either at D-90, D-0 or D-180. Disclosed details of FIG. 20*b* include lever lock latch 10*h*, cap nest 12*b*, on lid boss 10*s* forming a seal there between with respect to lid boss seal surface 10*a*2 and cap nest seal surface 12*b*4 of cap nest 122. Flush plug 9 is shown disposed within the neck of prime manifold transfer container 1 through 1*d*. A seal 6*a* is shown between flush plug 6 and the bottle neck (prime manifold transfer container 1 through 1*d*0 Seal 13 of FIG. 12 to 12*a* is shown affixed to rim 10*q* of FIG. 8*d*. Seal 6 is formed between transfer container 8*j* and seal 13 at 6. Patient through put lumen 9*e* of flush plug 9 and vacuum throughput lumen 9h of flush plug 9 are effectively sealed through the inversion and connection of quad carrier cap nest 12b2 to lid boss 10s. Lid fenestration 10c, quad carrier 12a is effectively sealed by the maintenance of elbow 18 and lid fenestration 10d is effectively sealed by the placement of elbow 17. Lid seal surface 101, 10m and 10n are effectively maintained in contact with canister seal surface 7b, 7c, and 7d through the deployment first second, third and fourth snap down locks 10i.

FIG. 21 shows a essentially the same canister system removal scenario however elbow 18 and elbow 17 and communication link tubing 16 have been removed and quad carrier cap/nest 12c has been placed over tubing connection port at 12a and quad carrier cap 12d has been placed lid fenestration 10d. FIG. 21 is a top perspective view of the scenarios of FIG. 21a better disclosed in FIG. 21 shows first second third and fourth living hinge 10u of first second third and fourth snap down lock 10i and how first second third and fourth hooks 10r may hook bottom surface 7f of canister rime 7e.

FIG. 21b is a partial cross sectional view taken alt line AL of FIG. 21. Figure represents the same canister removal scenario as shown in FIGS. 21 and 21a. This cross section was taken at line AL to represent how quad carrier caps 12c and 12d may be placed over quad carrier 12a and lid fenestration 10d after removal of corresponding suction tubing's and elbow connectors. Also shown in this view is cross section of filter 14 as it fits to the downwardly projecting boss defined by the undersurface of lid fenestration 10d of lid 10 which is sunken deep to the top of lid 10 surface. Filter 14 may embody porosities ranging from 12 micro to 50 micron. Also shown in this view is filter 15 which is the filter which fits into flush plug 9 at its outflow site in FIG. 11c which occupies space 9h and 9j of FIG. 11d. The scenarios of FIGS. 19, 19a1 and 19b allow removal of waste material in a product transfer container when it is desirable to remove material just in the transfer container. The waste material removal scenario of FIGS. 20, 20a and 20b present a scenario where it is desirable to remove waste material in a transfer containing while maintaining the transfer container disposed inside the collection system. Such removal may be carried out in accordance with FIG. 20, first second third and fourth snap down locks 10i are deployed and then lever 11 functions as a handle for carrying or in accordance with the scenario of FIG. 20a whereby first second third and fourth snap down locks 10i are not deployed and lever 11 is maintained under lever lock 10h and first and second lever hooks 11c maintain a locking seal engagement between lid 10 and canister 7 at rim surface 7f of rim 7e of canister 7. FIGS. 21, 21a and 21b represent the same waste disposal scenario of earlier Figures however quad carrier caps 12c and 12d are deployed to seal the corresponding lid fenestrations and the pass through port structure of quad carrier 12a.

FIGS. 22, 22a and 22b represent another scenario for collection of waste material utilizing the invention of this instant case. Such a scenario includes a collection operation wherein a prime manifold transfer container (pour bottle/IV container) is not present. In this scenario simple manipulation of quad carrier 12 provide adequate sealing of appropriate lid fenestrations. FIG. 22 shows suction source tubing 20 connected directly to lid fenestration 10d, patient suction tubing 19 connected to quad carrier 12a, and quad carrier cap nest 12b seal ably connected to boss 10s covering lid fenestration 10a on boss 10s. This simple scenario collection of waste material in the instant collection system providing all the necessary seals such that the seal is effective in collecting waste mater whether or not there is a pour bottle (prime manifold transfer container) available to connect to and dispose waste material. Under both scenarios waste material may be collected in both space 28 and in space 28 and space 24 or in just space 24.

FIGS. 23, 23a and 23b disclose a scenario liquid waste material may be poured simultaneously from space 24 and space 28 subsequent to the collection of waste material. It is understood that prime manifold transfer container may hold waste material and waste material space 245 may hold material. Simultaneous compartment emptying may ensue by removing quad carrier cap nest 12b from lid boss 10s of lid 10 and removing quad carrier 12a from lid fenestration 10c. FIG. 23 shows an inverted collection system allowing the egress of waste material. FIG. 23a is a top plan view of quad carrier configuration of FIG. 23. It is shown that canister space 24 may be viewed at 7, 7a, 8b, 78c, 7d and 7e along with a top vertical view of the side of prime manifold transfer container 1, 1a, 1b, 1c & 1d through lid fenestration 10c and transfer container neck 8i is visible through vertical view as shown disposed in lid fenestration 10a. Quad carrier cap/nest carrier 12b has been removed from boss 10s of lid 10 exposing space 28 through bottle neck 8i opening up a dispensing passage through 10a and through quad carrier 12a has been removed from lid fenestration 10c exposing space 24 for dispensing. FIG. 23b is a cross sectional view taken at section AP of FIG. 23a. FIG. 23b represents the waste dispensing scenarios of FIGS. 23 and 23a. Disclosed in FIG. 23b transfer container 1, 1a, 1b, 1c, 1d lid, 10, lid fenestration 10c having quad carrier 12a removed, lid fenestration 10d having quad carrier cap 12d still attached, filter 14 attached to downwardly projection of boss 10d of lid 10. Seal engagement 5 between lid 10 and canister 7 may be maintained by lever 11 at D-0 and or by first second third and fourth lock down latches 10i, first second third and fourth hook 10r engaging the undersurface 7f of rim 7e of canister 7. This cross section of 23b shows open bottle neck at 10a and open lid fenestration 10c of lid 10 such that when inverted such as in FIG. 23 waste material from space 28 and space 24 may be dispensed. Handle 11 may also function as a holder and may be positioned for convenient material dispensing. An operator hold in one hand lever 11 while holding the canister base in the other hand for dispensing waste material.

FIG. 24 is a front elevation cross section of an alternative lid canister embodiment combination having alternative shaped prime manifold transfer container disposed therein. In this embodiment canister housing 31 and transfer container 1d have a near net shape fit in diameter. Patient suction tubing 19 is shown connected to allow ingress, port 26 at tubing connector 19a allow ingress, port 26 is shown extending from suction tubing 19 through transfer container neck into space 28. Container egress port is shown extending from the inside space 28 of container 1d in extending upwardly through the container neck through egress port 27 connecting to communication link tubing at elbow 17a, elbow 18a communicates with lid fenestration to provide negative atmospheric pressure communication to space 24. Prime manifold transfer container 1d and lid embodiment 25 form a seal together at 6, lid 25 and canister housing 31 form a seal at five together with canister housing 31. Vacuum tubing 20 is shown connected to lid 25 by port tubing connector at 20a. A vacuum source draws negative air atmospheric pressure through tubing 20 which draws pressure into space 24 which draws pressure through elbow 18, through communication link 16, through elbow 17a, through pressure egress port 27 provides a negative atmospheric pressure in the inside chamber of prime manifold transfer container 1d which provides negative atmospheric pressure through ingress port 26 to suction tubing 19 which communicates the negative atmospheric pressure draw to a suction wand at the source of waste material.

FIG. 24a is a top plan view of the alternative transfer container housing lid embodiment of FIG. 24 disclosing this top plan view. Patient suction tubing 19 is connected to ingress port connector 26 through tubing connector 19a to ingress port connector 26 extends upwardly from the top of lid 25 downwardly into a transfer container space. Egress port connector 27 extends from within the transfer container space upwardly to connect to elbow 17a. Communication tube 16 is connected via elbows 17a and 18a. Elbow 18a is connected through port fenestration of lid 25. Lid fenestrations connects elbow 18a to the inside of chamber 24 of canister 31. Vacuum source tubing 20 is shown connected to lid 25 by suction tubing connector 20a.

FIG. 24b is a top perspective cross section taken along the midlines through lid fenestration 10d ingress connector 26 and ingress connector 27 and lid fenestration 10c. Features disclosed in this FIG. 24b are similar to those shown in FIGS. 24 and 24a. It is noted however that the incremental marking on the outside of canister housing 31 as shown by 29 demonstrate the same volumetric fill lever that would be viewed as the incremental markings as shown on the wall of the prime manifold transfer container shown by 30.

FIG. 24c is a side elevation view of the exterior of housing 31 and lid 25. Shown here are operational features similar to that of FIGS. 24, 24a and 24b however a side view of incremental volumetric measurement indicia 29 associated with the outside canister wall in volumetric measurement level indicia 30 representing the volume fill level on the prime manifold transfer container are disposed at levels equally representing substantially similar to volumetric material cubic capacity. It is noted that in FIGS. 24, 24a and 24b and 24c, lid 25 is constructed of a single piece having a physical and functional capacity to dispose a prime manifold container and an intravenous solution container both within the same structure. It is understood that the two piece lid and canister combination may be used to provide connection with and intravenous solution container and a pour bottle. It is also understood that such lid connection site may be configured to connect to a variety of prime manifold container design configurations not only is such configuration as the dual spiking and threading shown by FIGS. 24 through 25c, but by any number of connection means such as a press fit, a slip fit, a push on fit, a push and twist, a double spike; a single spike, as dual lumen spike, a multi-lumen spike. It is also understood that the lid and canister combination shown in the instant case may be manufactured in a manner that the lid and canister housing may be formed as a unitary piece, is the forming tool such that when a lid is removed from the tool a canister housing is removed from the tool, such unitary relationship may be established by a living hinge which connects the lid to the canister and allows placement of the lid on the canister and removal of the lid on the canister. These design structures are intended to connect to prime manifold transfer containers made from different manufacturing process, different processes include an intravenous solution container manufacturing of laminating sheets along a periphery to obtain a container, blow fill seal manufacturing processes whereby parison(s)/extrusion(s) are formed and shaped into container(s) using suitable blow fill seal materials, blow molding processes whereby extrusion/parison(s) are formed and shaped into container(s) using one of the various types of suitable blow molding materials, form fill seal processes whereby transferable materials/contents are contained in the many form fill seal manufacturing methods. The instant application anticipates the instant lid housing transfer container connection invention of the instant application may be made in combination, or with may be made unitary to provide convenient collection of materials.

FIG. 25 shows similar lid canister features disposed within the canister is an intravenous solution container having two of its ports spiked by ingress connector 26 and egress connector 27. It is understood that in this embodiment one or more ingress and egress spikes could be used. It is considered a unique and novel aspect of this embodiment that the container collection systems of FIGS. 24 through 25c may seal there within both a liquid transfer container connecting through a neck connection and also a accommodate a flexible bag type of container such as an irrigation solution container, or a container for transfer of inject able solution. The lid embodiment connects to the pour spout/bottle neck or an IV solution spike port as commonly found in an intravenous solution container or other type of access port. It is also understood that such port connection may include a leur lock, a locking lug connection, a slip fit, a press fit a rotational connection, a threaded connection, a needless port type of connection such that the same needle less access port connection that would accommodate a syringe would also be connectable to the lid combination of the instant invention. It is the intension of the instant case to provide transfer container connection that are convenient, and which may already be present (but not necessarily) in association with the transfer container to then provide and extended useful life connection so the transfer container may be utilized as a collection container using structure combinations and methods which are novel as disclosed by the instant application. It is also anticipated by the instant application that adapters may be used to conveniently connect a transfer container to varieties of combinations of lid and canisters as disclosed in the instant cast for the purposes of reducing waste, reducing cost, reducing handling, reducing internal distribution and improving efficiency in the supply chain.

Similar negative atmospheric pressure operational flow principles apply here. A negative atmospheric pressure is drawn on vacuum source tubing 20 which is connected at lid 25 by tube connector 20a, negative draw is pulled through lid fenestration 10d into canister space 24. The negative atmospheric pressure continues to be pulled from canister space 24 through lid fenestration 10c an elbow 18a through communication tubing 16 through elbow 17a through egress port 17a of lid 25 of negative atmospheric pressure on the inside of intravenous solution container 28. The negative draw pressure continues to pull through ingress port 26 on lid 25 through patient suction tubing 19 and connector 19a and to a suction wand at a site of suction.

FIG. 25a shows a top plan view of the features disclosed in FIG. 25.

FIG. 25b is a side perspective cross section taken through lid fenestration 10d ingress port 26, egress port 27 and lid fenestration 10c. FIG. 25c is a side elevation view of the embodiments of FIG. 25, 25a and 25b.

What is claimed is:

1. A supply chain method comprising,
a) egressing a fluent material from a container,
b) enclosing said container inside a housing having a space therein, said housing configured to retain a portion of said container inside a vacuum draw path, a vacuum source configured to conduct a vacuum draw force away from said container and away from a supply of waste,
c) applying said vacuum force to said container and said space, wherein application of said vacuum force to said housing establishes transfer of waste material from said supply of waste toward said container.

2. A supply chain method of claim 1 wherein said housing configured to retain various containers of different sizes.

3. A supply chain method of claim 1 wherein said housing configured to retain various containers said received having different labels.

4. A supply chain method of claim 1 wherein said housing configured to retain various containers having different numbers of ports.

5. A supply chain method of claim 1 wherein said housing configured to retain various types of containers.

6. A supply chain method of claim 1 wherein said housing configured to retain various containers of different volumes.

7. A supply chain method of claim 1 wherein said housing configured to retain various containers having egressed different fluent materials.

8. A supply chain method of claim 1 wherein said housing configured to retain various containers labeled to enclose different fluent materials comprised of different formularies.

9. A supply chain method of claim 1 wherein said housing configured to retain various containers of different fluent materials.

10. A supply chain method of claim 1 wherein said housing configured to retain various containers procured for different said egress applications.

11. A supply chain method of claim 1 wherein said housing configured to retain various containers received from different supply chains, said fluent materials being egressed toward various said fluent material egress application options.

12. A supply chain method of claim 1 comprising,
a) providing more than one of said housings configured to retain more than one of said spaces and different containers, a plurality of supply chains are established by a plurality of said containers, a plurality of said spaces and different pluralities of fluent materials egress application options.

13. A supply chain method of claim 12 wherein said housing configured to retain various containers, said various containers having different flexibility.

14. A method of claim 12 comprising,
a) said container being a blow molded container,
b) conditioning a portion said blow molded container inside at least a portion of said path, said condition includes said egress, said force conduction, said force and maintenance of said space configuration.

15. A method of claim 12 comprising,
a) said container being a blow fill seal container,
b) conditioning a portion of said blow fill seal container inside at least a portion of said path, said condition includes said egress, said force conduction, said force and maintenance of said space configuration.

16. A method of claim 12 comprising,
a) said container being a thermally laminated sheets container,
b) conditioning a portion said thermally laminated sheets container inside at least a portion of said path, said condition includes said egress, said force conduction, said force and maintenance of said space configuration.

17. A supply chain method of claim 1 comprising,
a) establishing a plurality of composite draw paths, said paths configured to conduct a plurality of said force egresses away from a plurality of different said containers and a plurality of said spaces.

18. A supply chain method of claim 1 comprising,
a) integrating pluralities of various composite vacuum draw paths with pluralities of various said spaces, said containers, said forces, said housings, said egresses and said sources, said housings configured to retain different containers having different path connection configurations, various vacuum paths being configured to connect to at least more than one of said different connection configurations.

19. A supply chain method of claim 1 comprising,
a) integrating waste collection systems with different containers, said different containers retained to egress draw forces towards a plurality of said draw sources.

20. A supply chain method of claim 19 comprising,
a) applying said vacuum at an intermediate portion of said draw path.

21. A supply chain method of claim 1 wherein said housing configured to retain various containers made from different materials.

22. A supply chain method of claim 1 wherein said housing configured to retain various containers having egressed different materials.

23. A supply chain method of claim 1 wherein said housing configured to retain containers having enclosed and egressed materials of different color.

24. A method of claim 1 comprising,
a) reducing separate device recycling by replacement of said device with said container, said housing being configured to retain different said space configurations.

25. A method of claim 1 comprising,
a) reducing separate collection device reprocessing by replacement of said device with said container, said housing being configured to retain different said space configurations.

26. A method of claim 1 comprising,
a) reducing separate collection device rewashing by replacement of said device with said container, said housing being configured to retain different said space configurations.

27. A method of claim 1 comprising,
a) reducing separate collection device cleaning by replacement of said device with said container, said housing being configured to retain different said space configurations.

28. A method of claim 1 comprising,
a) reducing separate collection device reuse by replacement of said device with said container, said housing being configured to retain different said space configurations.

29. A method of claim 1 comprising,
a) reducing separate collection device waste by replacement of said device with said container, said housing being configured to retain different said space configurations.

30. A method of claim 1 comprising,
a) reducing separate disposable collection devices by replacement of said devices with a plurality of said containers, said housing being configured to retain different said space configurations.

31. A method of claim 1 comprising,
a) reducing separate disposable collection device costs by replacement of said device with said container, said housing being configured to retain different said space configurations.

32. A method of claim 1 comprising,
a) reducing separate disposable collection canister liner use by replacement of said liners with said containers, said housing being configured to retain different said space configurations.

33. A method of claim 1 comprising,
a) reducing separate disposable collection liner costs by replacement of said liner with said container, said housing being configured to retain different said space configurations.

34. A method of claim 1 comprising,
a) reducing separate collection device labor by replacement of said device with said container, said housing being configured to retain different said space configurations.

35. A method of claim 1 comprising,
a) reducing separate collection device inventory sorting by replacement of said device with said container, said housing being configured to retain different said space configurations.

36. A method of claim 1 comprising,
a) reducing separate collection device waste by replacement of said devices with said container, said housing being configured to retain different said space configurations.

37. A method of claim 1 comprising,
a) reducing separate collection device internal distribution by replacement of said device with said container, said housing being configured to retain different said space configurations.

38. A method of claim 1 comprising,
a) reducing separate collection device inventory by replacement of said device with said container, said housing being configured to retain different said space configurations.

39. A method of claim 1 comprising,
a) reducing separate collection device inventory handling by replacement of said device with said container, said housing being configured to retain different said space configurations.

40. A method of claim 1 comprising,
a) reducing separate collection device inventory handling costs by replacement of said device with said container, said housing being configured to retain different said space configurations.

41. A method of claim 1 comprising,
a) reducing separate collection devices by replacement of said devices with said containers, said elimination establishes increased inventory space, said housing being configured to retain different said space configurations.

42. A method of claim 1 comprising,
a) reducing separate collection device internal processing by replacement of said device with said container, said housing being configured to retain different said space configurations.

43. A method of claim 1 comprising,
a) reducing separate collection device receiving by replacement of said device with said container, said housing being configured to retain different said space configurations.

44. A method of claim 1 comprising,
a) reducing separate collection device receiving cost by replacement of said device with said container, said housing being configured to retain different said space configurations.

45. A method of claim 1 comprising,
a) reducing separate collection device waste disposal by replacement of said device with said container, said housing being configured to retain different said space configurations.

46. A method of claim 1 comprising,
a) reducing separate collection device waste disposal cost by replacement of said device with said container.

47. A method of claim 1 comprising,
a) reducing separate collection device sterilization by replacement of said device with said container, said housing being configured to retain different said space configurations.

48. A method of claim 1 comprising,
a) reducing separate collection device cost by replacement of said device with said container, said housing being configured to retain different said space configurations.

49. A method of claim 1 comprising,
a) reducing separate disposable collection device consumption by replacement of said device with said container, said housing being configured to retain different said space configurations.

50. A method of claim 1 comprising,
a) reducing separate collection device inventory management by replacement of said device with said container, said housing being configured to retain different said space configurations.

51. A method of claim 1 comprising,
a) reducing separate collection device inventory management cost by replacement of said device with said container, said housing being configured to retain different said space configurations.

52. A method of claim 1 comprising,
a) reducing separate collection device handling by replacement of said devices with said container, said housing being configured to retain different said space configurations.

53. A method of claim 1 comprising,
a) reducing separate collection device handling costs by replacement of said devices with said container, said housing being configured to retain different said space configurations.

54. A method of claim 1 comprising,
a) reducing separate collection device procurement by replacement of said device with said container, said housing being configured to retain different said space configurations.

55. A method of claim 1 comprising,
a) reducing separate collection device procurement costs by replacement of said devices with said container, said housing being configured to retain different said space configurations.

56. A method of claim 1 comprising,
a) applying said container retention in plurality with respect to a plurality of containers, said retention to include a plurality of said egresses, a plurality of said force conductions and a plurality of said spaces and a plurality of said paths and a plurality of said housings.

57. A method of claim 56 wherein said containers are different.

58. A method of claim 1 comprising,
a) applying said container retention in plurality with respect to a plurality of volumes of egressed fluent materials, said retention to include a plurality of said housings, a plurality of said containers, a plurality of said egresses, a plurality of said force conductions, and a plurality of said spaces and a plurality of said paths.

59. A method of claim 58 wherein said fluent materials are different.

60. A method of claim 1 comprising,
a) applying said container retention in plurality with respect to a plurality of supply chain consumptions, said retention to include a plurality of said housings, a plurality of said containers, a plurality of said egresses, a plurality of said paths, a plurality of said spaces and a plurality of said force conductions.

61. A method of claim 60 wherein said consumptions are different.

62. A method of claim 1 comprising,
  a) applying said container retention in plurality with respect to a plurality of said egresses, said retention to include a plurality of said containers, a plurality of said retentions, a plurality of said spaces, a plurality of said sources, a plurality of composite draw paths, a plurality of said force conductions, a plurality of different said space configurations and a plurality of said housings.

63. A method of claim 62 wherein said containers are different.

64. A method of claim 1 comprising,
  a) applying said container retention in plurality with respect to a plurality of waste collection systems, said retention to include a plurality of said containers, a plurality of said egresses, a plurality of said retentions, a plurality of said spaces, a plurality of said draw forces, a plurality of said housings, said draw forces configured to draw said forces in plurality away from said plurality of said containers by a plurality of said force conductions, said retention to include maintenance of a plurality of said spaces configurations.

65. A method of claim 64 wherein said draw paths are configured to conduct forces along are differently configured said spaces.

66. A method of claim 1 comprising,
  a) applying said container retention in plurality with respect to a plurality of housings, said retention to include a plurality of said containers, a plurality of said egresses, a plurality of said forces, said forces configured to be drawn away from a plurality of said spaces, a plurality of said sources, a plurality of composite draw paths, said retention to include maintenance of a plurality of said spaces configurations.

67. A method of claim 66 comprising,
  a) drawing said forces away from differently configured spaces.

68. A method of claim 1 wherein said housings are adapted to said retain at least a portion of different containers inside said space at different times.

69. A supply chain method comprising,
  a) egressing a fluent material from a container having a fluent material therein,
  b) enclosing said container inside an outer housing having a space therein, wherein said outer housing is configured to receive a vacuum draw force from a draw path,
  c) applying a vacuum force to said housing wherein application of said force to said housing establishes a transfer of waste material from a supply of waste into said container.

70. A supply chain method comprising,
  a) egressing a material from a container,
  b) placing said container into a housing, said housing having a space therein and a vacuum draw source connected to a draw path, said housing configured to receive a vacuum draw force from said path,
  c) applying said vacuum force to said housing and said container, wherein application of said vacuum draw force to said path transfers waste material from a supply of waste toward said container.

71. A supply chain method comprising,
  a) egressing a material from a container,
  b) enclosing said container inside an outer housing, a portion of said container to be configured to be retained inside a portion of a vacuum draw path, said path configured to connect a space inside said outer housing to a source of vacuum draw forces,
  c) connecting said container to said source via said path, wherein application of said vacuum draw forces establishes transfer of waste material from a supply of waste along said path toward said container.

* * * * *

UNITED STATES PATENT AND TRADEMARK OFFICE
CERTIFICATE OF CORRECTION

| | | |
|---|---|---|
| PATENT NO. | : 8,137,329 B2 | |
| APPLICATION NO. | : 11/087538 | |
| DATED | : March 20, 2012 | |
| INVENTOR(S) | : Jack W. Romano and Adam L. Smith | |

It is certified that error appears in the above-identified patent and that said Letters Patent is hereby corrected as shown below:

1) Column 6, line 8: delete "our" and insert --out-- to read "carry out the"....
2) Column 6, line 16: delete "%" to read "embodiments for".....
3) Column 7, line 6: delete "t" and insert --to-- to read "container to the".....
4) Column 7, line 47: delete "," and insert --.-- to read "receptacle. An"....
5) Column 7, lines 50 and 51: delete "positing" and insert --positioning-- to read "b) positioning the"....
6) Column 7, line 59: delete "of" and insert --or-- to read "system or a"....
7) Column 8, line 11: delete "in" and insert --a-- to read "least a portion"....
8) Column 8, line 27: delete "a," and insert --a)-- to read "comprising a) fabricating"....
9) Column 8, line 35: delete sentence "Another object of the invention." to read "container. One"....
10) Column 8, line 56: delete "receive" and insert --receiver-- to read "a receiver wherein"....
11) Column 10, lines 3 and 4: delete "b)" and insert --.-- to read "above). It is"....
12) Column 10, lines 27 and 28: delete "tot hat" on line 28 and insert --to that-- to read "capacity to that of"....
13) Column 10, line 39: insert --is-- between --view-- and --related-- to read "view is related"....
14) Column 11, line 8: delete "markets" and insert --marks-- to read "indicia marks going"....
15) Column 11, line 55: delete "W" to read "detail which"....
16) Column 15, line 42: delete "I" and insert --is-- to read "Fig. 22 is a".....
17) Column 16, line 61: delete "physician" and insert --physical-- to read "same physical and"....
18) Column 16, line 62: delete "prim" and insert --prime-- to read "a prime manifold"....
19) Column 17, line 4: delete "a" and insert --an-- to read "FIG. 4 is an exploded".....
20) Column 17, line 8: delete "spacelink" and insert --space-- to read "12d, space link"....
21) Column 17, line 31: delete "pint" and insert --a point-- to read "such a point as"....
22) Column 17, line 54: delete "physician" and insert --physical-- to read "same physical and functional"....
23) Column 17, line 64: delete "describe" and insert --described-- to read "as described in"....
24) Column 17, line 66: delete "shown" and insert --shows-- to read "3 shows indicia"....
25) Column 17, line 67: insert --system-- between --collection-- and --3-- to read "collection system 3"....

Signed and Sealed this
Nineteenth Day of June, 2012

David J. Kappos
*Director of the United States Patent and Trademark Office*

CERTIFICATE OF CORRECTION (continued)
U.S. Pat. No. 8,137,329 B2

26) Column 18, line 13: delete "bow" and insert --blow-- to read "partial blow up"....
27) Column 18, line 27: delete "I" and insert --in-- to read "Shown in this"....
28) Column 18, line 28: delete "rime" and insert --rim-- to read "upper rim of"....
29) Column 18, line 43: delete "and" and insert --an-- to read "provides an under"....
30) Column 18, line 50: delete "to" and insert --top-- to read "a top perspective"....
31) Column 18, line 64: insert --up-- between --blow-- and --detail-- to read "blow up detail"....
32) Column 18, line 65: delete "of" and insert --up-- to read "blow up view"....
33) Column 19, lines 32: delete "lined" and insert --lines-- to read "two lines"....
34) Column 19, line 54: delete "operated" and insert --operate-- to read "to operate"....
35) Column 20, line 26: delete "prim" and insert --prime-- to read "three prime manifold"....
36) Column 20, line 44: delete "to" to read "a perspective"....
37) Column 20, line 51: delete "10 discloses" to read "FIG. 10 discloses lever"....
38) Column 21, line 34: insert --second-- between --and-- and --hook-- to read "and second hook"....
39) Column 21, line 35: delete "arrow" and insert --arrows-- to read "Three arrows defining"....
40) Column 21, line 58: delete "f" to read "DV×2 10c"....
41) Column 22, line 14: delete "dist5raction" and insert --distraction-- to read "Maximum distraction delta"....
42) Column 22, line 24: delete "shown" and insert --shows a-- to read "FIG. 10i shows a moment"....
43) Column 22, line 39: delete "is" and insert --in-- to read "fits in sealable"....
44) Column 23, line 1: delete "bee" and insert --been-- to read "having been press"....
45) Column 23, line 24: delete "atop" and insert --a top-- to read "FIG. 12 is a top perspective"....
46) Column 23, line 42: insert --up-- between --blow-- and --discloses-- to read "blow up discloses"....
47) Column 25, line 13: delete "identifies" and insert --identities-- to read "numerical identities as"....
48) Column 25, line 38: delete "rime" and insert --rim-- to read "of rim 7e"....
49) Column 25, line 62: delete "d-0" and insert --D-0-- to read "to D-0 to"....
50) Column 27, line 59: insert --as-- between --identified-- and --a-- to read "identified as a"....
51) Column 27, line 67: delete "I" and insert --from-- to read "removed from this"....
52) Column 28, line 1: delete "a" and insert --along-- to read "taken along lines"....
53) Column 29, line 39: delete "containing" and insert --container-- to read "transfer container while"....
54) Column 29, line 67: delete "mater" and insert --matter-- to read "waste matter whether"....
55) Column 30, line 9: delete "245" and insert --24-- to read "space 24 may"....
56) Column 30, line 40: delete "hold" and insert --holds-- to read "operator holds in"....
57) Column 35, line 45: delete "said elimination" to read "containers, establishes"....
58) Column 37, line 29: delete "are" to read "along differently"....